(12) United States Patent
Liu

(10) Patent No.: US 7,319,149 B2
(45) Date of Patent: Jan. 15, 2008

(54) CHELANTS AND MACROCYCLIC METAL COMPLEX RADIOPHARMACEUTICALS THEREOF

(75) Inventor: Shuang Liu, Chelmsford, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 484 days.

(21) Appl. No.: 10/864,792

(22) Filed: Jun. 9, 2004

(65) Prior Publication Data

US 2005/0010038 A1    Jan. 13, 2005

Related U.S. Application Data

(60) Provisional application No. 60/478,462, filed on Jun. 13, 2003.

(51) Int. Cl.
*C07D 401/02* (2006.01)
(52) U.S. Cl. ........................... 546/255; 546/256
(58) Field of Classification Search .......... 546/256, 546/255
See application file for complete search history.

(56) References Cited

U.S. PATENT DOCUMENTS

| | | | |
|---|---|---|---|
| 4,427,646 A | 1/1984 | Olexa et al. | 424/1.1 |
| 4,578,079 A | 3/1986 | Ruoslahti et al. | 623/11 |
| 4,792,525 A | 12/1988 | Ruoslahti et al. | 435/240.243 |
| 5,086,069 A | 2/1992 | Klein et al. | 514/399 |
| 5,206,370 A | 4/1993 | Schwartz et al. | 546/281 |
| 5,217,705 A | 6/1993 | Reno et al. | 424/1.1 |
| 5,270,030 A | 12/1993 | Vogel et al. | 424/9 |
| 5,277,892 A | 1/1994 | Rhodes | 424/1.69 |
| 5,279,812 A | 1/1994 | Krstenansky et al. | 424/1.1 |
| 5,350,837 A | 9/1994 | Bridger et al. | 534/14 |
| 5,744,120 A | 4/1998 | Edwards et al. | 424/1.64 |
| 5,750,088 A | 5/1998 | Sworin et al. | 424/1.69 |
| 5,753,520 A | 5/1998 | Schwartz et al. | 436/542 |
| 5,776,894 A | 7/1998 | Albert et al. | 514/11 |
| 5,792,444 A | 8/1998 | Fischman et al. | 424/1.69 |
| 5,871,711 A | 2/1999 | Dean et al. | 424/1.69 |
| 5,879,659 A | 3/1999 | Edwards et al. | 424/1.69 |
| 6,015,904 A | 1/2000 | Sworin et al. | 546/278.7 |
| 6,022,523 A | 2/2000 | DeGrado et al. | 424/1.69 |
| 6,251,364 B1 | 6/2001 | Liu | 424/1.69 |
| 6,329,513 B1 | 12/2001 | Archer et al. | 534/14 |
| 6,416,733 B1 | 7/2002 | Barrett et al. | 424/1.65 |

FOREIGN PATENT DOCUMENTS

| | | |
|---|---|---|
| EP | 0 410 537 A1 | 1/1991 |
| EP | 0 410 539 A1 | 1/1991 |
| EP | 0 410 541 A1 | 1/1991 |
| EP | 0 422 937 B1 | 3/1994 |
| EP | 0 422 938 B1 | 2/1995 |
| EP | 0 398 143 B1 | 3/1995 |
| EP | 0 478 328 B1 | 1/1996 |
| EP | 0 425 212 B1 | 4/1999 |
| GB | 2268494 A | 1/1994 |
| WO | WO 89/05150 A1 | 6/1989 |
| WO | WO 89/10135 A1 | 11/1989 |
| WO | WO 90/03391 A1 | 4/1990 |
| WO | WO 90/15818 A1 | 12/1990 |
| WO | WO 91/01331 A1 | 2/1991 |
| WO | WO 91/15515 A1 | 10/1991 |
| WO | WO 92/13572 A1 | 8/1992 |
| WO | WO 93/12819 A1 | 7/1993 |
| WO | WO 93/17719 A1 | 9/1993 |
| WO | WO 93/23085 A1 | 11/1993 |
| WO | WO 94/05269 A1 | 3/1994 |
| WO | WO 98/15295 A3 | 4/1998 |
| WO | WO 00/00178 A1 | 6/2000 |
| WO | WO 00/35488 A3 | 6/2000 |
| WO | WO 01/98294 A2 | 12/2001 |
| WO | WO 02/36173 A3 | 5/2002 |

OTHER PUBLICATIONS

Baumgartner, H.R., "Eine neue methode zur erzeugung von thrombin durch gezielte Überdehnung der gefäβwand," *Z. Ges. Exp. Med.*, 1963, 137, 227-247 (see p. 243 for the English Summary).

Dewanjee, M.K., "The chemistry of $^{99m}$Tc-labeled radiopharmaceuticals," *Semin. In Nucl. Med.*, 1990, 20(1), 5-27.

Dilworth, J.R., et al., "The biomedical chemistry of technetium and rhenium," *Chem. Soc. Rev.*, 1998, 27, 43-55.

Edwards, D.S., et al., "New and versatile ternary ligand system for technetium radiopharmaceuticals: water soluble phosphines and tricine as coligands in labeling a hydrazinonicotinamide-modified cyclic glycoprotein IIb/IIIa receptor antagonist with $^{99m}$Tc," *Bioconjugate Chem.*, 1997, 8, 146-154.

Edwards, S.D., et al., "RP463: a stabilized technetium-99m complex of a hydrazine nicotinamide derivatized chemotactic peptide for infection imaging," *Bioconjugate Chem.*, 1999, 10, 884-891.

(Continued)

*Primary Examiner*—Zinna N. Davis
(74) *Attorney, Agent, or Firm*—Jennifer C. Chapman; John F. Levis; Woodcock Washburn LLP

(57) ABSTRACT

Chelants and macrocyclic metal complexes thereof, methods of preparing the chelants and macrocyclic metal complexes, and radiopharmaceutical compositions comprising the macrocyclic metal complexes are disclosed. Methods of using the macrocyclic metal complexes as radiopharmaceuticals for the diagnosis of cardiovascular disorders, infectious diseases and cancer are also disclosed. Chelants as bifunctional chelators (BFCs) for the radiolabeling of target-specific biomolecules, such as proteins, peptides, peptidomimetics, non-peptide receptor ligands, enzyme inhibitors, and enzyme substrates are disclosed. Methods of using macrocyclic metal complexes containing the chelant-biomolecule conjugates as target-specific diagnostic radiopharmaceuticals that selectively localize at sites of disease and allow an image to be obtained of the loci using gamma scintigraphy are disclosed. Methods of use of the radiopharmaceuticals as imaging agents for the diagnosis of cardiovascular disorders, such as thromboembolic disease or atherosclerosis, infectious disease and cancer are further disclosed.

10 Claims, No Drawings

OTHER PUBLICATIONS

Edwards, S.D., et al., "$^{99m}$Tc-labeling of hydrazones of a nydrazinonicotinamide conjugated cyclic peptide," *Bioconjugate Chem.*, 1999, 10, 803-807.

Elmaleh, SD.R., et al., "Rapid noninvasive detection of experimental atherosclerotic lesions with novel $^{99m}$Tc-labeled diadenosine tetraphosphates," *Proc. Natl. Sci. USA*, 1998, 95, 691-695.

Fischman, A.J., et al., "Infection imaging with technetium-99m-labeled chemotactic peptide analogs," *Semin. Nuc. Med.*, 1994, 24(2), 154-168.

Fritzberg, A.R., et al., "Approaches to radiolabeling of antibodies for diagnosis and therapy of cancer," *Pharmaceutical Res.*, 1988, 5(6), 325-334.

Griffiths, G.L., et al., "Radiolabeling of monoclonal antibodies and fragments with technetium and rhenium," *Bioconj. Chem.*, 1992, 3(2), 91-99.

Harris, T.D., et al., "Synthesis of stable hydrazones of a hydrazinonicotinyl-modified peptide for the preparation of $^{99m}$Tc-labeled radiopharmaceuticals," *Bioconjugate Chem.*, 1999, 10, 808-814.

Hartman, G.D., et al., "Non-peptide fibrinogen receptor antagonists. 1. Discovery and design of exosite inhibitors," *J. Med. Chem.*, 1992, 35, 4640-4642.

Hom, R.K., et al., "Technetium-99m-labeled receptor-specific small-molecule radiopharmaceuticals: recent developments and encouraging results," *Nucl. Med. & Biol.*, 1997, 24, 485-498.

Jurisson, S., et al., "Coordination compounds in nuclear medicine," *Chem. Rev.*, 1993, 93, 1137-1156.

Jurisson, S.S., et al., "Potential technetium small molecule radiopharmaceuticals," *Chem. Rev.*, 1999, 99, 2205-2218.

Larsen, S.K., et al., "[$^{99m}$Tc]Tricine: a useful precursor complex for the radiolabeling of hydrazinonicotinate protein conjugates," *Bioconjugate Chem.*, 1995, 6, 635-638.

Liu, S., et al., "Labeling a hydrazine nicotinamide-modified cyclic IIb/IIIa receptor antagonist with $^{99m}$Tc using aminocarboxylates as coligands," *Bioconjugate Chem.*, 1996, 7, 63-71.

Liu, S., et al., "$^{99m}$Tc labeling of highly potent small peptides," *Bioconjugate Chem.*, 1997, 8, 621-636.

Liu, S., et al., "A novel ternary ligand system for $^{99m}$TC-labeling of hydrazine nicotinamide-modified biologically active molecules using imine-N-containing heterocycles as coligands," *Bioconjugate Chem.*, 1998, 9, 583-595.

Liu, S., et al., "Radio-LC-MS for the characterization of $^{99m}$Tc-labeled bioconjugates," *Bioconjugate Chem.*, 2000, 11, 113-117.

Liu, S., et al., "Technetium complexes of a hydrazinonicotinamide-conjugated cyclic peptide and 2-hydrazinopyridine: synthesis and characterization," *Inorg. Chem.*, 1999, 38(6), 1326-1335.

Liu, S., et al, "99mTc-labeled small peptides as diagnostic radiopharmaceuticals," *Chem. Rev.*, 1999, 99, 2235-2268.

Liu, S., et al., "Bifunctional chelators for therapeutic lanthanide radiopharmaceuticals," *Bioconjugate Chem.*, 2001, 12, 7-34.

Narula, J., et al., "Noninvasive localization of experimental atherosclerotic lesions with mouse/human chimeric Z2D3 F(ab')$_2$ specific for the proliferatng smooth muscle cells of human atheroma," *Circulation*, 1995, 92, 474-484.

Naurla, J., et al., "Gamma imaging of atherosclerotid lesions: the role of antibody affinity in in vivo target localization," *J. Nucl. Cardiol.*, 1996, 3, 231-241.

Ojima, D., et al., "Design and synthesis of new RGD peptides as inhibitors of human platelet aggregation,"*204$^{th}$ Meeting of the Am. Chem. Soc.*, 1992, Abstract 44, 1 page.

Remington's Pharmaceutical Sciences, *17$^{th}$ Ed., Mack Publishing Co.*, 1985, p. 1418.

Roberts, D.C., et al., "Unusual amino acids in peptide synthesis," *The Peptides*, 1983, 5(6), 341-449.

Yuanfang, L., et al., "Radiolabeling of monoclonal antibodies with metal chelates," *Pure & Appl. Chem.*, 1991, 63, 427-463.

U.S. Appl. No. 10/864,857, filed Jun. 9, 2004, Liu.

CHELANTS AND MACROCYCLIC METAL COMPLEX RADIOPHARMACEUTICALS THEREOF

CROSS REFERENCE TO RELATED APPLICATIONS

This application claims the benefit of U.S. Application No. 60/478,462, filed Jun. 13, 2003, the entire disclosure of which is incorporated herein by reference.

FIELD OF THE INVENTION

This invention is related to chelants and macrocyclic metal complexes thereof, methods of preparing the chelants and macrocyclic metal complexes thereof, radiopharmaceutical compositions comprising the macrocyclic metal complexes and methods of their use for the diagnosis of cardiovascular disorders, infectious diseases and cancer.

BACKGROUND OF THE INVENTION

Radiopharmaceuticals are drugs containing a radionuclide and are used routinely in nuclear medicine department for the diagnosis or therapy of various diseases. They are mostly small organic or inorganic compounds with definite composition. They can also be macromolecules, such as antibodies and antibody fragments that are not stoichiometrically-labeled with a radionuclide. Radiopharmaceuticals form the chemical basis for nuclear medicine, a group of techniques used for diagnosis and therapy of various diseases. The in vivo diagnostic information is obtained by intravenous injection of the radiopharmaceutical and determining its biodistribution using a gamma camera. The biodistribution of the radiopharmaceutical depends on the physical and chemical properties of the radiopharmaceutical and can be used to obtain information about the presence, progression, and the state of disease.

Radiopharmaceuticals can be divided into two primary classes: those whose biodistribution is determined exclusively by their chemical and physical properties; and those whose ultimate distribution is determined by their receptor binding or other biological interactions. The latter class is often called target-specific radiopharmaceuticals.

In general, a target specific radiopharmaceutical can be divided into four parts: a targeting molecule, a linker, a bifunctional chelator (BFC), and a radionuclide. The targeting molecule serves as a vehicle, which carries the radionuclide to the receptor site at the diseased tissue. The targeting molecules can be macromolecules, such as antibodies. They can also be small biomolecules (BM): peptides, peptidomimetics, and non-peptide receptor ligands. The choice of biomolecule depends upon the targeted disease or disease state. The radionuclide is the radiation source. The selection of radionuclide depends on the intended medical use (diagnostic or therapeutic) of the radiopharmaceutical. Between the targeting molecule and the radionuclide is the BFC, which binds strongly to the metal ion via several coordination bonds and is covalently attached to the targeting molecule either directly or through a linker. Selection of a BFC is largely determined by the nature and oxidation state of the metallic radionuclide. The linker can be a simple hydrocarbon chain or a long poly (ethylene glycol) (PEG), which is often used for modification of pharmacokinetics. Sometimes, a metabolizable linker is used to increase the blood clearance and to reduce the background activity, thereby improving the target-to-background ratio.

The use of metallic radionuclides offers many opportunities for designing new radiopharmaceuticals by modifying the coordination environment around the metal with a variety of chelators. The coordination chemistry of the metallic radionuclide will determine the geometry of the metal chelate and the solution stability of the radiopharmaceutical. Different metallic radionuclides have different coordination chemistries, and require BFCs with different donor atoms and chelator frameworks. For "metal essential" radiopharmaceuticals, the biodistribution is exclusively determined by the physical properties of the metal chelate. For target-specific radiopharmaceuticals, the "metal tag" may have significant impact on the target uptake and biodistribution of the radiopharmaceutical. This is especially true for metalloradiopharmaceuticals based on small molecules since in many cases the metal chelate contributes greatly to the overall size and molecular weight. Therefore, the design and selection of the BFC is very important for the development of a new diagnostic or therapeutic radiopharmaceutical.

Metallic radionuclides, such as $^{99m}$Tc, $^{117m}$Sn, $^{111}$In, $^{67}$Ga, $^{68}$Ga, $^{89}$Zr, and $^{64}$Cu, have been proposed for diagnostic imaging. Nearly 80% of radiopharmaceuticals used in nuclear medicine are $^{99m}$Tc-labeled compounds. The reason for such a preeminent position of $^{99m}$Tc in clinical use is its favorable physical and nuclear characteristics. The 6 hour half-life is long enough to allow those skilled in the art to carry out radiopharmaceutical synthesis and for nuclear medicine practitioners to collect useful images. At the same time, it is short enough to permit administration of millicurie amounts of $^{99m}$Tc radioactivity without significant radiation dose to the patient. The monochromatic 140 KeV photons are readily collimated to give images of superior spatial resolution. Furthermore, $^{99m}$Tc is readily available from commercial $^{99}$Mo—$^{99m}$Tc generators at low cost.

One of the characteristics of technetium is its rich and diverse redox chemistry. As of yet, there is no effective chemistry that can be used to attach the pertechnetate anion to a small biomolecule. Therefore, the Tc(VII) in $^{99m}$TcO$_4^-$ has to be reduced to a lower oxidation state in order to produce a stable $^{99m}$Tc-biomolecule complex or to a reactive intermediate complex from which $^{99m}$Tc can be easily transferred to the BFC-BM conjugate.

A BFC can be divided into three parts: a binding unit, a conjugation group, and a spacer (if necessary). An ideal BFC is that which is able to form a stable $^{99m}$Tc complex in high yield at very low concentration of the BFC-BM conjugate under mild conditions. There are several requirements for an ideal BFC. First, the binding unit can selectively stabilize an intermediate or lower oxidation state of Tc so that the $^{99m}$Tc complex is not subject to redox reactions; oxidation state changes are often accompanied by transchelation of $^{99m}$Tc from a $^{99m}$Tc-BFC-BM complex to the native chelating ligands in biological systems. Secondly, the BFC forms a $^{99m}$Tc complex that has thermodynamic stability and kinetic inertness with respect to dissociation. Thirdly, the BFC forms a $^{99m}$Tc complex with a minimum number of isomers since different isomeric forms of the $^{99m}$Tc-chelate may have significant impact on the biological characteristics of the $^{99m}$Tc-BFC-BM complex. Finally, the conjugation group can be easily attached to the biomolecule.

For receptor-based radiopharmaceuticals, injection of large amount of BFC-BM may result in receptor site saturation, blocking the docking of the $^{99m}$Tc-labeled BFC-BM, as well as unwanted side effects. In order to avoid these problems, the concentration of the BFC-BM in the radiopharmaceutical composition should be low. Otherwise, a post-labeling purification is often needed to remove excess unlabeled BFC-BM, which is time consuming and thus not amenable for clinical use. Therefore, the BFC attached to the biomolecule should have very high radiolabeling efficiency in order to achieve high specific activity.

For $^{99m}$Tc-labeling of biomolecules, bifunctional chelators include $N_2S_2$ diaminedithiols, $N_2S_2$ diamidedithiols, $N_3S_2$ monoaminemonoamidedithiols, $N_3S$ monoaminediamidethiols, $N_3S$ triamidethiols, and 6-hydrazinonicotinamide (HYNIC). Various $^{99m}$Tc-labeling techniques have been described in recent reviews (Liu et al., *Bioconjugate Chem.* 1997, 8, 621; Hom, R. K. and Katzenellenbogen, J. A. *Nucl. Med. Biol.* 1997, 24, 485; Dewanjee, M. K. *Semin. Nucl. Med.* 1990, 20, 5; Jurisson, et al., *Chem. Rev.* 1993, 93, 1137; Dilworth, J. R. and Parrott, S. J. *Chem. Soc. Rev.* 1998, 27, 43; Liu, et al., *Bioconj. Chem.* 1997, 8, 621; Liu, et al., *Pure & Appl. Chem.* 1991, 63, 427; Griffiths, et al., *Bioconj. Chem.* 1992, 3, 91; Liu, S. and Edwards, D. S. *Chem. Rev.* 1999, 99, 2235; Jurisson, S. and Lydon, J. D. *Chem. Rev.* 1999, 99, 2205). After radiolabeling, the resulting reaction mixture may optionally be purified using one or more chromatographic methods, such as Sep-Pack or high performance liquid chromatography (HPLC). The preferred radiolabeling procedures are those in which the chelation can be achieved without post-labeling purification.

Rhenium has two isotopes ($^{186}$Re and $^{188}$Re) which might be useful in tumor therapy. $^{186}$Re has a half-life of 3.68 days with •-emission (Emax=1.07 MeV, 91% abundance) and a gamma-photon (E=137 keV, 9% abundance) which should allow imaging during therapy. $^{188}$Re has a half-life of 16.98 hours with an intense •-emission (Emax=2.12 MeV, 85% abundance) and 155 keV gamma photons (15% abundance). The related chemistry, medical applications, and radiolabeling with $^{186/188}$Re by direct and indirect methods have been reviewed (Fritzberg, et al., *Pharmaceutical Res.* 1988, 5, 325; Dilworth, J. R. and Parrott, S. *J. Chem. Soc. Rev.* 1998, 27, 43). Since the rhenium chemistry is very similar to technetium chemistry due to the periodic relationship, the methods used for the radiolabeling of biomolecules with $^{99m}$Tc should apply to that with $^{186/188}$Re.

U.S. Pat. Nos. 5,206,370 and 5,753,520 disclose the use of organic hydrazines, such as HYNIC, and hydrazides as BFCs to modify proteins for labeling with radionuclides. For labeling with $^{99m}$Tc, the hydrazino-modified protein is reacted with a reduced technetium species, formed by reacting [$^{99m}$Tc]pertechnetate with a reducing agent in the presence of a dioxygen chelating agent. The technetium is bonded through what are believed to be hydrazino or diazenido linkages. Since HYNIC moiety only occupies one or two coordination sites of the Tc, the coordination sphere of the Tc is often completed by the use of coligands, such as glucoheptonate and lactate.

U.S. Pat. No. 5,350,837 discloses a series of functionalized aminocarboxylates and their use as coligands in the radiolabeling of hydrazino-modified proteins. The improvements are manifested by shorter reaction times and higher specific activities for the radiolabeled protein. The best reported example is tricine.

U.S. Pat. No. 6,329,513 discloses a series of $^{99m}$Tc complexes having a ternary ligand system containing a hydrazino or diazenido ligand, a phosphine ligand and a halide, in which the substituents on the hydrazido or diazenido ligand and phosphine ligand can be independently varied. However, the radiopharmaceuticals in this disclosure are formed in low specific activity. This disclosure shows no evidence that the halide ligand is indeed bonded to the metal center at the tracer ($^{99m}$Tc) level. The disclosure does not teach or suggest how to achieve the superior control of biological properties that will result from a ternary ligand system in which the substituents on the three types of ligands can be independently varied. Therefore, there remains a need for new ternary ligand systems, which form radiopharmaceuticals with high specific activity.

The advantage of using HYNIC as the BFC is its high labeling efficiency (rapid and high yield radiolabeling) and the choice of various coligands such as tricine and glucoheptonate, which allows easy modification of the hydrophilicity and pharmacokinetics of the $^{99m}$Tc-labeled small peptides. For the $^{99m}$Tc-labeling of HYNIC-conjugated small biomolecules, however, the use of tricine or glucoheptonate as coligands suffers two major drawbacks: the solution instability of binary technetium complexes [$^{99m}$Tc(HYNIC-BM)(L)$_2$] (BM=biomolecule; L=tricine or glucoheptonate) in the absence of excess coligand, and the presence of multiple species of these complexes in solution due to different bonding modalities of HYNIC and the tricine or glucoheptonate coligands (Liu, et al., *Bioconjugate Chem.* 1996, 7, 63; Edwards, et al., *Bioconjugate Chem.* 1997, 8, 146; Edwards, et al., *Bioconjugate Chem.* 1999, 10, 884).

To increase the solution stability and minimize the number of isomeric forms in the [$^{99m}$Tc]HYNIC complexes, U.S. Pat. No. 5,744,120 discloses a ternary ligand system comprising an HYNIC-conjugated biomolecule (HYNIC-BM) as a ligand, tricine and a water-soluble phosphine as coligands. The new ternary ligand system forms ternary ligand $^{99m}$Tc complexes in good yield and with high solution stability and a minimal number of isomeric forms. The Tc:HYNIC-BM:L:tricine (L=water-soluble phosphine) ratio was determined to be 1:1:1:1 through a series of mixed ligand experiments (Edwards, et al., *Bioconjugate Chem.* 1997, 8, 146), and has been confirmed by the FAB (fast-atom bombardment) and LC-MS data (Liu, et al., *Inorg. Chem.* 1999, 38, 1326; Liu, et al., *Bioconjugate Chem.* 2000, 11, 113).

U.S. Pat. No. 5,879,659 discloses novel ternary ligand $^{99m}$Tc complex radiopharmaceuticals comprising an imine-N heterocycle, such as pyridine derivatives, as one of the three ligands. The imine-N containing heterocycles include, but are not limited to, nicotinic acid (NIC), isonicotinic acid (ISONIC), 4-pyridineacetic acid (PA), 4-pyridineethylsulfonic acid (PES), and 3-pyridinesulfonic acid (PSA). Like water-soluble phosphines, the imine-N containing heterocycles in this disclosure also form ternary ligand $^{99m}$Tc complexes, [$^{99m}$Tc(HYNIC-BM)(tricine)(L)] (L=an imine-N containing heterocycle), as equal mixtures of two isomers. The Tc:HYNIC:L:tricine (L=imine-N containing heterocycle) ratio was determined to be 1:1:1:1 through a series of mixed ligand experiments, and has been confirmed by the LC-MS spectral data (Liu, et al., *Bioconjugate Chem.* 1998, 9, 583; Liu, et al., *Bioconjugate Chem.* 2000, 11, 113).

Like that of water-soluble phosphines, the bonding of the imine-N containing coligand to the Tc reduces the number of isomeric forms of [$^{99m}$Tc]HYNIC complexes, and increases the solution stability of $^{99m}$Tc radiopharmaceuticals. Compared to water-soluble phosphines (TPPTS, TPPDS, and TPPMS), these imine-N heterocycles are much smaller so that the impact of the technetium chelate on receptor binding might be minimized. The hydrophilicity of [$^{99m}$Tc]HYNIC complexes can be tuned by changing the substituents on the heterocyclic ring. Neutral imine-N containing heterocyclic coligands are particularly interesting because they form neutral ternary ligand $^{99m}$Tc complexes, which are able to cross the cell membranes and bind to intracellular receptors.

U.S. Pat. No. 6,251,364 discloses novel ternary ligand $^{99m}$Tc complex radiopharmaceuticals comprising highly functionalized pyridine analogues, such as N-(2-hydroxyethyl)isonicotinamide (ISONIC-HE), 1-isonicotinamido-D-sorbitol (ISONIC-Sorb), and isonicotinamido-L-aspartic acid dimethyl ester (ISONIC-Asp-OMe$_2$). The functionalized pyridine coligand is used to control the physicochemical and biodistribution characteristics of the ternary ligand $^{99m}$Tc complexes. The extent of such control is dependent on the degree of functionalization of the pyridine coligand.

ISONIC-Asp-OMe$_2$ is of particular interest because it contains two ester groups, which can be enzymatically hydrolyzed in biological systems. Since ISONIC-Asp-OMe$_2$ carries no charge, it is expected to form neutral technetium complexes, which can cross the cell membrane and potentially bind to intracellular receptors, if the HYNIC-conjugated biomolecule carries no charge. Once inside the cell, enzymatic hydrolysis of these two ester groups will result in formation of negatively charged $^{99m}$Tc-species, which cannot be easily washed out off the cell. In this way, the target uptake may be significantly improved. If ester groups are hydrolyzed in the blood stream, the negatively charged $^{99m}$Tc-species is expected to have faster renal clearance than the neutral precursor. Therefore, the introduction of two enzymatically active ester groups offers two potential advantages: increasing target uptake and decreasing background.

The use of this ternary ligand system offers several advantages. The bonding of phosphine coligand to the Tc dramatically reduces the number of isomeric forms of the [$^{99m}$Tc]HYNIC complexes. The solution stability of [$^{99m}$Tc] HYNIC complexes is dramatically improved. The hydrophilicity of [$^{99m}$Tc]HYNIC complexes can be tuned either by altering the number of sulfonato groups or by using water soluble phosphines with other functionalities. The tricine coligand can also be substituted by other aminocarboxylates, such as dicine (N-bis(hydroxymethyl)methylglycine) and bicine (N,N-bis(hydroxymethyl)glycine). However, the specific activity of [$^{99m}$Tc]HYNIC complexes using bicine as coligands is not as high as that of the corresponding tricine complexes.

In principle, this ternary ligand system is useful for the $^{99m}$Tc-labeling of any HYNIC-conjugated biomolecules. However, problems may arise when they are used for $^{99m}$Tc-labeling of small biomolecules containing one or more disulfide linkages, which are often vital to keep the rigid cyclic conformation of the biomolecule and to maintain the high receptor binding affinity. The use of a large amount of water-soluble phosphine coligand, such as TPPTS, in combination with high temperature heating, which is needed for high-yield radiolabeling of hydrazone-protected HYNIC-conjugates, may destroy the S-S disulfide bonds and cause adverse effect on the biological properties of the $^{99m}$Tc-labeled HYNIC conjugate.

Therefore, there is a continuing need for new ligand systems, which can be used for the $^{99m}$Tc-labeling of small biomolecules (peptides or nonpeptide receptor ligands, enzyme inhibitors, or enzyme substrates) with high labeling efficiency, and that form $^{99m}$Tc complexes with high stability and minimal isomerism. This invention is directed towards meeting this and other important needs.

SUMMARY OF THE INVENTION

This invention is directed to chelants and macrocyclic metal complexes thereof, methods of preparing the chelants and macrocyclic metal complexes, and radiopharmaceutical compositions comprising the macrocyclic metal complexes. This invention is particularly directed to the use of the macrocyclic metal complexes as radiopharmaceuticals for the diagnosis of cardiovascular disorders, infectious diseases and cancer. This invention is also directed to the use of new chelants as bifunctional chelators (BFCs) for the radiolabeling of target-specific biomolecules, such as proteins, peptides, peptidomimetics, non-peptide receptor ligands, enzyme inhibitors, and enzyme substrates. This invention is particularly directed to the use of macrocyclic metal complexes containing the chelant-biomolecule conjugates as target-specific diagnostic radiopharmaceuticals that selectively localize at sites of disease and thus allow an image to be obtained of the loci using gamma scintigraphy. This invention is further directed to methods of use of the radiopharmaceuticals as imaging agents for the diagnosis of cardiovascular disorders such as thromboembolic disease or atherosclerosis, infectious disease and cancer.

In one embodiment, the invention is directed to compounds of Formula I, which are useful as chelants:

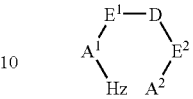

I or a pharmaceutically acceptable salt thereof, wherein:
$E^1$ and $E^2$ are independently selected at each occurrence from: a direct bond, $CH_2$, $C(O)$, $C(S)$, $C(O)NH$, $C(S)NH$, $NHC(O)$, $NHC(S)$, $NHC(O)NH$, $NHC(S)NH$, $SO_2$, and $SO_2NH$;

Hz is the free hydrazine moiety or a hydrazone of the formula $-N(R^1)N=C(R^2)(R^3)$;

$R^1$ is selected from: H, $C_1$-$C_{10}$ alkyl substituted with 0-5 $R^4$, $C_2$-$C_{10}$ alkenyl substituted with 0-5 $R^4$, $C_6$-$C_{10}$ aryl substituted with 0-3 $R^4$, and $C_4$-$C_{10}$ heteroaryl substituted with 0-3 $R^4$;

$R^2$ and $R^3$ are independently selected at each occurrence from: H, CN, $CO_2R^5$, $C(O)R^5$, $C(O)N(R^5)_2$, $C_1$-$C_{10}$ alkyl substituted with 0-5 $R^5$, $C_2$-$C_{10}$ alkenyl substitute with 0-5 $R^5$, $C_3$-$C_{10}$ cycloalkyl substituted with 0-5 $R^5$, $C_6$-$C_{10}$ aryl substituted with 0-3 $R^5$, and $C_4$-$C_{10}$ heteroaryl substituted with 0-3 $R^5$; or alternatively $R^2$ and $R^3$ may be taken together to form a $C_3$-$C_{10}$ cycloalkyl or $C_5$-$C_{10}$ cycloalkenyl;

$R^4$ is independently selected at each occurrence from: OH, COOH, $C(O)NH_2$, $SO_3H$, and $SO_2NH_2$;

$R^5$ is independently selected at each occurrence from: $C(=O)OR^6$, $C(O)NHR^6$, $C(=O)R^6$, $NHR^6$, $NHC(=O)R^6$, $NHC(=O)NHR^6$, $NHC(=S)NHR^6$, $OR^6$, $OC(=O)R^6$, $OC(=O)OR^6$, $PO(OR^6)_2$, $SR^6$, $SOR^6$, $SO_2R^6$, $SO_3R^6$, and $SO_2NHR^6$;

$R^6$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;

$A^1$ is selected from: $C_6$-$C_{10}$ arylenyl substituted with 0-2 $R^7$, and $C_4$-$C_{10}$ heteroarylenyl substituted with 0-2 $R^7$;

$A^2$ is a functionalized imine-N containing $C_3$-$C_{10}$ heterocycle substituted with 0-2 $R^7$;

$R^7$ is independently selected at each occurrence from: $C(=O)OR^8$, $C(O)NHR^8$, $C(=O)R^8$, $NHR^8$, $NHC(=O)R^8$, $NHC(=O)NHR^8$, $NHC(=S)NHR^8$, $OR^8$, $OC(=O)R^8$, $OC(=O)OR^8$, $PO(OR^8)_2$, $SR^8$, $SOR^8$, $SO_2R^8$, $SO_3R^8$, and $SO_2NHR^8$;

$R^8$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;

D is a linker of the formula $-[(CHR^9)_f(CHR^{10})_gZ(CHR^{11})_h(CHR^{12})_i]_j-$, f is independently an integer from 0 to 5;
g is independently an integer from 0 to 5;
h is independently an integer from 0 to 5;
i is independently an integer from 0 to 5;
j is independently an integer from 1 to 5;

$R^9$, $R^{10}$, $R^{11}$ and $R^{12}$ are independently selected at each occurrence from: H, $R^{13}$, $C_1$-$C_{10}$ alkyl substituted with 0-5 $R^{13}$, $C_2$-$C_{10}$ alkenyl substituted with 0-5 $R^{13}$, $C_3$-$C_{10}$ cycloalkyl substituted with 0-5 $R^{13}$, $C_6$-$C_{10}$ aryl substituted with 0-3 $R^{13}$, $C_4$-$C_{10}$ heteroaryl substituted with 0-3 $R^{13}$;

alternatively $R^9$ and $R^{10}$, $R^9$ and $R^{11}$, $R^9$ and $R^{12}$, $R^{10}$ and $R^{11}$, $R^{10}$ and $R^{12}$ or $R^{11}$ and $R^{12}$, may be taken together to form a $C_3$-$C_{10}$ cycloalkyl or $C_5$-$C_{10}$ cycloalkenyl;

$R^{13}$ is independently selected at each occurrence from: $C(=O)OR^{14}$, $C(O)NHR^{14}$, $C(=O)R^{14}$, $NHR^{14}$, $NHC(=O)R^{14}$, $NHC(=O)NHR^{14}$, $NHC(=S)NHR^{14}$, $OR^{14}$, $OC(=O)R^{14}$, $OC(=O)OR^{14}$, $PO(OR^{14})_2$, $SR^{14}$, $SOR^{14}$, $SO_2R^{14}$, $SO_3R^{14}$, and $SO_2NHR^{14}$;

$R^{14}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;

Z is independently selected at each occurrence from: a bond, $CH_2$, $C(O)$, $C(O)NR^{15}$, $C(S)NR^{15}$, $NR^{16}$, $NR^{15}C(O)$, $NR^{15}C(S)$, $NHC(=NH)NH$, $NHC(O)NH$, $NHC(S)NH$, $NR^{15}SO_2$, O, S, SO, $SO_2$, and $SO_2NR^{15}$;

$R^{15}$ is independently selected at each occurrence from: H, $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$ and $C_4$-$C_{10}$ heteroaryl substituted with 0-3 $R^{17}$;

$R^{16}$ is independently selected at each occurrence from: H, $R^{18}$, $C(O)R^{18}$, $SO_2R^{18}$, and $C(O)N(R^{18})$;

$R^{17}$ is independently selected at each occurrence from: OH, $C(=O)OR^{19}$, $C(O)NHR^{19}$, $C(=O)R^{19}$, $NHR^{19}$, $NHC(=O)R^{19}$, $NHC(=O)NHR^{19}$, $NHC(=S)NHR^{19}$, $OR^{19}$, $OC(=O)R^{19}$, $OC(=O)OR^{19}$, $PO(OR^{19})_2$, $SO_2R^{19}$, $SO_3R^{19}$, and $SO_2NHR^{19}$;

$R^{18}$ is independently selected at each occurrence from: $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$, and $C_4$-$C_{10}$ heteroaryl substituted with 0-3 $R^{17}$; and $R^{19}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl.

In another embodiment, the invention is directed to macrocyclic metal complexes of Formula II:

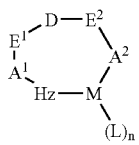

II or a pharmaceutically acceptable salt thereof, wherein

M is a transition metal radionuclide selected from: $^{99m}Tc$, $^{186}Re$ and $^{188}Re$;

L is a coligand capable of stabilizing the macrocyclic metal complex, and is a dioxygen chelating agent, functionalized pyridinecarboxylate, or functionalized aminocarboxylate;

n is 1 or 2;

$E^1$ and $E^2$ are independently selected at each occurrence from: a direct bond, $CH_2$, $C(O)$, $C(S)$, $C(O)NH$, $C(S)NH$, $NHC(O)$, $NHC(S)$, $NHC(O)NH$, $NHC(S)NH$, $SO_2$, and $SO_2NH$;

Hz is a hydrazino or diazenido group of formula —$N(R^1)N$=;

$R^1$ is selected from: a lone pair of electrons, a bond between the two nitrogen atoms, H, $C_1$-$C_{10}$ alkyl substituted with 0-5 $R^4$, $C_2$-$C_{10}$ alkenyl substituted with 0-5 $R^4$, $C_6$-$C_{10}$ aryl substituted with 0-3 $R^4$, and $C_4$-$C_{10}$ heteroaryl substituted with 0-3 $R^4$;

$R^4$ is independently selected at each occurrence from: OH, COOH, $C(O)NH_2$, $SO_3H$, and $SO_2NH_2$;

$A^1$ is selected from: $C_6$-$C_{10}$ arylenyl substituted with 0-2 $R^7$, and $C_4$-$C_{10}$ heteroarylenyl substituted with 0-2 $R^7$;

$A^2$ is a functionalized imine-N containing $C_3$-$C_{10}$ heterocycle substituted with 0-2 $R^7$;

$R^7$ is independently selected at each occurrence from: $C(=O)OR^8$, $C(O)NHR^8$, $C(=O)R^8$, $NHR^8$, $NHC(=O)R^8$, $NHC(=O)NHR^8$, $NHC(=S)NHR^8$, $OR^8$, $OC(=O)R^8$, $OC(=O)OR^8$, $PO(OR^8)_2$, $SR^8$, $SOR^8$, $SO_2R^8$, $SO_3R^8$, and $SO_2NHR^8$;

$R^8$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;

D is a linker of the formula —$[(CHR^9)_f(CHR^{10})_gZ(CHR^{11})_h(CHR^{12})_i]_j$—, f is independently an integer from 0 to 5;

g is independently an integer from 0 to 5;

h is independently an integer from 0 to 5;

i is independently an integer from 0 to 5;

j is independently an integer from 1 to 5;

$R^9$, $R^{10}$, $R^{11}$ and $R^{12}$ are independently selected at each occurrence from: H, $R^{13}$, $C_1$-$C_{10}$ alkyl substituted with 0-5 $R^{13}$, $C_2$-$C_{10}$ alkenyl substituted with 0-5 $R^{13}$, $C_3$-$C_{10}$ cycloalkyl substituted with 0-5 $R^{13}$, $C_6$-$C_{10}$ aryl substituted with 0-3 $R^{13}$, and $C_4$-$C_{10}$ heteroaryl substituted with 0-3 $R^{13}$;

alternatively $R^9$ and $R^{10}$, $R^9$ and $R^{11}$, $R^9$ and $R^{12}$, $R^{10}$ and $R^{11}$, $R^{10}$ and $R^{12}$ or $R^{11}$ and $R^{12}$, may be taken together to form a $C_3$-$C_{10}$ cycloalkyl or $C_5$-$C_{10}$ cycloalkenyl;

$R^{13}$ is independently selected at each occurrence from: $C(=O)OR^{14}$, $C(O)NHR^{14}$, $C(=O)R^{14}$, $NHR^{14}$, $NHC(=O)R^{14}$, $NHC(=O)NHR^{14}$, $NHC(=S)NHR^{14}$, $OR^{14}$, $OC(=O)R^{14}$, $OC(=O)OR^{14}$, $PO(OR^{14})_2$, $SR^{14}$, $SOR^{14}$, $SO_2R^{14}$, $SO_3R^{14}$, and $SO_2NHR^{14}$;

$R^{14}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;

Z is independently selected at each occurrence from: a bond, $CH_2$, $C(O)$, $C(O)NR^{15}$, $C(S)NR^{15}$, $NR^{16}$, $NR^{15}C(O)$, $NR^{15}C(S)$, $NHC(=NH)NH$, $NHC(O)NH$, $NHC(S)NH$, $NR^{15}SO_2$, O, S, SO, $SO_2$, and $SO_2NR^{15}$;

$R^{15}$ is independently selected at each occurrence from: H, $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$ and $C_4$-$C_{10}$ heteroaryl substituted with 0-3 $R^{17}$;

$R^{16}$ is independently selected at each occurrence from: H, $R^{18}$, $C(O)R^{18}$, $SO_2R^{15}$, and $C(O)N(R^{18})$;

$R^{17}$ is independently selected at each occurrence from: OH, $C(=O)OR^{19}$, $C(O)NHR^{19}$, $C(=O)R^{19}$, $NHR^{19}$, $NHC(=O)R^{19}$, $NHC(=O)NHR^{19}$, $NHC(=S)NHR^{19}$, $OR^{19}$, $OC(=O)R^{19}$, $OC(=O)OR^{19}$, $PO(OR^{19})_2$, $SO_2R^{19}$, $SO_3R^{19}$, and $SO_2NHR^{19}$;

$R^{18}$ is independently selected at each occurrence from: $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$, and $C_4$-$C_{10}$ heteroaryl substituted with 0-3 $R^{17}$; and $R^{19}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl.

In another embodiment, the invention is directed to radiopharmaceutical compositions, comprising said macrocyclic metal complex of Formula II.

In yet other embodiments, the invention is directed to kits for forming a macrocyclic metal complex radiopharmaceutical, comprising:

a compound of Formula I;

a coligand selected from the group: dioxygen chelating agent, functionalized pyridinecarboxylate, and functionalized aminocarboxylate, preferably tricine;

a reducing agent, preferably stannous chloride; and instructions for contacting said compound, said coligand and said reducing agent with a radionuclide, preferably

[$^{99m}$Tc]pertechnetate, under conditions sufficient to produce said macrocyclic metal complex radiopharmaceutical.

In yet other embodiments, the invention is directed to kits for forming a macrocyclic metal complex radiopharmaceutical, comprising:
 a predetermined quantity of a sterile, pharmaceutically-acceptable compound of Formula I;
 a predetermined quantity of sterile, pharmaceutically-acceptable stabilizing coligand selected from the group: a dioxygen chelating agent and a functionalized aminocarboxylate, preferably tricine;
 a predetermined quantity of a sterile, pharmaceutically-acceptable reducing agent, preferably stannous chloride; and
 optionally, a predetermined quantity of one or more sterile, pharmaceutically acceptable components selected from the group: buffers, lyophilization aids, stabilization aids, solubilization aids and bacteriostats.

Yet other embodiments are directed to diagnostic compositions, comprising:
 a diagnostically-effective amount of the macrocyclic metal complex according to Formula II; and
 a pharmaceutically acceptable carrier.

Other embodiments are directed to methods for radioimaging a patient, comprising the steps of:
 administering to said patient an effective amount of said macrocyclic metal complex of Formula II; and
 scanning said patient using a radioimaging device.

In further embodiments, the invention is directed to conjugates of Formula III:

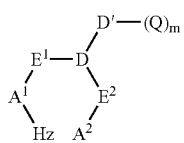

III or a pharmaceutically acceptable salt thereof, wherein
 $E^1$ and $E^2$ are independently selected at each occurrence from: a direct bond, $CH_2$, $C(O)$, $C(S)$, $C(O)NH$, $C(S)NH$, $NHC(O)$, $NHC(S)$, $NHC(O)NH$, $NHC(S)NH$, $SO_2$, and $SO_2NH$;
 Hz is the free hydrazine moiety or a hydrazone of the formula $-N(R^1)N=C(R^2)(R^3)$,
 $R^1$ is selected from: H, $C_1$-$C_{10}$ alkyl substituted with 0-5 $R^4$, $C_2$-$C_{10}$ alkenyl substituted with 0-5 $R^4$, $C_6$-$C_{10}$ aryl substituted with 0-3 $R^4$, and $C_4$-$C_{10}$ heteroaryl substituted with 0-3 $R^4$;
 $R^2$ and $R^3$ are independently selected from: H, CN, $CO_2R^5$, $C(O)R^5$, $C(O)N(R^5)_2$, $C_1$-$C_{10}$ alkyl substituted with 0-5 $R^5$, $C_2$-$C_{10}$ alkenyl substituted with 0-5 $R^5$, $C_3$-$C_{10}$ cycloalkyl substituted with 0-5 $R^5$, $C_6$-$C_{10}$ aryl substituted with 0-3 $R^5$, and $C_4$-$C_{10}$ heteroaryl substituted with 0-3 $R^5$; or alternatively $R^2$ and $R^3$ may be taken together to form a $C_3$-$C_{10}$ cycloalkyl or $C_5$-$C_{10}$ cycloalkenyl;
 $R^4$ is independently selected at each occurrence from: OH, COOH, $C(O)NH_2$, $SO_3H$, and $SO_2NH_2$;
 $R^5$ is independently selected at each occurrence from: $C(=O)OR^6$, $C(O)NHR^6$, $C(=O)R^6$, $NHR^6$, $NHC(=O)R^6$, $NHC(=O)NHR^6$, $NHC(=S)NHR^6$, $OR^6$, $OC(=O)R^6$, $OC(=O)OR^6$, $PO(OR^6)_2$, $SR^6$, $SOR^6$, $SO_2R^6$, $SO_3R^6$, and $SO_2NHR^6$;
 $R^6$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
 $A^1$ is selected from: $C_6$-$C_{10}$ arylenyl substituted with 0-2 $R^7$, and $C_4$-$C_{10}$ heteroarylenyl substituted with 0-2 $R^7$;
 $A^2$ is a functionalized imine-N containing $C_3$-$C_{10}$ heterocycle substituted with 0-2 $R^7$;
 $R^7$ is independently selected at each occurrence from: $C(=O)OR^8$, $C(O)NHR^8$, $C(=O)R^8$, $NHR^8$, $NHC(=O)R^8$, $NHC(=O)NHR^8$, $NHC(=S)NHR^8$, $OR^8$, $OC(=O)R^8$, $OC(=O)OR^8$, $PO(OR^8)_2$, $SR^8$, $SOR^8$, $SO_2R^8$, $SO_3R^8$, and $SO_2NHR^8$;
 $R^8$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
 D is a linker of the formula $-[(CHR^9)_f(CHR^{10})_gZ(CHR^{11})_h(CHR^{12})_i]_{j'}-$,
 f is independently an integer from 0 to 5;
 g is independently an integer from 0 to 5;
 h is independently an integer from 0 to 5;
 i is independently an integer from 0 to 5;
 j is independently an integer from 1 to 5;
 $R^9$, $R^{10}$, $R^{11}$ and $R^{12}$ are independently selected at each occurrence from: H, $R^{13}$, $C_1$-$C_{10}$ alkyl substituted with 0-5 $R^{13}$;, $C_2$-$C_{10}$ alkenyl substituted with 0-5 $R^{13}$, $C_3$-$C_{10}$ cycloalkyl substituted with 0-5 $R^{13}$, $C_6$-$C_{10}$ aryl substituted with 0-3 $R^{13}$, $C_4$-$C_{10}$ heteroaryl substituted with 0-3 $R^{13}$;
 alternatively $R^9$ and $R^{10}$, $R^9$ and $R^{11}$, $R^9$ and $R^{12}$, $R^{10}$ and $R^{11}$, $R^{10}$ and $R^{12}$ or $R^{11}$ and $R^{12}$, may be taken together to form a $C_3$-$C_{10}$ cycloalkyl or $C_5$-$C_{10}$ cycloalkenyl;
 $R^{13}$ is independently selected at each occurrence from: $C(=O)OR^{14}$, $C(O)NHR^{14}$, $C(=O)R^{14}$, $NHR^{14}$, $NHC(=O)R^{14}$, $NHC(=O)NHR^{14}$, $NHC(=S)NHR^{14}$, $OR^{14}$, $OC(=O)R^{14}$, $OC(=O)OR^{14}$, $PO(OR^{14})_2$, $SR^{14}$, $SOR^{14}$, $SO_2R^4$, $SO_3R^{14}$, and $SO_2NHR^{14}$;
 $R^{14}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
 Z is independently selected at each occurrence from: a bond, $CH_2$, $C(O)$, $C(O)NR^{15}$, $C(S)NR^{15}$, $NR^{16}$, $NR^{15}C(O)$, $NR^{15}C(S)$, $NHC(=NH)NH$, $NHC(O)NH$, $NHC(S)NH$, $NR^{15}SO_2$, O, S, SO, $SO_2$, and $SO_2NR^{15}$;
 $R^{15}$ is independently selected at each occurrence from: H, $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$ and $C_4$-$C_{10}$ heteroaryl substituted with 0-3 $R^{17}$;
 $R^{16}$ is independently selected at each occurrence from: H, $R^{18}$, $C(O)R^{18}$, $SO_2R^{18}$, and $C(O)N(R^{18})$;
 $R^{17}$ is independently selected at each occurrence from: OH, $C(=O)OR^{19}$, $C(O)NHR^{19}$, $C(=O)R^{19}$, $NHR^{19}$, $NHC(=O)R^{19}$, $NHC(=O)NHR^{19}$, $NHC(=S)NHR^{19}$, $OR^{19}$, $OC(=O)R^{19}$, $OC(=O)OR^{19}$, $PO(OR^{19})_2$, $SO_2R^{19}$, $SO_3R^{19}$, and $SO_2NHR^{19}$;
 $R^{18}$ is independently selected at each occurrence from: $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$, and $C_4$-$C_{10}$ heteroaryl substituted with 0-3 $R^{17}$;
 $R^{19}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
 Q is a biologically active group;
 m is an integer of 1 to 20;
 D' is a pharmacokinetic modifier having the formula:

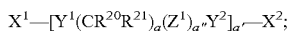

$X^1$ is $[(CH_2)_bZ^1]_{b'}-(CR^{20}R^{21})_{b''}$;
 $X^2$ is $(CR^{20}R^{21})_{b''}-[Z^1(CH_2)_b]_{b'}$;

a is independently an integer of 0 to 10;
a' is independently an integer of 0 to 10;
a" independently an integer of 0 to 1;
b is independently an integer of 0 to 10;
b' independently an integer of 0 to 1;
b" is independently an integer of 0 to 10;
$Y^1$ and $Y^2$, at each occurrence, are independently selected from: a bond, O, $NR^{21}$, C=O, C(=O)O, OC(=O)O, C(=O)NH—, C=$NR^{21}$, S, SO, $SO_2$, $SO_3$, NHC(=O), $(NH)_2C(=O)$, and $(NH)_2C=S$;
$Z^1$ is independently selected at each occurrence from: $C_6$-$C_{14}$ saturated, partially saturated, or aromatic carbocyclic ring system, substituted with 0-4 $R^{22}$; and a heterocyclic ring system, optionally substituted with 0-4 $R^{22}$;
$R^{20}$ and $R^{21}$ are independently selected at each occurrence from: H, $C_1$-$C_{10}$ alkyl substituted with 0-5 $R^{23}$, and aryl substituted with 0-5 $R^{23}$;
$R^{22}$ and $R^{23}$ are independently selected at each occurrence from the group: OH, $NHR^{24}$, C(=O)$R^{24}$, OC(=O)$R^{24}$, OC(=O)O$R^{24}$, C(=O)O$R^{24}$, C(=O)$NR^{24}$, —CN, $SR^{24}$, $SOR^{24}$, $SO_2R^{24}$, NHC(=O)$R^{24}$, NHC(=O)$NHR^{24}$, and NHC(=S)$NHR^{24}$;
alternatively, when m is greater than 1, $R^{23}$ is independently selected at each occurrence from the group: O, $NR^{24}$, C=O, C(=O)O, OC(=O)O, C(=O)N, C=$NR^{24}$, S, SO, $SO_2$, $SO_3$, NHC(=O), $(NH)_2C(=O)$, and $(NH)_2C=S$; and
$R^{24}$ is independently selected at each occurrence from the group: H, $C_1$-$C_6$ alkyl, benzyl, and phenyl.

In yet further embodiments, the invention is directed to macrocyclic metal complex-conjugates of Formula IV:

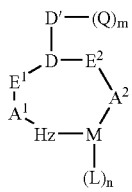

IV or a pharmaceutically acceptable salt thereof, wherein
M is a transition metal radionuclide selected from: $^{99m}$Tc, $^{186}$Re and $^{188}$Re;
L is a coligand capable of stabilizing the macrocyclic metal complex, and is a dioxygen chelating agent, functionalized pyridinecarboxylate, or functionalized aminocarboxylate;
n is 1 or 2;
$E^1$ and $E^2$ are independently selected at each occurrence from: a direct bond, $CH_2$, C(O), C(S), C(O)NH, C(S)NH, NHC(O), NHC(S), NHC(O)NH, NHC(S)NH, $SO_2$, and $SO_2NH$;
Hz is a hydrazino or diazenido group of formula —N($R^1$)N=;
$R^1$ is selected from: a lone pair of electrons, a bond between the two nitrogen atoms, H, $C_1$-$C_{10}$ alkyl substituted with 0-5 $R^4$, $C_2$-$C_{10}$ alkenyl substituted with 0-5 $R^4$, $C_6$-$C_{10}$ aryl substituted with 0-3 $R^4$, and $C_4$-$C_{10}$ heteroaryl substituted with 0-3 $R^4$;
$R^2$ and $R^3$ are independently selected at each occurrence from: H, CN, $CO_2R^5$, C(O)$R^5$, C(O)N($R^5$)$_2$, $C_1$-$C_{10}$ alkyl substituted with 0-5 $R^5$, $C_2$-$C_{10}$ alkenyl substituted with 0-5 $R^5$, $C_3$-$C_{10}$ cycloalkyl substituted with 0-5 $R^5$, $C_6$-$C_{10}$ aryl substituted with 0-3 $R^5$, and $C_4$-$C_{10}$ heteroaryl substituted with 0-3 $R^5$; or alternatively $R^2$ and $R^3$ may be taken together to form a $C_3$-$C_{10}$ cycloalkyl or $C_5$-$C_{10}$ cycloalkenyl;
$R^4$ is independently selected at each occurrence from: OH, COOH, C(O)$NH_2$, $SO_3H$, and $SO_2NH_2$;
$R^5$ is independently selected at each occurrence from: C(=O)O$R^6$, C(O)$NHR^6$, C(=O)$R^6$, $NHR^6$, NHC(=O)$R^6$, NHC(=O)$NHR^6$, NHC(=S)$NHR^6$, $OR^6$, OC(=O)$R^6$, OC(=O)O$R^6$, PO(O$R^6$)$_2$, $SR^6$, $SOR^6$, $SO_2R^6$, $SO_3R^6$, and $SO_2NHR^6$;
$R^6$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
$A^1$ is selected from: $C_6$-$C_{10}$ arylenyl substituted with 0-2 $R^7$, and $C_4$-$C_{10}$ heteroarylenyl substituted with 0-2 $R^7$;
$A^2$ is a functionalized imine-N containing $C_3$-$C_{10}$ heterocycle substituted with 0-2$R^7$;
$R^7$ is independently selected at each occurrence from: C(=O)O$R^8$, C(O)$NHR^8$, C(=O)$R^8$, $NHR^8$, NHC(=O)$R^8$, NHC(=O)$NHR^8$, NHC(=S)$NHR^8$, $OR^8$, OC(=O)$R^8$, OC(=O)O$R^8$, PO(O$R^8$)$_2$, $SR^8$, $SOR^8$, $SO_2R^8$, $SO_3R^8$, and $SO_2NHR^8$;
$R^8$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
D is a linker of the formula —[(CHR$^9$)$_f$(CHR$^{10}$)$_g$Z(CHR$^{11}$)$_h$(CHR$^{12}$)$_i$]$_j$—,
f is independently an integer from 0 to 5;
g is independently an integer from 0 to 5;
h is independently an integer from 0 to 5;
i is independently an integer from 0 to 5;
j is independently an integer from 1 to 5;
$R^9$, $R^{10}$, $R^{11}$ and $R^{12}$ are independently selected at each occurrence from: H, $R^{13}$, $C_1$-$C_{10}$ alkyl substituted with 0-5 $R^{13}$, $C_2$-$C_{10}$ alkenyl substituted with 0-5 $R^{13}$, $C_3$-$C_{10}$ cycloalkyl substituted with 0-5 $R^{13}$, $C_6$-$C_{10}$ aryl substituted with 0-3 $R^{13}$, $C_4$-$C_{10}$ heteroaryl substituted with 0-3 $R^{13}$;
alternatively $R^9$ and $R^{10}$, $R^9$ and $R^{11}$, $R^9$ and $R^{12}$, $R^{10}$ and $R^{11}$, $R^{10}$ and $R^{12}$ or $R^{11}$ and $R^{12}$, may be taken together to form a $C_3$-$C_{10}$ cycloalkyl or $C_5$-$C_{10}$ cycloalkenyl;
$R^{13}$ is independently selected at each occurrence from: C(=O)O$R^{14}$; C(O)$NHR^{14}$, C(=O)$R^{14}$, $NHR^{14}$, NHC(=O)$R^{14}$, NHC(=O)$NHR^{14}$, NHC(=S)$NHR^{14}$, $OR^{14}$, OC(=O)$R^{14}$, OC(=O)O$R^{14}$, PO(O$R^{14}$)$_2$, $SR^{14}$, $SOR^{14}$, $SO_2R^{14}$, $SO_3R^{14}$, and $SO_2NHR^{14}$;
$R^{14}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
Z is independently selected at each occurrence from: a bond, $CH_2$, C(O), C(O)$NR^{15}$, C(S)$NR^{15}$, $NR^{16}$, $NR^{15}$C(O), $NR^{15}$C(S), NHC(=NH)NH, NHC(O)NH, NHC(S)NH, $NR^{15}SO_2$, O, S, SO, $SO_2$, and $SO_2NR^{15}$;
$R^{15}$ is independently selected at each occurrence from: H, $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$ and $C_4$-$C_{10}$ heteroaryl substituted with 0-3 $R^{17}$;
$R^{16}$ is independently selected at each occurrence from: H, $R^{18}$, C(O)$R^{18}$, $SO_2R^{18}$, and C(O)N($R^{18}$);
$R^{17}$ is independently selected at each occurrence from: OH, C(=O)O$R^{19}$, C(O)$NHR^{19}$, C(=O)$R^{19}$, $NHR^{19}$, NHC(=O)$R^{19}$, NHC(=O)$NHR^{19}$, NHC(=S)$NHR^{19}$, $OR^{19}$, OC(=O)$R^{19}$, OC(=O)O$R^{19}$, PO(O$R^{19}$)$_2$, $SO_2R^{19}$, $SO_3R^{19}$, and $SO_2NHR^{19}$;
$R^{18}$ is independently selected at each occurrence from: $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$, and $C_4$-$C_{10}$ heteroaryl substituted with 0-3 $R^{17}$;

$R^{19}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;

Q is a biologically active group;

m is an integer of 1 to 20;

D' is a pharmacokinetic modifier having the formula:

$$X^1-[Y^1(CR^{20}R^{21})_a(Z^1)_{a'}Y^2]_{a''}-X^2;$$

$X^1$ is $[(CH_2)_bZ^1]_{b'}$-$(CR^{20}R^{21})_{b''}$;

$X^2$ is $(CR^{20}R^{21})_{b''}$-$[Z^1(CH_2)_b]_{b'}$;

a is independently an integer of 0 to 10;

a' is independently an integer of 0 to 10;

a" independently an integer of 0 to 1;

b is independently an integer of 0 to 10;

b' independently an integer of 0 to 1;

b" is independently an integer of 0 to 10;

$Y^1$ and $Y^2$ at each occurrence, are independently selected from: a bond, O, $NR^{21}$, C=O, C(=O)O, OC(=O)O, C(=O)NH, C=$NR^{21}$, S, SO, $SO_2$, $SO_3$, NHC(=O), $(NH)_2C$(=O), and $(NH)_2C$=S;

$Z^1$ is independently selected at each occurrence from: $C_6$-$C_{14}$ saturated, partially saturated, or aromatic carbocyclic ring system, substituted with 0-4 $R^{22}$; and a heterocyclic ring system, optionally substituted with 0-4 $R^{22}$;

$R^{20}$ and $R^{21}$ are independently selected at each occurrence from: H, $C_1$-$C_{10}$ alkyl substituted with 0-5 $R^{23}$, and aryl is substituted with 0-5 $R^{23}$;

$R^{22}$ and $R^{23}$ are independently selected at each occurrence from the group: OH, $NHR^{24}$, C(=O)$R^{24}$, OC(=O)$R^{24}$, OC(=O)$OR^{24}$, C(=O)$OR^{24}$, C(=O)$NR^{24}$, —CN, $SR^{24}$, $SOR^{24}$, $SO_2R^{24}$, NHC(=O)$R^{24}$, NHC(=O)NH $R^{24}$, and NHC(=S)NH $R^{24}$;

alternatively, when m is greater than 1, $R^{23}$ is independently selected at each occurrence from the group: O, $NR^{24}$, C=O, C(=O)O, OC(=O)O, C(=O)N, C=$NR^{24}$, S, SO, $SO_2$, $SO_3$, NHC(=O), $(NH)_2C$(=O), and $(NH)_2C$=S; and $R^{24}$ is independently selected at each occurrence from the group: H, $C_1$-$C_6$ alkyl, benzyl, and phenyl.

In other embodiments, the invention is directed to radiopharmaceutical compositions, comprising said macrocyclic metal complex-conjugate of Formula IV.

In yet other embodiments, the invention is directed to kits for forming a macrocyclic metal complex radiopharmaceutical, comprising:
- a conjugate of Formula III;
- a coligand selected from the group: dioxygen chelating agent, functionalized pyridinecarboxylate, and functionalized aminocarboxylate, preferably tricine;
- a reducing agent, preferably stannous chloride; and
- instructions for contacting said compound, said coligand and said reducing agent with a radionuclide under conditions sufficient to produce said macrocyclic metal complex radiopharmaceutical.

In another embodiment, the invention is directed to kits for forming a macrocyclic metal complex-conjugate radiopharmaceutical, comprising:
- a predetermined quantity of a sterile, pharmaceutically-acceptable conjugate of Formula III;
- a predetermined quantity of sterile, pharmaceutically-acceptable stabilizing coligand selected from the group: dioxygen chelating agent, functionalized pyridinecarboxylate, and functionalized aminocarboxylate, preferably tricine;
- a predetermined quantity of a sterile, pharmaceutically-acceptable reducing agent, preferably stannous chloride; and
- optionally, a predetermined quantity of one or more sterile, pharmaceutically acceptable components selected from the group: buffers, lyophilization aids, stabilization aids, solubilization aids and bacteriostats.

In other embodiments, the invention is directed to diagnostic compositions, comprising:
- a diagnostically-effective amount of the conjugate of Formula III; and
- a pharmaceutically acceptable carrier.

In further embodiments, the invention is directed to methods for radioimaging a patient, comprising the steps of:
- administering to said patient an effective amount of said conjugate of Formula III; and
- scanning said patient using a radioimaging device.

In further embodiments, the invention is directed to methods for visualizing sites of platelet deposition in a patient by radioimaging, comprising the steps of:
- administering to said patient an effective amount of a conjugate of Formula III; and
- scanning said patient using a radioimaging device;
- wherein Q is a platelet GPIIb/IIIa receptor binder (including agonist or antagonist), preferably IIb/IIIa receptor ligand, or fibrin binding compound (including peptide).

In other embodiments, the invention is directed to methods of determining platelet deposition in a patient, comprising the steps of:
- administering to said patient an effective amount of a conjugate of Formula III; and
- imaging said patient;
- wherein Q is a platelet GPIIb/IIIa receptor binder (including agonist or antagonist), preferably IIb/IIIa receptor ligand, or fibrin binding compound (including peptide).

In another embodiment, the invention is directed to methods of diagnosing a disorder associated with platelet deposition in a patient, comprising the steps of:
- administering to said patient an effective amount of a conjugate of Formula III; and
- imaging said patient;
- wherein Q is a platelet GPIIb/IIIa receptor binder (including agonist or antagonist), preferably IIb/IIIa receptor ligand, or fibrin binding compound (including peptide).

In yet another embodiment, the invention is directed to methods of diagnosing thromboembolic disorders or atherosclerosis in a patient, comprising the steps of:
- administering to said patient an effective amount of a conjugate of Formula III; and
- generating a radioimage of at least a part of said patient's body;
- wherein Q is a platelet GPIIb/IIIa receptor binder (including agonist or antagonist), preferably IIb/IIIa receptor ligand, or fibrin binding compound (including peptide).

In other embodiments, the invention is directed to methods of diagnosing infection, inflammation or transplant rejection in a patient, comprising the steps of:
- administering to said patient an effective amount of a conjugate of Formula III; and
- generating a radioimage of at least a part of said patient's body;
- wherein Q is selected from the group consisting of a leukocyte binding compound (including peptide), a chemotactic compound (including peptide), and a $LTB_4$ receptor binder (including agonist and antagonist).

In yet other embodiments, the invention is directed to methods detecting new angiogenic vasculature in a patient, comprising the steps of:
- administering to said patient an effective amount of a conjugate of Formula III; and
- generating a radioimage of at least a part of said patient's body;

wherein Q is a vitronectin receptor binder (including agonist and antagonist), a somatostatin analog, or a growth factor receptor binder (including agonist and antagonist).

DETAILED DESCRIPTION OF THE INVENTION

This invention is directed to chelants and macrocyclic metal complexes thereof, methods of preparing the chelants and macrocyclic metal complexes, and radiopharmaceutical compositions comprising the macrocyclic metal complexes. This invention is particularly directed to the use of the macrocyclic metal complexes as radiopharmaceuticals for the diagnosis of cardiovascular disorders, infectious diseases and cancer. This invention is also directed to the use of new chelants as bifunctional chelators (BFCs) for the radiolabeling of target-specific biomolecules, such as proteins, peptides, peptidomimetics, non-peptide receptor ligands, enzyme inhibitors, and enzyme substrates. This invention is particularly directed to the use of macrocyclic metal complexes containing the chelant-biomolecule conjugates as target-specific diagnostic radiopharmaceuticals that selectively localize at sites of disease and thus allow an image to be obtained of the loci using gamma scintigraphy. This invention is further directed to methods of use of the radiopharmaceuticals as imaging agents for the diagnosis of cardiovascular disorders such as thromboembolic disease or atherosclerosis, infectious disease and cancer.

In a first aspect, the chelant is a compound of the Formula I:

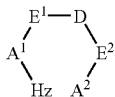

I or a pharmaceutically acceptable salt thereof, wherein:
$E^1$ and $E^2$ are independently selected at each occurrence from: a direct bond, $CH_2$, C(O), C(S), C(O)NH, C(S)NH, NHC(O), NHC(S), NHC(O)NH, NHC(S)NH, $SO_2$, and $SO_2NH$;

Hz is the free hydrazine moiety or a hydrazone of the formula $—N(R^1)N=C(R^2)(R^3)$;

$R^1$ is selected from: H, $C_1$-$C_{10}$ alkyl substituted with 0-5 $R^4$, $C_2$-$C_{10}$ alkenyl substituted with 0-5 $R^4$, $C_6$-$C_{10}$ aryl substituted with 0-3 $R^4$, and $C_4$-$C_{10}$ heteroaryl substituted with 0-3 $R^4$;

$R^2$ and $R^3$ are independently selected at each occurrence from: H, CN, $CO_2R^5$, $C(O)R^5$, $C(O)N(R^5)_2$, $C_1$-$C_{10}$ alkyl substituted with 0-5 $R^5$, $C_2$-$C_{10}$ alkenyl substituted with 0-5 $R^5$, $C_3$-$C_{10}$ cycloalkyl substituted with 0-5 $R^5$, $C_6$-$C_{10}$ aryl substituted with 0-3 $R^5$, and $C_4$-$C_{10}$ heteroaryl substituted with 0-3 $R^5$; or alternatively $R^2$ and $R^3$ may be taken together to form a $C_3$-$C_{10}$ cycloalkyl or $C_5$-$C_{10}$ cycloalkenyl;

$R^4$ is independently selected at each occurrence from: OH, COOH, $C(O)NH_2$, $SO_3H$, and $SO_2NH_2$;

$R^5$ is independently selected at each occurrence from: $C(=O)OR^6$, $C(O)NHR^6$, $C(=O)R^6$, $NHR^6$, $NHC(=O)R^6$, $NHC(=O)NHR^6$, $NHC(=S)NHR^6$, $OR^6$, $OC(=O)R^6$, $OC(=O)OR^6$, $PO(OR^6)_2$, $SR^6$, $SOR^6$, $SO_2R^6$, $SO_3R^6$, and $SO_2NHR^6$;

$R^6$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;

$A^1$ is selected from: $C_6$-$C_{10}$ arylenyl substituted with 0-2 $R^7$, and $C_4$-$C_{10}$ heteroarylenyl substituted with 0-2 $R^7$;

$A^2$ is a functionalized imine-N containing $C_3$-$C_{10}$ heterocycle substituted with 0-2 $R^7$;

$R^7$ is independently selected at each occurrence from: $C(=O)OR^8$, $C(O)NHR^8$, $C(=O)R^8$, $NHR^8$, $NHC(=O)R^8$, $NHC(=O)NHR^8$, $NHC(=S)NHR^8$, $OR^8$, $OC(=O)R^8$, $OC(=O)OR^8$, $PO(OR^8)_2$, $SR^8$, $SOR^8$, $SO_2R^8$, $SO_3R^8$, and $SO_2NHR^8$;

$R^8$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;

D is a linker of the formula $—[(CHR^9)_f(CHR^{10})_gZ(CHR^{11})_h(CHR^{12})_i]_j—$, f is independently an integer from 0 to 5;
g is independently an integer from 0 to 5;
h is independently an integer from 0 to 5;
i is independently an integer from 0 to 5;
j is independently an integer from 1 to 5;

$R^9$, $R^{10}$, $R^{11}$ and $R^{12}$ are independently selected at each occurrence from: H, $R^{13}$, $C_1$-$C_{10}$ alkyl substituted with 0-5 $R^{13}$, $C_2$-$C_{10}$ alkenyl substituted with 0-5 $R^{13}$, $C_3$-$C_{10}$ cycloalkyl substituted with 0-5 $R^{13}$, $C_6$-$C_{10}$ aryl substituted with 0-3 $R^{13}$, $C_4$-$C_{10}$ heteroaryl substituted with 0-3 $R^{13}$;

alternatively $R^9$ and $R^{10}$, $R^9$ and $R^{11}$, $R^9$ and $R^{12}$, $R^{10}$ and $R^{11}$, $R^{10}$ and $R^{12}$ or $R^{11}$ and $R^{12}$, may be taken together to form a $C_3$-$C_{10}$ cycloalkyl or $C_5$-$C_{10}$ cycloalkenyl;

$R^{13}$ is independently selected at each occurrence from: $C(=O)OR^{14}$, $C(O)NHR^{14}$, $C(=O)R^{14}$, $NHR^{14}$, $NHC(=O)R^{14}$, $NHC(=O)NHR^{14}$, $NHC(=S)NHR^{14}$, $OR^{14}$, $OC(=O)R^{14}$, $OC(=O)OR^{14}$, $PO(OR^{14})_2$, $SR^{14}$, $SOR^{14}$, $SO_2R^{14}$, $SO_3R^{14}$, and $SO_2NHR^{14}$;

$R^{14}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;

Z is independently selected at each occurrence from: a bond, $CH_2$, C(O), $C(O)NR^{15}$, $C(S)NR^{15}$, $NR^{16}$, $NR^{15}C(O)$, $NR^{15}C(S)$, $NHC(=NH)NH$, NHC(O)NH, NHC(S)NH, $NR^{15}SO_2$, O, S, SO, $SO_2$, and $SO_2NR^{15}$;

$R^{15}$ is independently selected at each occurrence from: H, $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$ and $C_4$-$C_{10}$ heteroaryl substituted with 0-3 $R^{17}$;

$R^{16}$ is independently selected at each occurrence from: H, $R^{18}$, $C(O)R^{18}$, $SO_2R^{18}$, and $C(O)N(R^{18})$;

$R^{17}$ is independently selected at each occurrence from: OH, $C(=O)OR^{19}$, $C(O)NHR^{19}$, $C(=O)R^{19}$, $NHR^{19}$, $NHC(=O)R^{19}$, $NHC(=O)NHR^{19}$, $NHC(=S)NHR^{19}$, $OR^{19}$, $OC(=O)R^{19}$, $OC(=O)OR^{19}$, $PO(OR^{19})_2$, $SO_2R^{19}$, $SO_3R^{19}$, and $SO_2NHR^{19}$;

$R^{18}$ is independently selected at each occurrence from: $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$, and $C_4$-$C_{10}$ heteroaryl substituted with 0-3 $R^{17}$; and $R^{19}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl.

In preferred compounds of Formula I:
$E^1$ and $E^2$ are independently selected at each occurrence from: C(O)NH, NHC(O), NHC(O)NH, NHC(S)NH, and $SO_2NH$;

$R^1$ is selected from: H, $C_1$-$C_{10}$ alkyl substituted with 0-3 $R^4$, $C_2$-$C_{10}$ alkenyl substituted with 0-3 $R^4$, $C_6$-$C_{10}$ aryl substituted with 0-2 $R^4$, and $C_4$-$C_{10}$ heteroaryl substituted with 0-2 $R^4$;

$R^2$ and $R^3$ are independently selected at each occurrence from: H, $C_6$-$C_{10}$ aryl substituted with 0-2 $R^5$, and $C_4$-$C_{10}$ heteroaryl substituted with 0-2 $R^5$;

$R^4$ is independently selected at each occurrence from: OH, COOH, and $SO_3H$;

$R^5$ is independently selected at each occurrence from: C(=O)OH, C(O)$NHR^6$, $NHR^6$, NHC(=O)$R^6$, NHC(=S)$NHR^6$, $SO_2R^6$, $SO_3H$, and $SO_2NHR^6$;

$R^6$ is independently selected at each occurrence from: H, $C_1$-$C_{10}$ alkyl, $C_6$-$C_{10}$ aryl, and $C_4$-$C_{10}$ heteroaryl;

$A^1$ is selected from: $C_6$-$C_{10}$ arylenyl, and $C_4$-$C_{10}$ heteroarylenyl;

$A^2$ is a functionalized imine-N containing $C_3$-$C_{10}$ heterocycle selected from: imidazoles, thiazoles, oxazolines, and pyridines;

$R^7$ is independently selected at each occurrence from: C(=O)OH, C(O)$NHR^8$, $NHR^8$, NHC(=O)$R^8$, $SO_3H$, and $SO_2NHR^8$;

$R^8$ is independently selected at each occurrence from: H, $C_1$-$C_{10}$ alkyl, $C_6$-$C_{10}$ aryl, and $C_4$-$C_{10}$ heteroaryl;

f is independently an integer from 0 to 3;
g is independently an integer from 0 to 3;
h is independently an integer from 0 to 3;
i is independently an integer from 0 to 3;
j is independently an integer from 1 to 3;

$R^9$, $R^{10}$, $R^{11}$ and $R^{12}$ are independently selected at each occurrence from: H, $R^{13}$, $C_1$-$C_{10}$ alkyl substituted with 0-3 $R^{13}$, $C_2$-$C_{10}$ alkenyl substituted with 0-3 $R^{13}$, $C_6$-$C_{10}$ aryl substituted with 0-2 $R^{13}$, and $C_4$-$C_{10}$ heteroaryl substituted with 0-2 $R^{13}$;

$R^{13}$ is independently selected at each occurrence from: OH, C(=O)OH, C(O)$OR^{14}$, C(O)$NHR^{14}$, $NHR^{14}$, NHC(=O)$R^{14}$, $SO_3H$, $SO_2R^{14}$, and $SO_2NHR^{14}$;

$R^{14}$ is independently selected at each occurrence from: H, $C_1$-$C_{10}$ alkyl, $C_6$-$C_{10}$ aryl, and $C_4$-$C_{10}$ heteroaryl;

Z is independently selected at each occurrence from: a bond, $CH_2$, C(O)$NR^{15}$, $NR^{16}$, $N^{15}$C(O), $NR^{15}SO_2$, O, $SO_2$, and $SO_2NR^{15}$;

$R^{15}$ is independently selected at each occurrence from: H, $C_1$-$C_{10}$ alkyl substituted with 0-3 $R^{17}$, $C_2$-$C_{10}$ alkenyl substituted with 0-3 $R^{17}$, $C_6$-$C_{10}$ aryl substituted with 0-2 $R^{17}$, and $C_4$-$C_{10}$ heteroaryl substituted with 0-2 $R^{17}$;

$R^{16}$ is independently selected at each occurrence from: H, $R^{18}$, C(O)$R^{18}$, and $SO_2R^{18}$;

$R^{17}$ is independently selected at each occurrence from: H, OH, C(=O)OH, C(O)$NHR^{19}$, $NHR^{19}$, NHC(=O)$R^{19}$, $OR^{19}$, $SO_2R^{19}$, $SO_3H$ and $SO_2NHR^{19}$;

$R^{18}$ is independently selected at each occurrence from: $C_1$-$C_{10}$ alkyl substituted with 0-3 $R^{17}$, $C_2$-$C_{10}$ alkenyl substituted with 0-3 $R^{17}$, $C_6$-$C_{10}$ aryl substituted $R^{17}$, and $C_4$-$C_{10}$ heteroaryl substituted with 0-2 $R^{17}$; and $R^{19}$ is independently selected at each occurrence from: H, $C_1$-$C_{10}$ alkyl, $C_6$-$C_{10}$ aryl, and $C_4$-$C_{10}$ heteroaryl.

In more preferred compounds of Formula I:

$E^1$ and $E^2$ are independently selected at each occurrence from: C(O)NH, NHC(O), and $SO_2NH$;

$R^1$ is selected from: H, $C_1$-$C_{10}$ alkyl, $C_6$-$C_{10}$ aryl, and $C_4$-$C_{10}$ heteroaryl;

$R^2$ and $R^3$ are independently selected at each occurrence from: H, phenyl substituted with $R^5$, $C_4$-$C_6$ heteroaryl substituted with $R^5$;

$R^5$ is independently selected at each occurrence from: C(=O)OH, C(O)$NHR^6$, $NHR^6$, NHC(=O)$R^6$, $SO_3H$, and $SO_2NHR^6$;

$R^6$ is independently selected at each occurrence from: H and $C_1$-$C_5$ alkyl;

$A^1$ is selected from: phenylenyl, furylenyl, thienylenyl, imidazolylenyl, thiazolylenyl, and pyridylenyl;

$A^2$ is a functionalized imidazoles or pyridine analogue;

$R^7$ is independently selected at each occurrence from: C(=O)OH, C(O)$NH_2$, $SO_3H$, and $SO_2NH_2$;

f is independently an integer of 0 to 2;
g is independently an integer of 0 to 2;
h is independently an integer of 0 to 2;
i is independently an integer of 0 to 2;
j is independently an integer of 1 to 2;

$R^9$, $R^{10}$, $R^{11}$ and $R^{12}$ are independently selected at each occurrence from: H, $R^{13}$, $C_1$-$C_5$ alkyl substituted with 0-2 $R^{13}$, $C_6$-$C_{10}$ aryl substituted with 0-2 $R^{13}$, and $C_4$-$C_{10}$ heteroaryl substituted with 0-2 $R^{13}$;

$R^{13}$ is independently selected at each occurrence from: OH, C(=O)OH, C(=O)$OCH_3$, C(O)$NH_2$, $SO_3H$, and $SO_2NH_2$;

Z is selected from: a bond, $CH_2$, O, C(O)$NR^{15}$, $NR^{16}$, $NR^{15}$C(O), $SO_2NR^{15}$, and $NR^{15}SO_2$;

$R^{15}$ is independently selected at each occurrence from: H, $C_1$-$C_5$ alkyl substituted with $R^{17}$, $C_6$-$C_{10}$ aryl substituted with $R^{17}$, and $C_4$-$C_{10}$ heteroaryl substituted with $R^{17}$;

$R^{16}$ is C(O)$R^{18}$ or $SO_2R^{18}$;

$R^{17}$ is independently selected at each occurrence from: H, OH, C(=O)OH, C(O)$NH_2$, and $SO_3H$; and $R^{18}$ is independently selected at each occurrence from: $C_1$-$C_5$ alkyl, $C_2$-$C_5$ alkenyl, $C_6$-$C_{10}$ aryl, and $C_4$-$C_{10}$ heteroaryl.

In even more preferred compounds of Formula I:

$E^1$ and $E^2$ are C(O)NH or NHC(O);

$R^1$ is H;

$R^2$ and $R^3$ are independently selected at each occurrence from: H and phenyl substituted with $R^5$;

$R^5$ is C(=O)OH or $SO_3H$;

$A^1$ is phenylenyl or pyridylenyl;

$A^2$ is a functionalized pyridine analogue;

f, g, h, and i are 0 or 1;

j is 1;

$R^9$, $R^{10}$, $R^{11}$ and $R^{12}$ are independently selected at each occurrence from: H, $R^{13}$, $C_1$-$C_5$ alkyl, and phenyl substituted with $R^{13}$;

$R^{13}$ is independently selected at each occurrence from: OH, C(=O)OH, C(=O)$OCH_3$, and $SO_3H$; and Z is independently selected at each occurrence from: a bond, $CH_2$, O, C(O)NH, NHC(O), $SO_2NH$, and $NHSO_2$.

In even more preferred compounds of Formula I:

$A^1$ is pyridylenyl;

$E^1$ is C(O)NH connected to $A^1$ at the 3-position of the pyridine ring;

$E^2$ is NHC(O) connected to $A^2$ at the ortho- or meta-position relative to the pyridine-N;

$R^2$ is H;

$R^3$ is 2-sulfonatophenyl;

f, g, h, i, and j are 1;

$R^9$, $R^{10}$, $R^{11}$ and $R^{12}$ are independently selected at each occurrence from: H, $R^{13}$, $C_1$-$C_5$ alkyl, and phenyl;

$R^{13}$ is selected from: C(=O)OH, C(=O)$OCH_3$, and $SO_3H$; and

Z is selected from: a bond, $CH_2$, C(O)NH, and NHC(O).

In preferred compounds of Formula I:

A$^1$ is pyridylenyl with the hydrazono group connected to A$^1$ at the ortho-position relative to the pyridine-N;

R$^9$, R$^{10}$, R$^{11}$ and R$^{12}$ are independently selected at each occurrence from: H, R$^{13}$, and C$_1$-C$_5$ alkyl;

R$^{13}$ is selected from: C(=O)OH, and C(=O)OCH$_3$; and

Z is selected from: CH$_2$, C(O)NH and NHC(O).

In further preferred compounds of Formula I:

R$^9$, R$^{10}$, R$^{11}$ and R$^{12}$ are H or R$^{13}$;

R$^{13}$ is C(=O)OCH$_3$; and

Z is CH$_2$ or C(O)NH.

Preferred compounds of Formula I include:

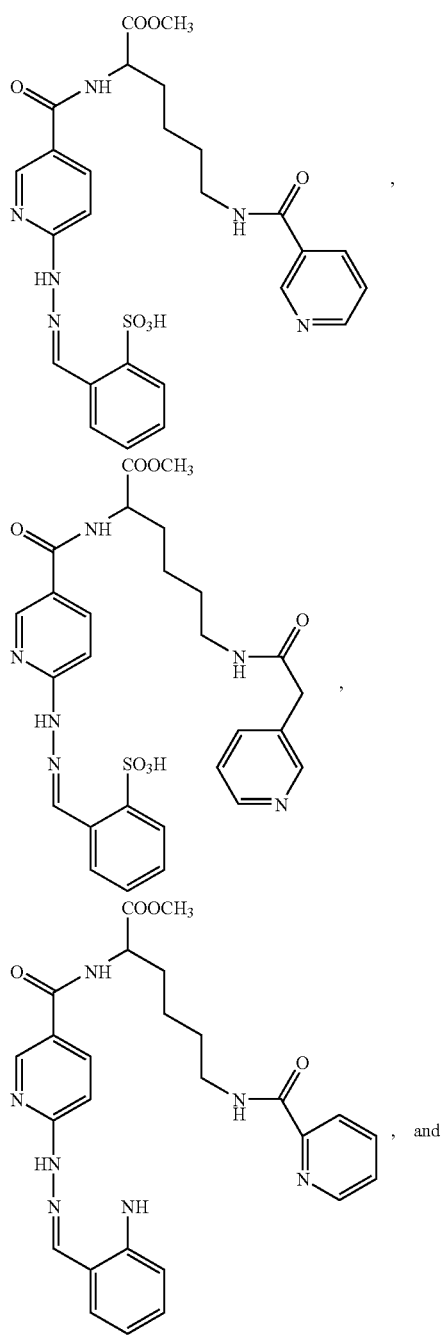

, and

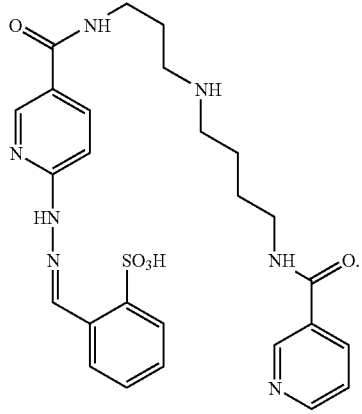

In a second aspect, the invention is directed to macrocyclic metal complexes of Formula II:

or a pharmaceutically acceptable salt thereof, wherein

M is a transition metal radionuclide selected from: $^{99m}$Tc, $^{186}$Re and $^{188}$Re;

L is a coligand capable of stabilizing the macrocyclic metal complex, and is a dioxygen chelating agent, functionalized pyridinecarboxylate, or functionalized aminocarboxylate;

n is 1 or 2;

E$^1$ and E$^2$ are independently selected at each occurrence from: a direct bond, CH$_2$, C(O), C(S), C(O)NH, C(S)NH, NHC(O), NHC(S), NHC(O)NH, NHC(S)NH, SO$_2$, and SO$_2$NH;

Hz is a hydrazino or diazenido group of formula —N(R$^1$)N=;

R$^1$ is selected from: a lone pair of electrons, a bond between the two nitrogen atoms, H, C$_1$-C$_{10}$ alkyl substituted with 0-5 R$^4$, C$_2$-C$_{10}$ alkenyl substituted with 0-5 R$^4$, C$_6$-C$_{10}$ aryl substituted with 0-3 R$^4$, and C$_4$-C$_{10}$ heteroaryl substituted with 0-3 R$^4$;

R$^4$ is independently selected at each occurrence from: OH, COOH, C(O)NH$_2$, SO$_3$H, and SO$_2$NH$_2$;

A$^1$ is selected from: C$_6$-C$_{10}$ arylenyl substituted with 0-2 R$^7$, and C$_4$-C$_{10}$ heteroarylenyl substituted with 0-2 R$^7$;

A$^2$ is a functionalized imine-N containing C$_3$-C$_{10}$ heterocycle substituted with 0-2 R$^7$;

R$^7$ is independently selected at each occurrence from: C(=O)OR$^8$, C(O)NHR$^8$, C(=O)R$^8$, NHR$^8$, NHC(=O)R$^8$, NHC(=O)NHR$^8$, NHC(=S)NHR$^8$, OR$^8$, OC(=O)R$^8$, OC(=O)OR$^8$, PO(OR$^8$)$_2$, SR$^8$, SOR$^8$, SO$_2$R$^8$, SO$_3$R$^8$, and SO$_2$NHR$^8$;

R$^8$ is independently selected at each occurrence from: H, C$_1$-C$_{10}$ alkyl, C$_2$-C$_{10}$ alkenyl, C$_3$-C$_{10}$ cycloalkyl, C$_6$-C$_{10}$ aryl, and C$_4$-C$_{10}$ heteroaryl;

D is a linker of the formula —[(CHR$^9$)$_f$(CHR$^{10}$)$_g$Z(CHR$^{11}$)$_h$(CHR$^{12}$)$_i$]$_j$—, f is independently an integer from 0 to 5;

g is independently an integer from 0 to 5;
h is independently an integer from 0 to 5;
i is independently an integer from 0 to 5;
j is independently an integer from 1 to 5;
$R^9$, $R^{10}$, $R^{11}$ and $R^{12}$ are independently selected at each occurrence from: H, $R^{13}$, $C_1$-$C_{10}$ alkyl substituted with 0-5 $R^{13}$, $C_2$-$C_{10}$ alkenyl substituted with 0-5 $R^{13}$, $C_3$-$C_{10}$ cycloalkyl substituted with 0-5 $R^{13}$, $C_6$-$C_{10}$ aryl substituted with 0-3 $R^{13}$, and $C_4$-$C_{10}$ heteroaryl substituted with 0-3 $R^{13}$;
alternatively $R^9$ and $R^{10}$, $R^9$ and $R^{11}$, $R^9$ and $R^{12}$, $R^{10}$ and $R^{11}$, $R^{10}$ and $R^{12}$ or $R^{11}$ and $R^{12}$, may be taken together to form a $C_3$-$C_{10}$ cycloalkyl or $C_5$-$C_{10}$ cycloalkenyl;
$R^{13}$ is independently selected at each occurrence from: C(=O)O$R^{14}$, C(O)NH$R^{14}$, C(=O)$R^{14}$, NH$R^{14}$, NHC(=O)$R^{14}$, NHC(=O)NH$R^{14}$, NHC(=S)NH$R^{14}$, O$R^{14}$, OC(=O)$R^{14}$, OC(=O)O$R^{14}$, PO(O$R^{14}$)$_2$, S$R^{14}$, SO$R^{14}$, SO$_2R^{14}$, SO$_3R^{14}$, and SO$_2$NH$R^{14}$;
$R^{14}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
Z is independently selected from: a bond, CH$_2$, C(O), C(O)N$R^{15}$, C(S)N$R^{15}$, N$R^{16}$, N$R^{15}$C(O), N$R^{15}$C(S), NHC(=NH)NH, NHC(O)NH, NHC(S)NH, N$R^{15}$SO$_2$, O, S, SO, SO$_2$, and SO$_2$N$R^{15}$;
$R^{15}$ is independently selected at each occurrence from: H, $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$ and $C_4$-$C_{10}$ heteroaryl substituted with 0-3 $R^{17}$;
$R^{16}$ is independently selected at each occurrence from: H, $R^{18}$, C(O)$R^{18}$, SO$_2R^{18}$, and C(O)N($R^{18}$);
$R^{17}$ is independently selected at each occurrence from: OH, C(=O)O$R^{19}$, C(O)NH$R^{19}$, C(=O)$R^{19}$, NH$R^{19}$, NHC(=O)$R^{19}$, NHC(=O)NH$R^{19}$, NHC(=S)NH$R^{19}$, O$R^{19}$, OC(=O)$R^{19}$, OC(=O)O$R^{19}$, PO(O$R^{19}$)$_2$, SO$_2R^{19}$, SO$_3R^{19}$, and SO$_2$NH$R^{19}$;
$R^{18}$ is independently selected at each occurrence from: $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$, and $C_4$-$C_{10}$ heteroaryl substituted with 0-3 $R^{17}$; and
$R^{19}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl.

In preferred macrocyclic metal complexes of Formula II:
M is $^{99m}$Tc;
L is a functionalized aminocarboxylate;
n is 1;
$E^1$ and $E^2$ are independently selected at each occurrence from: C(O)NH, NHC(O), NHC(O)NH, NHC(S)NH, and SO$_2$NH;
$R^1$ is selected from: a lone pair of electrons, H, $C_1$-$C_{10}$ alkyl substituted with 0-3 $R^4$, $C_2$-$C_{10}$ alkenyl substituted with 0-3 $R^4$, $C_6$-$C_{10}$ aryl substituted with 0-2 $R^4$, and $C_4$-$C_{10}$ heteroaryl substituted with 0-2 $R^4$;
$R^4$ is independently selected at each occurrence from: OH, COOH, and SO$_3$H;
$R^7$ is independently selected at each occurrence from: C(=O)OH, C(O)NH$R^8$, NH$R^8$, NHC(=O)$R^8$, SO$_3$H, and SO$_2$NH$R^8$;

$R^8$ is independently selected at each occurrence from: H, $C_1$-$C_{10}$ alkyl, $C_6$-$C_{10}$ aryl, and $C_4$-$C_{10}$ heteroaryl;
f is independently an integer of 0 to 3;
g is independently an integer of 0 to 3;
h is independently an integer of 0 to 3;
i is independently an integer of 0 to 3;
j is independently an integer of 1 to 3;
$R^9$, $R^{10}$, $R^{11}$ and $R^{12}$ are independently selected at each occurrence from: H, $R^{13}$, $C_1$-$C_{10}$ alkyl substituted with 0-3 $R^{13}$, $C_2$-$C_{10}$ alkenyl substituted with 0-3 $R^{13}$, $C_6$-$C_{10}$ aryl substituted with 0-2 $R^{13}$, and $C_4$-$C_{10}$ heteroaryl substituted with 0-2 $R^{13}$;
$R^{13}$ is independently selected at each occurrence from: OH, C(=O)OH, C(O)O$R^{14}$, C(O)NH$R^{14}$, NH$R^{14}$, NHC(=O)$R^{14}$, SO$_2R^{14}$, and SO$_2$NH$R^{14}$;
$R^{14}$ is independently selected at each occurrence from: H, $C_1$-$C_{10}$ alkyl, $C_6$-$C_{10}$ aryl, and $C_4$-$C_{10}$ heteroaryl;
Z is independently selected at each occurrence from: a bond, CH$_2$, C(O)N$R^{15}$, N$R^{16}$, N$R^{15}$C(O), N$R^{15}$SO$_2$, O, SO$_2$, and SO$_2$N$R^{15}$;
$R^{15}$ is independently selected at each occurrence from: H, $C_1$-$C_{10}$ alkyl substituted with 0-3 $R^{17}$, $C_2$-$C_{10}$ alkenyl substituted with 0-3 $R^{17}$, $C_6$-$C_{10}$ aryl substituted with 0-2 $R^{17}$, and $C_4$-$C_{10}$ heteroaryl substituted with 0-2 $R^{17}$;
$R^{16}$ is independently selected at each occurrence from: H, $R^{18}$, C(O)$R^{18}$, and SO$_2R^{18}$;
$R^{17}$ is independently selected at each occurrence from: OH, C(=O)OH, C(O)NH$R^{19}$, NH$R^{19}$, NHC(=O)$R^{19}$, O$R^{19}$, SO$_2R^{19}$, SO$_3$H and SO$_2$NH$R^{19}$;
$R^{18}$ is independently selected at each occurrence from: $C_1$-$C_{10}$ alkyl substituted with 0-3 $R^{17}$, $C_2$-$C_{10}$ alkenyl substituted with 0-3 $R^{17}$, $C_6$-$C_{10}$ aryl substituted with 0-2 $R^{17}$, and $C_4$-$C_{10}$ heteroaryl substituted with 0-2 $R^{17}$; and
$R^{19}$ is independently selected at each occurrence from: H, $C_1$-$C_{10}$ alkyl, $C_6$-$C_{10}$ aryl, and $C_4$-$C_{10}$ heteroaryl.

In even more preferred macrocyclic metal complexes of Formula II:
$E^1$ and $E^2$ are independently selected at each occurrence from: C(O)NH, NHC(O), and SO$_2$NH;
$R^1$ is selected from: a lone pair of electrons, H, $C_1$-$C_{10}$ alkyl and $C_4$-$C_6$ heteroaryl;
$A^1$ is selected from: phenylenyl, furylenyl, thienylenyl, imidazolylenyl, thiazolylenyl, and pyridylenyl;
$A^2$ is a functionalized imidazoles or pyridine analogue;
$R^7$ is independently selected at each occurrence from: C(=O)OH, C(O)NH$_2$, SO$_3$H, and SO$_2$NH$_2$;
f is independently an integer of 0 to 2;
g is independently an integer of 0 to 2;
h is independently an integer of 0 to 2;
i is independently an integer of 0 to 2;
j is independently an integer of 1 to 2;
$R^9$, $R^{10}$, $R^{11}$ and $R^{12}$ are independently selected at each occurrence from: H, $R^{13}$, $C_1$-$C_5$ alkyl substituted with 0-2 $R^{13}$, $C_6$-$C_{10}$ aryl substituted with 0-2 $R^{13}$, and $C_4$-$C_{10}$ heteroaryl substituted with 0-2 $R^{13}$;
$R^{13}$ is independently selected at each occurrence from: OH, C(=O)OH, C(=O)OCH$_3$, C(O)NH$_2$, SO$_3$H, and SO$_2$NH$_2$;

Z is selected from: a bond, $CH_2$, O, $C(O)NR^{15}$, $NR^{16}$, $NR^{15}C(O)$, $SO_2NR^{15}$, and $NR^{15}SO_2$;

$R^{15}$ is independently selected at each occurrence from: H, $C_1$-$C_5$ alkyl substituted with $R^{17}$, $C_6$-$C_{10}$ aryl substituted with $R^{17}$, and $C_4$-$C_{10}$ heteroaryl substituted with $R^{17}$;

$R^{16}$ is $C(O)R^{18}$ or $SO_2R^{18}$;

$R^{17}$ is independently selected at each occurrence from: OH, $C(=O)OH$, $C(O)NH_2$, and $SO_3H$; and $R^{18}$ is independently selected at each occurrence from: $C_1$-$C_5$ alkyl, $C_2$-$C_5$ alkenyl, $C_6$-$C_{10}$ aryl, and $C_4$-$C_{10}$ heteroaryl.

In yet even more preferred macrocyclic metal complexes of Formula II:

$E^1$ and $E^2$ are C(O)NH or NHC(O);

$R^1$ is a lone pair of electrons or H;

$A^1$ is phenylenyl or pyridylenyl;

$A^2$ is a functionalized pyridine analogue;

f, g, h, and i are 0 or 1;

j is 1;

$R^9$, $R^{10}$, $R^{11}$ and $R^{12}$ are independently selected at each occurrence from: H, $R^{13}$, $C_1$-$C_5$ alkyl, and phenyl substituted with $R^{13}$;

$R^{13}$ is independently selected at each occurrence from: OH, $C(=O)OH$, $C(=O)OCH_3$, and $SO_3H$; and Z is independently selected at each occurrence from: a bond, $CH_2$, C(O), C(O)NH, NHC(O), $NR^{15}C(S)$, $NHSO_2$, O, and $SO_2NH$.

In further preferred macrocyclic metal complexes of Formula II:

$A^1$ is pyridylenyl;

$E^1$ is C(O)NH connected to $A^1$ at the 3-position of the pyridine ring;

$E^2$ is NHC(O) connected to $A^2$ at the ortho- or meta-position relative to the pyridine-N;

f, g, h, i, and j are 1;

$R^9$, $R^{10}$, $R^{11}$ and $R^{12}$ are independently selected at each occurrence from: H, $R^{13}$, $C_1$-$C_5$ alkyl, and phenyl;

$R^{13}$ is selected from: $C(=O)OH$, $C(=O)OCH_3$, and $SO_3H$; and

Z is selected from: a bond, $CH_2$, C(O)NH and NHC(O).

In even more preferred macrocyclic metal complexes of Formula II:

$A^1$ is pyridylenyl with the hydrazino or diazenido group being connected to $A^1$ at the ortho-position relative to the pyridine-N;

$R^9$, $R^{10}$, $R^{11}$ and $R^{12}$ are independently selected at each occurrence from: H, $R^{13}$, and $C_1$-$C_5$ alkyl;

$R^{13}$ is selected from: $C(=O)OH$, and $C(=O)OCH_3$; and

Z is selected from: $CH_2$, C(O)NH and NHC(O).

In further preferred macrocyclic metal complexes of Formula II:

$R^9$, $R^{10}$, $R^{11}$ and $R^{12}$ are H or $R^{13}$;

$R^{13}$ is $C(=O)OCH_3$; and

Z is $CH_2$ or C(O)NH.

Preferred macrocyclic metal complexes of Formula II include:

-continued
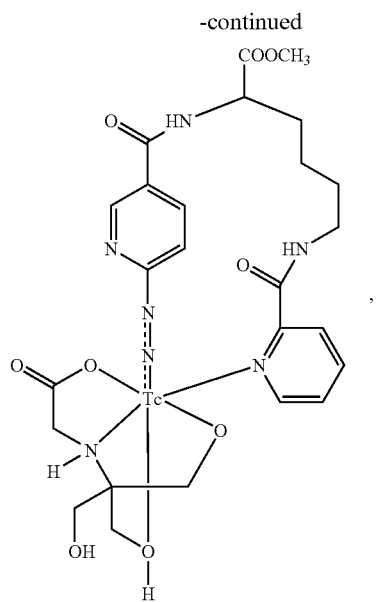
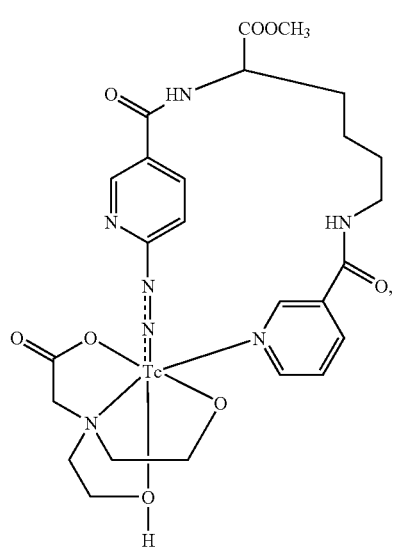
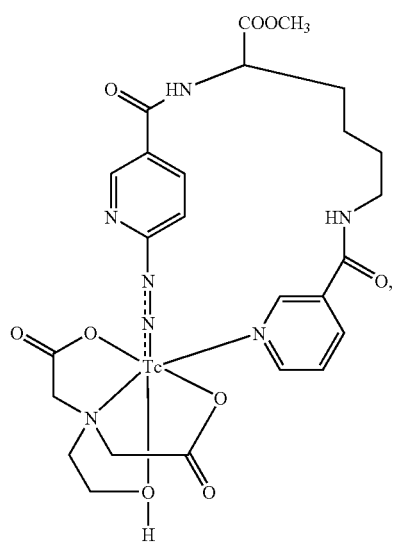
-continued
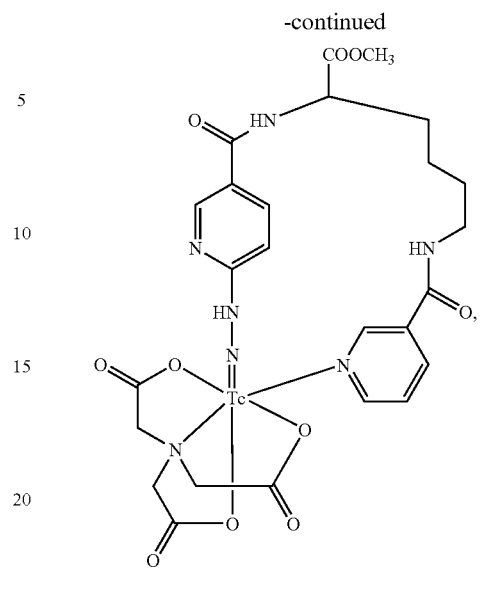
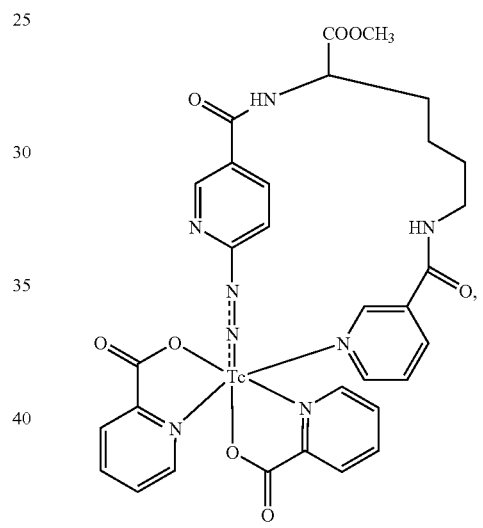
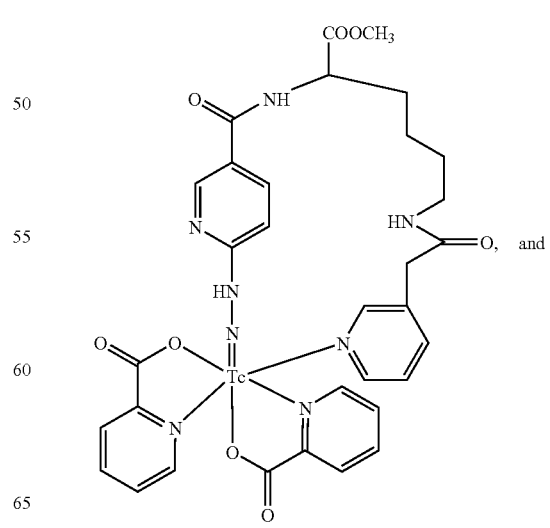
and -continued

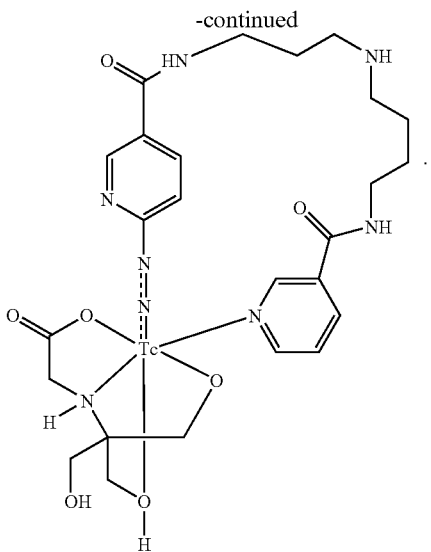

In other embodiments, the invention is directed to radiopharmaceutical compositions, comprising said macrocyclic metal complex of Formula II.

In another embodiment, the invention is directed to kits for forming a macrocyclic metal complex radiopharmaceutical, comprising:
 a compound of Formula I;
 a coligand selected from the group: dioxygen chelating agent, functionalized pyridinecarboxylate, and functionalized aminocarboxylate, preferably tricine;
 a reducing agent, preferably stannous chloride; and
 instructions for contacting said compound, said coligand and said reducing agent with a radionuclide, preferably [$^{99m}$Tc]pertechnetate, under conditions sufficient to produce said macrocyclic metal complex radiopharmaceutical.

In another embodiment, the invention is directed to kits for forming a macrocyclic metal complex radiopharmaceutical, comprising:
 a predetermined quantity of a sterile, pharmaceutically-acceptable compound of Formula I;
 a predetermined quantity of sterile, pharmaceutically-acceptable stabilizing coligand selected from the group: dioxygen chelating agent, functionalized pyridinecarboxylate, and functionalized aminocarboxylate, preferably tricine;
 a predetermined quantity of a sterile, pharmaceutically-acceptable reducing agent, preferably stannous chloride; and
 optionally, a predetermined quantity of one or more sterile, pharmaceutically acceptable components selected from the group: buffers, lyophilization aids, stabilization aids, solubilization aids and bacteriostats.

In yet another embodiment, the invention is directed to diagnostic compositions, comprising:
 a diagnostically-effective amount of the macrocyclic metal complex of Formula II; and
 a pharmaceutically acceptable carrier.

In yet other embodiments, the invention is directed to methods for radioimaging a patient, comprising the steps of:
 administering to said patient an effective amount of said macrocyclic metal complex of Formula II; and
 scanning said patient using a radioimaging device.

In a third aspect, the invention is directed to conjugates of Formula III:

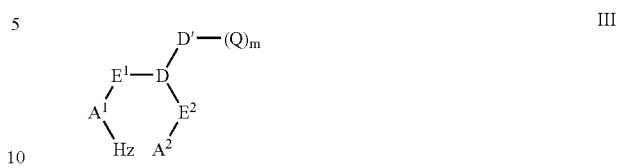

III or a pharmaceutically acceptable salt thereof, wherein
 $E^1$ and $E^2$ are independently selected at each occurrence from: a direct bond, $CH_2$, C(O), C(S), C(O)NH, C(S)NH, NHC(O), NHC(S), NHC(O)NH, NHC(S)NH, $SO_2$, and $SO_2NH$;
 Hz is the free hydrazine moiety or a hydrazone of the formula $-N(R^1)N=C(R^2)(R^3)$,
 $R^1$ is selected from: H, $C_1$-$C_{10}$ alkyl substituted with 0-5 $R^4$, $C_2$-$C_{10}$ alkenyl substituted with 0-5 $R^4$, $C_6$-$C_{10}$ aryl substituted with 0-3 $R^4$, and $C_4$-$C_{10}$ heteroaryl substituted with 0-3 $R^4$;
 $R^2$ and $R^3$ are independently selected at each occurrence from: H, CN, $CO_2R^5$, $C(O)R^5$, $C(O)N(R^5)_2$, $C_1$-$C_{10}$ alkyl substituted with 0-5 $R^5$, $C_2$-$C_{10}$ alkenyl substituted with 0-5 $R^5$, $C_3$-$C_{10}$ cycloalkyl substituted with 0-5 $R^5$, $C_6$-$C_{10}$ aryl substituted with 0-3 $R^5$, and $C_4$-$C_{10}$ heteroaryl substituted with 0-3 $R^5$; or alternatively $R^2$ and $R^3$ may be taken together to form a $C_3$-$C_{10}$ cycloalkyl or $C_5$-$C_{10}$ cycloalkenyl;
 $R^4$ is independently selected at each occurrence from: OH, COOH, $C(O)NH_2$, $SO_3H$, and $SO_2NH_2$;
 $R^5$ is independently selected at each occurrence from: $C(=O)OR^6$, $C(O)NHR^6$, $C(=O)R^6$, $NHR^6$, $NHC(=O)R^6$, $NHC(=O)NHR^6$, $NHC(=S)NHR^6$, $OR^6$, $OC(=O)R^6$, $OC(=O)OR^6$, $PO(OR^6)_2$, $SR^6$, $SOR^6$, $SO_2R^6$, $SO_3R^6$, and $SO_2NHR^6$;
 $R^6$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
 $A^1$ is selected from: $C_6$-$C_{10}$ arylenyl substituted with 0-2 $R^7$, and $C_4$-$C_{10}$ heteroarylenyl substituted with 0-2 $R^7$;
 $A^2$ is a functionalized imine-N containing $C_3$-$C_{10}$ heterocycle substituted with 0-2$R^7$;
 $R^7$ is independently selected at each occurrence from: $C(=O)OR^8$, $C(O)NHR^8$, $C(=O)R^8$, $NHR^8$, $NHC(=O)R^8$, $NHC(=O)NHR^8$, $NHC(=S)NHR^8$, $OR^8$, $OC(=O)R^8$, $OC(=O)OR^8$, $PO(OR^8)_2$, $SR^8$, $SOR^8$, $SO_2R^8$, $SO_3R^8$, and $SO_2NHR^8$;
 $R^8$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
 D is a linker of the formula $-[(CHR^9)_f(CHR^{10})_gZ(CHR^{11})_h(CHR^{12})_i]_j-$,
 f is independently an integer from 0 to 5;
 g is independently an integer from 0 to 5;
 h is independently an integer from 0 to 5;
 i is independently an integer from 0 to 5;
 j is independently an integer from 1 to 5;
 $R^9$, $R^{10}$, $R^{11}$ and $R^{12}$ are independently selected at each occurrence from: H, $R^{13}$, $C_1$-$C_{10}$ alkyl substituted with 0-5 $R^{13}$, $C_2$-$C_{10}$ alkenyl substituted with 0-5 $R^{13}$, $C_3$-$C_{10}$ cycloalkyl substituted with 0-5 $R^{13}$, $C_6$-$C_{10}$ aryl substituted with 0-3 $R^{13}$, $C_4$-$C_{10}$ heteroaryl substituted with 0-3 $R^{13}$;

alternatively R$^9$ and R$^{10}$, R$^9$ and R$^{11}$, R$^9$ and R$^{12}$, R$^{10}$ and R$^{11}$, R$^{10}$ and R$^{12}$ or R$^{11}$ and R$^{12}$, may be taken together to form a C$_3$-C$_{10}$ cycloalkyl or C$_5$-C$_{10}$ cycloalkenyl;

R$^{13}$ is independently selected at each occurrence from: C(=O)OR$^{14}$, C(O)NHR$^{14}$, C(=O)R$^{14}$, NHR$^{14}$, NHC(=O)R$^{14}$, NHC(=O)NHR$^{14}$, NHC(=S)NHR$^{14}$, OR$^{14}$, OC(=O)R$^{14}$, OC(=O)OR$^{14}$, PO(OR$^{14}$)$_2$, SR$^{14}$, SOR$^{14}$, SO$_2$R$^{14}$, SO$_3$R$^{14}$, and SO$_2$NHR$^{14}$;

R$^{14}$ is independently selected at each occurrence from: H, C$_1$-C$_{10}$ alkyl, C$_2$-C$_{10}$ alkenyl, C$_3$-C$_{10}$ cycloalkyl, C$_6$-C$_{10}$ aryl, and C$_4$-C$_{10}$ heteroaryl;

Z is independently selected at each occurrence from: a bond, CH$_2$, C(O), C(O)NR$^{15}$, C(S)NR$^{15}$, NR$^{16}$, NR$^{15}$C(O), NR$^{15}$C(S), NHC(=NH)NH, NHC(O)NH, NHC(S)NH, NR$^{15}$SO$_2$, O, S, SO, SO$_2$, and SO$_2$NR$^{15}$;

R$^{15}$ is independently selected at each occurrence from: H, C$_1$-C$_{10}$ alkyl substituted with 0-5 R$^{17}$, C$_2$-C$_{10}$ alkenyl substituted with 0-5 R$^{17}$, C$_3$-C$_{10}$ cycloalkyl substituted with 0-5 R$^{17}$, C$_6$-C$_{10}$ aryl substituted with 0-3 R$^{17}$ and C$_4$-C$_{10}$ heteroaryl substituted with 0-3 R$^{17}$;

R$^{16}$ is independently selected at each occurrence from: H, R$^{18}$, C(O)R$^{18}$, SO$_2$R$^{18}$, and C(O)N(R$^{18}$);

R$^{17}$ is independently selected at each occurrence from: OH, C(=O)OR$^{19}$, C(O)NHR$^{19}$, C(=O)R$^{19}$, NHR$^{19}$, NHC(=O)R$^{19}$, NHC(=O)NHR$^{19}$, NHC(=S)NHR$^{19}$, OR$^{19}$, OC(=O)R$^{19}$, OC(=O)OR$^{19}$, PO(OR$^{19}$)$_2$, SO$_2$R$^{19}$, SO$_3$R$^{19}$, and SO$_2$NHR$^{19}$;

R$^{18}$ is independently selected at each occurrence from: C$_1$-C$_{10}$ alkyl substituted with 0-5 R$^{17}$, C$_2$-C$_{10}$ alkenyl substituted with 0-5 R$^{17}$, C$_3$-C$_{10}$ cycloalkyl substituted with 0-5 R$^{17}$, C$_6$-C$_{10}$ aryl substituted with 0-3 R$^{17}$, and C$_4$-C$_{10}$ heteroaryl substituted with 0-3 R$^{17}$;

R$^{19}$ is independently selected at each occurrence from: H, C$_1$-C$_{10}$ alkyl, C$_2$-C$_{10}$ alkenyl, C$_3$-C$_{10}$ cycloalkyl, C$_6$-C$_{10}$ aryl, and C$_4$-C$_{10}$ heteroaryl;

Q is a biologically active group;

m is an integer of 1 to 20;

D' is a pharmacokinetic modifier having the formula:

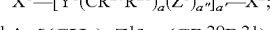

X$^1$ is [(CH$_2$)$_b$Z$^1$]$_{b'}$-(CR$^{20}$R$^{21}$)$_{b''}$;
X$^2$ is (CR$^{20}$R$^{21}$)$_{b''}$-[Z$^1$(CH$_2$)$_b$]$_{b'}$;
a is independently an integer of 0 to 10;
a' is independently an integer of 0 to 10;
a" independently an integer of 0 to 1;
b is independently an integer of 0 to 10;
b' independently an integer of 0 to 1;
b" is independently an integer of 0 to 10;
Y$^1$ and Y$^2$, at each occurrence, are independently selected from: a bond, O, NR$^{21}$, C=O, C(=O)O, OC(=O)O, C(=O)NH—, C=NR$^{21}$, S, SO, SO$_2$, SO$_3$, NHC(=O), (NH)$_2$C(=O), and (NH)$_2$C=S;

Z is independently selected at each occurrence from: C$_6$-C$_{14}$ saturated, partially saturated, or aromatic carbocyclic ring system, substituted with 0-4 R$^{22}$; and a heterocyclic ring system, optionally substituted with 0-4 R$^{22}$;

R$^{20}$ and R$^{21}$ are independently selected at each occurrence from: H, C$_1$-C$_{10}$ alkyl substituted with 0-5 R$^{23}$, and aryl substituted with 0-5 R$^{23}$;

R$^{22}$ and R$^{23}$ are independently selected at each occurrence from the group: OH, NHR$^{24}$, C(=O)R$^{24}$, OC(=O)R$^{24}$, OC(=O)OR$^{24}$, C(=O)OR$^{24}$, C(=O)NR$^{24}$, —CN, SR$^{24}$, SOR$^{24}$, SO$_2$R$^{24}$, NHC(=O)R$^{24}$, NHC(=O)NHR$^{24}$, and NHC(=S)NHR$^{24}$;

alternatively, when m is greater than 1, R$^{23}$ is independently selected at each occurrence from the group: O, NR$^{24}$, C=O, C(=O)O, OC(=O)O, C(=O)N, C=NR$^{24}$, S, SO, SO$_2$, SO$_3$, NHC(=O), (NH)$_2$C(=O), and (NH)$_2$C=S; and R$^{24}$ is independently selected at each occurrence from the group: H, C$_1$-C$_6$ alkyl, benzyl, and phenyl.

In preferred conjugates of Formula III:

E$^1$ and E$^2$ are independently selected at each occurrence from: C(O)NH, NHC(O), NHC(O)NH, NHC(S)NH, and SO$_2$NH;

R$^1$ is selected from: H, C$_1$-C$_{10}$ alkyl substituted with 0-3 R$^4$, C$_2$-C$_{10}$ alkenyl substituted with 0-3 R$^4$, C$_6$-C$_{10}$ aryl substituted with 0-2 R$^4$, and C$_4$-C$_{10}$ heteroaryl substituted with 0-2 R$^4$;

R$^2$ and R$^3$ are independently selected at each occurrence from: H, C$_6$-C$_{10}$ aryl substituted with 0-2 R$^5$, and C$_4$-C$_{10}$ heteroaryl substituted with 0-2 R$^5$;

R$^4$ is independently selected at each occurrence from: OH, COOH, and SO$_3$H;

R$^5$ is independently selected at each occurrence from: C(=O)OH, C(O)NHR$^6$, NHR$^6$, NHC(=O)R$^6$, NHC(=S)NHR$^6$, SO$_2$R$^6$, SO$_3$H, and SO$_2$NHR$^6$;

R$^6$ is independently selected at each occurrence from: H, C$_1$-C$_{10}$ alkyl, C$_6$-C$_{10}$ aryl, and C$_4$-C$_{10}$ heteroaryl;

A$^1$ is selected from: C$_6$-C$_{10}$ arylenyl, and C$_4$-C$_{10}$ heteroarylenyl;

A$^2$ is a functionalized imine-N containing C$_3$-C$_{10}$ heterocycle selected from: imidazoles, thiazoles, oxazolines, and pyridines;

R$^7$ is independently selected at each occurrence from: C(=O)OH, C(O)NHR$^8$, NHR$^8$, NHC(=O)R$^8$, SO$_3$H, and SO$_2$NHR$^8$;

R$^8$ is independently selected at each occurrence from: H, C$_1$-C$_{10}$ alkyl, C$_6$-C$_{10}$ aryl, and C$_4$-C$_{10}$ heteroaryl;

f is independently an integer from 0 to 3;
g is independently an integer from 0 to 3;
h is independently an integer from 0 to 3;
i is independently an integer from 0 to 3;
j is independently an integer from 1 to 3;

R$^9$, R$^{10}$, R$^{11}$ and R$^{12}$ are independently selected at each occurrence from: H, R$^{13}$, C$_1$-C$_{10}$ alkyl substituted with 0-3 R$^{13}$, C$_2$-C$_{10}$ alkenyl substituted with 0-3 R$^{13}$, C$_6$-C$_{10}$ aryl substituted with 0-2 R$^{13}$, and C$_4$-C$_{10}$ heteroaryl substituted with 0-2 R$^{13}$;

R$^{13}$ is independently selected at each occurrence from: OH, C(=O)OH, C(O)OR$^{14}$, C(O)NHR$^{14}$, NHR$^{14}$, NHC(=O)R$^{14}$, SO$_3$H, SO$_2$R$^{14}$, and SO$_2$NHR$^{14}$;

R$^{14}$ is independently selected at each occurrence from: H, C$_1$-C$_{10}$ alkyl, C$_6$-C$_{10}$ aryl, and C$_4$-C$_{10}$ heteroaryl;

Z is independently selected at each occurrence from: a bond, CH$_2$, C(O)NR$^{15}$, NR$^{16}$, NR$^{15}$C(O), NR$^{15}$SO$_2$, O, SO$_2$, and SO$_2$NR$^{15}$;

R$^{15}$ is independently selected at each occurrence from: H, C$_1$-C$_{10}$ alkyl substituted with 0-3 R$^{17}$, C$_2$-C$_{10}$ alkenyl substituted with 0-3 R$^{17}$, C$_6$-C$_{10}$ aryl substituted with 0-2 R$^{17}$, and C$_4$-C$_{10}$ heteroaryl substituted with 0-2 R$^{17}$;

R$^{16}$ is independently selected at each occurrence from: H, R$^{18}$, C(O)R$^{18}$, and SO$_2$R$^{18}$;

R$^{17}$ is independently selected at each occurrence from: H, OH, C(=O)OH, C(O)NHR$^{19}$, NHR$^{19}$, NHC(=O)R$^{19}$, OR$^{19}$, SO$_2$R$^{19}$, SO$_3$H, and SO$_2$NHR$^{19}$;

R$^{18}$ is independently selected at each occurrence from: C$_1$-C$_{10}$ alkyl substituted with 0-3 R$^{17}$, C$_2$-C$_{10}$ alkenyl substituted with 0-3 R$^{17}$, C$_6$-C$_{10}$ aryl substituted with 0-2 R$^{17}$, and C$_4$-C$_{10}$ heteroaryl substituted with 0-2 R$^{17}$;

R$^{19}$ is independently selected at each occurrence from: H, C$_1$-C$_{10}$ alkyl, C$_6$-C$_{10}$ aryl, and C$_4$-C$_{10}$ heteroaryl;

Q is a biomolecule selected from the group: platelet GPIIb/IIIa receptor binders (including agonists or antagonists), preferably IIb/IIIa receptor ligand, fibrin binding compounds, leukocyte binding compounds, chemotactic compounds (including peptides), $LTB_4$ receptor binders (including agonists and antagonists), somatostatin analogs, selectin binding compounds, vitronectin receptor binders (including agonists and antagonists), kinase inhibitors (including tyrosine kinase inhibitors), matrix metalloproteinase inhibitors, oligonucleotides, fatty acids, nitroimidazoles, and carbohydrates;

m is an integer from 1 to 3;

a is independently an integer from 0 to 5;

a' is independently an integer from 0 to 5;

a", b, and b' are 0;

b" is independently an integer from 0 to 5;

$Y^1$ and $Y^2$, at each occurrence, are independently selected from: a bond, O, $NR^{21}$, C=O, C(=O)O, OC(=O)O, C(=O)NH—, C=$NR^{21}$, $SO_2$, NHC(=O), $(NH)_2C(=O)$, and $(NH)_2C=S$;

$R^{20}$ and $R^{21}$ are independently selected at each occurrence from: H, $C_1$-$C_5$ alkyl substituted with 0-3 $R^{23}$, and aryl substituted with 0-3 $R^{23}$;

$R^{23}$ is independently selected at each occurrence from the group: OH, $NHR^{24}$, $C(O)R^{24}$, $C(O)OR^{24}$, $C(O)NR^{24}$, $SR^{24}$, $SO_2R^{24}$, $NHC(O)R^{24}$, $NHC(O)NHR^{24}$, and NHC(S)$NHR^{24}$;

alternatively, when m is greater than 1, $R^{23}$ is independently selected at each occurrence from the group: O, $NR^{24}$, C(O)O, OC(O)O, C(O)N, C=$NR^{24}$, $SO_2$, NHC(O), $(NH)_2C(O)$, and $(NH)_2C(S)$; and $R^{24}$ is independently selected at each occurrence from the group: H, $C_1$-$C_5$ alkyl, benzyl, and phenyl.

In yet further preferred conjugates of Formula III:

$E^1$ and $E^2$ are independently selected at each occurrence from: C(O)NH, NHC(O), and $SO_2NH$;

$R^1$ is selected from: H, $C_1$-$C_{10}$ alkyl, $C_6$-$C_{10}$ aryl, and $C_4$-$C_{10}$ heteroaryl;

$R^2$ and $R^3$ are independently selected at each occurrence from: H, phenyl substituted with $R^5$, $C_4$-$C_6$ heteroaryl substituted with $R^5$;

$R^5$ is independently selected at each occurrence from: C(=O)OH, $C(O)NHR^6$, $NHR^6$, NHC(=O)$R^6$, $SO_3H$, and $SO_2NHR^6$;

$R^6$ is independently selected at each occurrence from: H and $C_1$-$C_5$ alkyl;

$A^1$ is selected from: phenylenyl, furylenyl, thienylenyl, imidazolylenyl, thiazolylenyl, and pyridylenyl;

$A^2$ is a functionalized imidazoles or pyridine analogue;

$R^7$ is independently selected at each occurrence from: C(=O)OH, $C(O)NH_2$, $SO_3H$, and $SO_2NH_2$;

f is independently an integer of 0 to 2;

g is independently an integer of 0 to 2;

h is independently an integer of 0 to 2;

i is independently an integer of 0 to 2;

j is independently an integer of 1 to 2;

$R^9$, $R^{10}$, $R^{11}$ and $R^{12}$ are independently selected at each occurrence from: H, $R^{13}$, $C_1$-$C_5$ alkyl substituted with 0-2 $R^{13}$, $C_6$-$C_{10}$ aryl substituted with 0-2 $R^{13}$, and $C_4$-$C_{10}$ heteroaryl substituted with 0-2 $R^{13}$;

$R^{13}$ is independently selected at each occurrence from: OH, C(=O)OH, C(=O)$OCH_3$, $C(O)NH_2$, $SO_3H$, and $SO_2NH_2$;

Z is selected from: a bond, $CH_2$, O, $C(O)NR^{15}$, $NR^{16}$, $NR^{15}C(O)$, $SO_2NR^{15}$, and $NR^{15}SO_2$;

$R^{15}$ is independently selected at each occurrence from: H, $C_1$-$C_5$ alkyl substituted with $R^{17}$, $C_6$-$C_{10}$ aryl substituted with $R^{17}$, and $C_4$-$C_{10}$ heteroaryl substituted with $R^{17}$;

$R^{16}$ is $C(O)R^{18}$ or $SO_2R^{18}$;

$R^{17}$ is independently selected at each occurrence from: H, OH, C(=O)OH, $C(O)NH_2$, and $SO_3H$;

$R^{18}$ is independently selected at each occurrence from: $C_1$-$C_5$ alkyl, $C_2$-$C_5$ alkenyl, $C_6$-$C_{10}$ aryl, and $C_4$-$C_{10}$ heteroaryl;

Q is a biomolecule selected from the group: platelet GPIIb/IIIa receptor binders (including agonists and antagonists), preferably IIb/IIIa receptor ligands, fibrin binding compounds (including peptides), chemotactic compounds (including peptides), $LTB_4$ receptor binders (including agonists and antagonists), somatostatin analogs, vitronectin receptor binders (including agonists and antagonists), and matrix metalloproteinase inhibitors;

m is 1;

a is independently an integer of 1 to 3;

a' is independently an integer of 1 to 3;

b" is independently an integer of 1 to 3;

$Y^1$ and $Y^1$ are independently selected at each occurrence from: a bond, O, NH, C(O)NH—, NHC(O), and $(NH)_2C=S$;

$R^{20}$ and $R^{21}$ are independently selected at each occurrence from: H, $C_1$-$C_5$ alkyl substituted with 0-2 $R^{23}$, and aryl substituted with 0-2 $R^{23}$;

$R^{23}$ is independently selected at each occurrence from the group: H, $NHR^{24}$, $C(O)NR^{24}$, $NHC(O)R^{24}$, NHC(O)$NHR^{24}$, and NHC(S)$NHR^{24}$; and $R^{24}$ is H or $C_1$-$C_5$ alkyl.

In yet even further preferred conjugates of Formula III:

$E^1$ and $E^2$ are C(O)NH or NHC(O);

$R^1$ is H;

$R^2$ and $R^3$ are independently selected at each occurrence from: H and phenyl substituted with $R^5$;

$R^5$ is C(=O)OH or $SO_3H$;

$A^1$ is phenylenyl or pyridylenyl;

$A^2$ is a functionalized pyridine analogue;

f, g, h, and i are 0 or 1;

j is 1;

$R^9$, $R^{10}$, $R^{11}$ and $R^{12}$ are independently selected at each occurrence from: H, $R^{13}$, $C_1$-$C_5$ alkyl, and phenyl substituted with $R^{13}$;

$R^{13}$ is independently selected at each occurrence from: OH, C(=O)OH, C(=O)$OCH_3$, and $SO_3H$;

Z is independently selected at each occurrence from: a bond, $CH_2$, O, C(O)NH, NHC(O), $SO_2NH$, and $NHSO_2$;

Q is a biomolecule selected from the group: platelet GPIIb/IIIa receptor binders (including agonists and antagonists), preferably IIb/IIIa receptor ligands, chemotactic compounds (including peptides), $LTB_4$ receptor binders (including agonists and antagonists), somatostatin analogs, vitronectin receptor binders including agonists and antagonists), and matrix metalloproteinase inhibitors;

a is 1 or 2;

a' is 1;

b" is 1 or 2;

$Y^1$ and $Y^2$ are independently selected at each occurrence from: a bond, O, NH, C(O)NH, and NHC(O); and $R^{20}$ and $R^{21}$ are independently selected at each occurrence from: H, $C_1$-$C_5$ alkyl, and phenyl.

In yet further preferred conjugates of Formula III:
A¹ is pyridylenyl;
E¹ is C(O)NH connected to A¹ at the 3-position of the pyridine ring;
E² is NHC(O) connected to A² at the ortho- or meta-position relative to the pyridine-N;
$R^2$ is H;
$R^3$ is 2-sulfonatophenyl;
f, g, h, i, and j are 1;
$R^9$, $R^{10}$, $R^{11}$ and $R^{12}$ are independently selected at each occurrence from: H, $R^{13}$, $C_1$-$C_5$ alkyl, and phenyl;
$R^{13}$ is selected from: C(=O)OH, C(=O)OCH₃, and SO₃H;
Z is selected from: a bond, CH₂, C(O)NH, and NHC(O);
Q is a biomolecule selected from the group: platelet GPIIb/IIIa receptor binders (including agonists and antagonists), preferably IIb/IIIa receptor ligands, LTB₄ receptor binders (including agonists and antagonists), somatostatin analogs, vitronectin receptor binders (including agonists and antagonists), and matrix metalloproteinase inhibitors;
a is 1;
b" is 1;
Y¹ is selected from: a bond, C(O)NH—, and NHC(O);
Y² is a bond; and
$R^{20}$ and $R^{21}$ are H.
In yet even further preferred conjugates of Formula III:
A¹ is pyridylenyl with the hydrazono group connected to A¹ at the ortho-position relative to the pyridine-N;
$R^9$, $R^{10}$, $R^{11}$ and $R^{12}$ are independently selected at each occurrence from: H, $R^{13}$, and $C_1$-$C_5$ alkyl;
$R^{13}$ is selected from: C(=O)OH, and C(=O)OCH₃;
Z is selected from: CH₂, C(O)NH, and NHC(O);
Q is a biomolecule selected from the group: platelet GPIIb/IIIa receptor binders (including agonists and antagonists), preferably IIb/IIIa receptor ligands, somatostatin analogs, vitronectin receptor binders (including agonists and antagonists), and matrix metalloproteinase inhibitors; and
Y¹ is C(O)NH or NHC(O).
In yet further preferred conjugates of Formula III:
$R^9$, $R^{10}$, $R^{11}$ and $R^{12}$ are H or $R^{13}$;
$R^{13}$ is C(=O)OCH₃;
Z is CH₂ or NHC(O); and
Y¹ is C(O)NH.
Preferred conjugates of Formula III include:

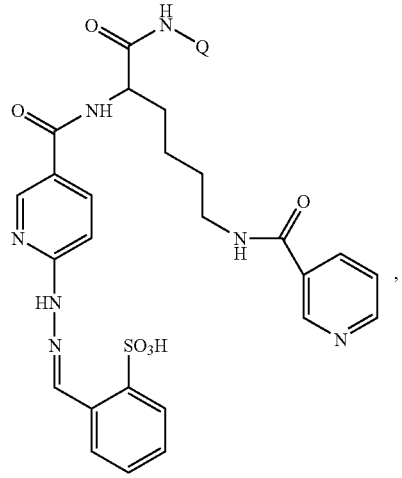

,

-continued

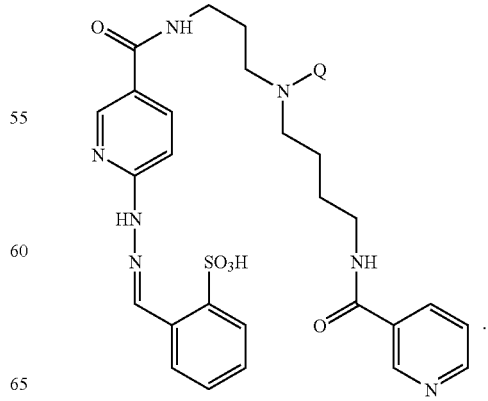

, and

In a fourth aspect, the invention is directed to macrocyclic metal complex-conjugates of Formula IV:

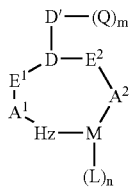          IV or a pharmaceutically acceptable salt thereof, wherein
M is a transition metal radionuclide selected from: $^{99m}$Tc, $^{186}$Re and $^{188}$Re;
L is a coligand capable of stabilizing the macrocyclic metal complex, and is a dioxygen chelating agent, functionalized pyridinecarboxylate, or functionalized aminocarboxylate;
n is 1 or 2;
$E^1$ and $E^2$ are independently selected at each occurrence from: a direct bond, $CH_2$, C(O), C(S), C(O)NH, C(S)NH, NHC(O), NHC(S), NHC(O)NH, NHC(S)NH, $SO_2$, and $SO_2$NH;
Hz is a hydrazino or diazenido group of formula —N($R^1$)N=;
$R^1$ is selected from: a lone pair of electrons, a bond between the two nitrogen atoms, H, $C_1$-$C_{10}$ alkyl substituted with 0-5 $R^4$, $C_2$-$C_{10}$ alkenyl substituted with 0-5 $R^4$, $C_6$-$C_{10}$ aryl substituted with 0-3 $R^4$, and $C_4$-$C_{10}$ heteroaryl substituted with 0-3 $R^4$;
$R^2$ and $R^3$ are independently selected at each occurrence from: H, CN, $CO_2R^5$, $C(O)R^5$, $C(O)N(R^5)_2$, $C_1$-$C_{10}$ alkyl substituted with 0-5 $R^5$, $C_2$-$C_{10}$ alkenyl substituted with 0-5 $R^5$, $C_3$-$C_{10}$ cycloalkyl substituted with 0-5 $R^5$, $C_6$-$C_{10}$ aryl substituted with 0-3 $R^5$, and $C_4$-$C_{10}$ heteroaryl substituted with 0-3 $R^5$; or alternatively $R^2$ and $R^3$ may be taken together to form a $C_3$-$C_{10}$ cycloalkyl or $C_5$-$C_{10}$ cycloalkenyl;
$R^4$ is independently selected at each occurrence from: OH, COOH, $C(O)NH_2$, $SO_3H$, and $SO_2NH_2$
$R^5$ is independently selected at each occurrence from: $C(=O)OR^6$ $C(O)NHR^6$, $C(=O)R^6$, $NHR^6$, $NHC(=O)R^6$, $NHC(=O)NHR^6$, $NHC(=S)NHR^6$, $OR^6$, $OC(=O)R^6$, $OC(=O)OR^6$, $PO(OR^6)_2$, $SR^6$, $SOR^6$, $SO_2R^6$, $SO_3R^6$, and $SO_2NHR^6$;
$R^6$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
$A^1$ is selected from: $C_6$-$C_{10}$ arylenyl substituted with 0-2 $R^7$, and $C_4$-$C_{10}$ heteroarylenyl substituted with 0-2 $R^7$;
$A^2$ is a functionalized imine-N containing $C_3$-$C_{10}$ heterocycle substituted with 0-2 $R^7$;
$R^7$ is independently selected at each occurrence from: $C(=O)OR^8$, $C(O)NHR^8$, $C(=O)R^8$, $NHR^8$, $NHC(=O)R^8$, $NHC(=O)NHR^8$, $NHC(=S)NHR^8$, $OR^8$, $OC(=O)R^8$, $OC(=O)OR^8$, $PO(OR^8)_2$, $SR^8$, $SOR^8$, $SO_2R^8$, $SO_3R^8$, and $SO_2NHR^8$;
$R^8$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
D is a linker of the formula —[(CHR$^9$)$_f$(CHR$^{10}$)$_g$Z(CHR$^{11}$)$_h$(CHR$^{12}$)$_i$]$_j$—,
f is independently an integer from 0 to 5;
g is independently an integer from 0 to 5;
h is independently an integer from 0 to 5;
i is independently an integer from 0 to 5;
j is independently an integer from 1 to 5;
$R^9$, $R^{10}$, $R^{11}$ and $R^{12}$ are independently selected at each occurrence from: H, $R^{13}$, $C_1$-$C_{10}$ alkyl substituted with 0-5 $R^{13}$, $C_2$-$C_{10}$ alkenyl substituted with 0-5 $R^{13}$, $C_3$-$C_{10}$ cycloalkyl substituted with 0-5 $R^{13}$, $C_6$-$C_{10}$ aryl substituted with 0-3 $R^{13}$, $C_4$-$C_{10}$ heteroaryl substituted with 0-3 $R^{13}$;
alternatively $R^9$ and $R^{10}$, $R^9$ and $R^{11}$, $R^9$ and $R^{12}$, $R^{10}$ and $R^{11}$, $R^{10}$ and $R^{12}$ or $R^{11}$ and $R^{12}$, may be taken together to form a $C_3$-$C_{10}$ cycloalkyl or $C_5$-$C_{10}$ cycloalkenyl;
$R^{13}$ is independently selected at each occurrence from: $C(=O)OR^{14}$, $C(O)NHR^{14}$, $C(=O)R^{14}$, $NHR^{14}$, $NHC(=O)R^{14}$, $NHC(=O)NHR^{14}$, $NHC(=S)NHR^{14}$, $OR^{14}$, $OC(=O)R^{14}$, $OC(=O)OR^{14}$, $PO(OR^{14})_2$, $SR^{14}$, $SOR^{14}$, $SO_2R^{14}$, $SO_3R^{14}$, and $SO_2NHR^{14}$;
$R^{14}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
Z is independently selected at each occurrence from: a bond, $CH_2$, C(O), $C(O)NR^{15}$, $C(S)NR^{15}$, $NR^{16}$, $NR^{15}C(O)$, $NR^{15}C(S)$, NHC(=NH)NH, NHC(O)NH, NHC(S)NH, $NR^{15}SO_2$, O, S, SO, $SO_2$, and $SO_2NR^{15}$;
$R^{15}$ is independently selected at each occurrence from: H, $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$ and $C_4$-$C_{10}$ heteroaryl substituted with 0-3 $R^{17}$;
$R^{16}$ is independently selected at each occurrence from: H, $R^{18}$, $C(O)R^{18}$, $SO_2R^{18}$, and $C(O)N(R^{18})$;
$R^{17}$ is independently selected at each occurrence from: OH, $C(=O)OR^{19}$, $C(O)NHR^{19}$, $C(=O)R^{19}$, $NHR^{19}$, $NHC(=O)R^{19}$, $NHC(=O)NHR^{19}$, $NHC(=S)NHR^{19}$, $OR^{19}$, $OC(=O)R^{19}$, $OC(=O)OR^{19}$, $PO(OR^{19})_2$, $SO_2R^{19}$, $SO_3R^{19}$, and $SO_2NHR^{19}$;
$R^{18}$ is independently selected at each occurrence from: $C_1$-$C_{10}$ alkyl substituted with 0-5 $R^{17}$, $C_2$-$C_{10}$ alkenyl substituted with 0-5 $R^{17}$, $C_3$-$C_{10}$ cycloalkyl substituted with 0-5 $R^{17}$, $C_6$-$C_{10}$ aryl substituted with 0-3 $R^{17}$, and $C_4$-$C_{10}$ heteroaryl substituted with 0-3 $R^{17}$;
$R^{19}$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
Q is a biologically active group;
m is an integer of 1 to 20;
D' is a pharmacokinetic modifier having the formula:

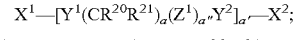

$X^1$ is [(CH$_2$)$_b$Z$^1$]$_{b'}$-(CR$^{20}$R$^{21}$)$_{b''}$;
$X^2$ is (CR$^{20}$R$^{21}$)$_{b''}$-[Z$^1$(CH$_2$)$_b$]$_{b'}$;
a is independently an integer of 0 to 10;
a' is independently an integer of 0 to 10;
a" independently an integer of 0 to 1;
b is independently an integer of 0 to 10;
b' independently an integer of 0 to 1;
b" is independently an integer of 0 to 10;
$Y^1$ and $Y^2$, at each occurrence, are independently selected from: a bond, O, $NR^{21}$, C=O, C(=O)O, OC(=O)O, C(=O)NH, C=NR$^{21}$, S, SO, $SO_2$, $SO_3$, NHC(=O), (NH)$_2$C(=O), and (NH)$_2$C=S;
$Z^1$ is independently selected at each occurrence from: $C_6$-$C_{14}$ saturated, partially saturated, or aromatic carbocyclic ring system, substituted with 0-4 $R^{22}$; and a heterocyclic ring system, optionally substituted with 0-4 $R^{22}$;

$R^{20}$ and $R^{21}$ are independently selected at each occurrence from: H, $C_1$-$C_{10}$ alkyl substituted with 0-5 $R^{23}$, and aryl is substituted with 0-5 $R^{23}$;

$R^{22}$ and $R^{23}$ are independently selected at each occurrence from the group: OH, $NHR^{24}$, $C(=O)R^{24}$, $OC(=O)R^{24}$, $OC(=O)OR^{24}$, $C(=O)OR^{24}$, $C(=O)NR^{24}$, —CN, $SR^{24}$, $SOR^{24}$, $SO_2R^{24}$, $NHC(=O)R^{24}$, $NHC(=O)NH\ R^{24}$, and $NHC(=S)NH\ R^{24}$;

alternatively, when m is greater than 1, $R^{23}$ is independently selected at each occurrence from the group: O, $NR^{24}$, C=O, $C(=O)O$, $OC(=O)O$, $C(=O)N$, $C=NR^{24}$, S, SO, $SO_2$, $SO_3$, $NHC(=O)$, $(NH)_2C(=O)$, and $(NH)_2C=S$; and $R^{24}$ is independently selected at each occurrence from the group: H, $C_1$-$C_6$ alkyl, benzyl, and phenyl.

In preferred macrocyclic metal complex-conjugates of Formula IV:

M is $^{99m}Tc$;

L is a functionalized aminocarboxylate;

n is 1;

$E^1$ and $E^2$ are independently selected at each occurrence from: C(O)NH, NHC(O), NHC(O)NH, NHC(S)NH, and $SO_2NH$;

$R^1$ is selected from: a lone pair of electrons, H, $C_1$-$C_{10}$ alkyl substituted with 0-3 $R^4$, $C_2$-$C_{10}$ alkenyl substituted with 0-3 $R^4$, $C_6$-$C_{10}$ aryl substituted with 0-2 $R^4$, and $C_4$-$C_{10}$ heteroaryl substituted with 0-2 $R^4$;

$R^4$ is independently selected at each occurrence from: OH, COOH, and $SO_3H$;

$R^7$ is independently selected at each occurrence from: $C(=O)OH$, $C(O)NHR^8$, $NHR^8$, $NHC(=O)R^8$, $SO_3H$, and $SO_2NHR^8$;

$R^8$ is independently selected at each occurrence from: H, $C_1$-$C_{10}$ alkyl, $C_6$-$C_{10}$ aryl, and $C_4$-$C_{10}$ heteroaryl;

f is independently an integer of 0 to 3;

g is independently an integer of 0 to 3;

h is independently an integer of 0 to 3;

i is independently an integer of 0 to 3;

j is independently an integer of 1 to 3;

$R^9$, $R^{10}$, $R^{11}$ and $R^{12}$ are independently selected at each occurrence from: H, $R^{13}$, $C_1$-$C_{10}$ alkyl substituted with 0-3 $R^{13}$, $C_2$-$C_{10}$ alkenyl substituted with 0-3 $R^{13}$, $C_6$-$C_{10}$ aryl substituted with 0-2 $R^{13}$, and $C_4$-$C_{10}$ heteroaryl substituted with 0-2 $R^{13}$ $R^{13}$ is independently selected at each occurrence from: OH, $C(=O)OH$, $C(O)OR^{14}$, $C(O)NHR^{14}$, $NHR^{14}$, $NHC(=O)R^{14}$, $SO_2R^{14}$, and $SO_2NHR^{14}$;

$R^{14}$ is independently selected at each occurrence from: H, $C_1$-$C_{10}$ alkyl, $C_6$-$C_{10}$ aryl, and $C_4$-$C_{10}$ heteroaryl;

Z is independently selected at each occurrence from: a bond, $CH_2$, $C(O)NR^{15}$, $NR^{16}$, $NR^{15}C(O)$, $NR^{15}SO_2$, O, $SO_2$, and $SO_2NR^{15}$;

$R^{15}$ is independently selected at each occurrence from: H, $C_1$-$C_{10}$ alkyl substituted with 0-3 $R^{17}$, $C_2$-$C_{10}$ alkenyl substituted with 0-3 $R^{17}$, $C_6$-$C_{10}$ aryl substituted with 0-2 $R^{17}$, and $C_4$-$C_{10}$ heteroaryl substituted with 0-2 $R^{17}$;

$R^{16}$ is independently selected at each occurrence from: H, $R^{18}$, $C(O)R^{18}$, and $SO_2R^{18}$;

$R^{17}$ is independently selected at each occurrence from: OH, $C(=O)OH$, $C(O)NHR^{19}$, $NHR^{19}$, $NHC(=O)R^{19}$, $OR^{19}$, $SO_2R^{19}$, $SO_3H$, and $SO_2NHR^{19}$;

$R^{18}$ is independently selected at each occurrence from: $C_1$-$C_{10}$ alkyl substituted with 0-3 $R^{17}$, $C_2$-$C_{10}$ alkenyl substituted with 0-3 $R^{17}$, $C_6$-$C_{10}$ aryl substituted with 0-2 $R^{17}$, and $C_4$-$C_{10}$ heteroaryl substituted with 0-2 $R^{17}$;

$R^{19}$ is independently selected at each occurrence from: H, $C_1$-$C_{10}$ alkyl, $C_6$-$C_{10}$ aryl, and $C_4$-$C_{10}$ heteroaryl;

Q is a biomolecule selected from the group: platelet GPIIb/IIIa receptor binders (including agonists and antagonists), preferably IIb/IIIa receptor ligands, fibrin binding compounds (including peptides), leukocyte binding compounds, chemotactic compounds (peptides), $LTB_4$ receptor binders (including agonists and antagonists), somatostatin analogs, selectin binding compounds, vitronectin receptor binders (including agonists and antagonists), kinase inhibitors (including tyrosine kinase inhibitors), matrix metalloproteinase inhibitors, oligonucleotides, fatty acids, nitroimidazoles, and carbohydrates;

m is an integer from 1 to 3;

a is independently an integer from 0 to 5;

a' is independently an integer from 0 to 5;

a", b, and b' are 0;

b" is independently an integer from 0 to 5;

$Y^1$ and $Y^2$, at each occurrence, are independently selected from: a bond, O, $NR^{21}$, C=O, $C(=O)O$, $OC(=O)O$, $C(=O)NH$—, $C=NR^{21}$, $SO_2$, $NHC(=O)$, $(NH)_2C(=O)$, and $(NH)_2C=S$;

$R^{20}$ and $R^{21}$ are independently selected at each occurrence from: H, $C_1$-$C_5$ alkyl substituted with 0-3 $R^{23}$, and aryl substituted with 0-3 $R^{23}$;

$R^{23}$ is independently selected at each occurrence from the group: OH, $NHR^{24}$, $C(O)R^{24}$, $C(O)OR^{24}$, $C(O)NR^{24}$, $SR^{24}$, $SO_2R^{24}$, $NHC(O)R^{24}$, $NHC(O)NHR^{24}$, and $NHC(S)NHR^{24}$;

alternatively, when m is greater than 1, $R^{23}$ is independently selected at each occurrence from the group: O, $NR^{24}$, $C(O)O$, $OC(O)O$, $C(O)N$, $C=NR^{24}$, $SO_2$, NHC(O), $(NH)_2C(O)$, and $(NH)_2C(S)$; and $R^{24}$ is independently selected at each occurrence from the group: H, $C_1$-$C_5$ alkyl, benzyl, and phenyl.

In more preferred macrocyclic metal complex-conjugates of Formula IV:

$E^1$ and $E^2$ are independently selected at each occurrence from: C(O)NH, NHC(O), and $SO_2NH$;

$R^1$ is selected from: a lone pair of electrons, H, $C_1$-$C_{10}$ alkyl and $C_4$-$C_6$ heteroaryl;

$A^1$ is selected from: phenylenyl, furylenyl, thienylenyl, imidazolylenyl, thiazolylenyl, and pyridylenyl;

$A^2$ is a functionalized imidazoles or pyridine analogue;

$R^7$ is independently selected at each occurrence from: $C(=O)OH$, $C(O)NH_2$, $SO_3H$, and $SO_2NH_2$;

f is independently an integer of 0 to 2;

g is independently an integer of 0 to 2;

h is independently an integer of 0 to 2;

i is independently an integer of 0 to 2;

j is independently an integer of 1 to 2;

$R^9$, $R^{10}$, $R^{11}$ and $R^{12}$ are independently selected at each occurrence from: H, $R^{13}$, $C_1$-$C_5$ alkyl substituted with 0-2 $R^{13}$, $C_6$-$C_{10}$ aryl substituted with 0-2 $R^{13}$, and $C_4$-$C_{10}$ heteroaryl substituted with 0-2 $R^{13}$;

$R^{13}$ is independently selected at each occurrence from: OH, $C(=O)OH$, $C(=O)OCH_3$, $C(O)NH_2$, $SO_3H$, and $SO_2NH_2$;

Z is selected from: a bond, $CH_2$, O, $C(O)NR^{15}$, $NR^{16}$, $NR^{15}C(O)$, $SO_2NR^{15}$, and $NR^{15}SO_2$;

$R^{15}$ is independently selected at each occurrence from: H, $C_1$-$C_5$ alkyl substituted with $R^{17}$, $C_6$-$C_{10}$ aryl substituted with $R^{17}$, and $C_4$-$C_{10}$ heteroaryl substituted with $R^{17}$;

$R^{16}$ is $C(O)R^{18}$ or $SO_2R^{18}$;

$R^{17}$ is independently selected at each occurrence from: OH, C(=O)OH, C(O)NH$_2$, and SO$_3$H;

$R^{18}$ is independently selected at each occurrence from: C$_1$-C$_5$ alkyl, C$_2$-C$_5$ alkenyl, C$_6$-C$_{10}$ aryl, and C$_4$-C$_{10}$ heteroaryl;

Q is a biomolecule selected from the group: platelet GPIIb/IIIa receptor binders (including agonists and antagonists), preferably IIb/IIIa receptor ligands, fibrin binding compounds (including peptides), chemotactic compounds (including peptides), LTB$_4$ receptor binders (including agonists and antagonists), somatostatin analogs, vitronectin receptor binders (including agonists and antagonists), and matrix metalloproteinase inhibitors;

m is 1;

a is independently an integer from 1 to 3;

a' is independently an integer from 1 to 3;

b" is independently an integer from 1 to 3;

$Y^1$ and $Y^2$, at each occurrence, are independently selected from: a bond, O, NH, C(O)NH—, NHC(O), and (NH)$_2$C=S;

$R^{20}$ and $R^{21}$ are independently selected at each occurrence from: H, C$_1$-C$_5$ alkyl substituted with 0-2 $R^{23}$, and aryl substituted with 0-2 $R^{23}$;

$R^{23}$ is independently selected at each occurrence from the group: H, NHR$^{24}$, C(O)NR$^{24}$, NHC(O)R$^{24}$, NHC(O)NHR$^{24}$, and NHC(S)NHR$^{24}$; and $R^{24}$ is H or C$_1$-C$_5$ alkyl.

In even more preferred macrocyclic metal complex-conjugates of Formula IV:

$E^1$ and $E^2$ are C(O)NH or NHC(O);

$R^1$ is a lone pair of electrons or H;

$A^1$ is phenylenyl or pyridylenyl;

$A^2$ is a functionalized pyridine analogue;

f, g, h, and i are 0 or 1;

j is 1;

$R^9$, $R^{10}$, $R^{11}$ and $R^{12}$ are independently selected at each occurrence from: H, $R^{13}$, C$_1$-C$_5$ alkyl, and phenyl substituted with $R^{13}$;

$R^{13}$ is independently selected at each occurrence from: OH, C(=O)OH, C(=O)OCH$_3$, and SO$_3$H;

Z is independently selected at each occurrence from: a bond, CH$_2$, O, C(O)NH, NHC(O), SO$_2$NH, and NHSO$_2$;

Q is a biomolecule selected from the group: platelet GPIIb/IIIa receptor binders (including agonists and antagonists), preferably IIb/IIIa receptor ligands, LTB$_4$ receptor binders (including agonists and antagonists), somatostatin analogs, vitronectin receptor binders (including agonists and antagonists), and matrix metalloproteinase inhibitors;

a is 1 or 2;

a' is 1;

b" is 1 or 2;

$Y^1$ and $Y^2$ are independently selected at each occurrence from: a bond, O, NH, C(O)NH, and NHC(O); and $R^{20}$ and $R^{21}$ are H or C$_1$-C$_5$ alkyl.

In yet further preferred macrocyclic metal complex-conjugates of Formula IV:

$A^1$ is pyridylenyl;

$E^1$ is C(O)NH connected to $A^1$ at the 3-position of the pyridine ring;

$E^2$ is NHC(O) connected to $A^2$ at the ortho- or meta-position relative to the pyridine-N;

f, g, h, i, and j are 1;

$R^9$, $R^{10}$, $R^{11}$ and $R^{12}$ are independently selected at each occurrence from: H, $R^{13}$, C$_1$-C$_5$ alkyl, and phenyl;

$R^{13}$ is selected from: C(=O)OH, C(=O)OCH$_3$, and SO$_3$H;

Z is selected from: a bond, CH$_2$, C(O)NH and NHC(O);

Q is a biomolecule selected from the group: platelet GPIIb/IIIa receptor binders (including agonists and antagonists), preferably IIb/IIIa receptor ligands, LTB$_4$ receptor binders (including agonists and antagonists), somatostatin analogs, vitronectin receptor binders (including agonists and antagonists), and matrix metalloproteinase inhibitors;

a is 1;

b" is 1;

$Y^1$ is selected from: a bond, C(O)NH, and NHC(O);

$Y^2$ is a bond; and $R^{20}$ and $R^{21}$ are H.

In yet even further preferred macrocyclic metal complex-conjugates of Formula IV:

$A^1$ is pyridylenyl with the hydrazino or diazenido group being connected to $A^1$ at the ortho-position relative to the pyridine-N;

$R^9$, $R^{10}$, $R^{11}$ and $R^{12}$ are independently selected at each occurrence from: H, $R^{13}$, and C$_1$-C$_5$ alkyl;

$R^{13}$ is selected from: C(=O)OH, and C(=O)OCH$_3$; and

Z is selected from: CH$_2$, C(O)NH and NHC(O);

Q is a biomolecule selected from the group: platelet GPIIb/IIIa receptor binders (including agonists and antagonists), preferably IIb/IIIa receptor ligands, somatostatin analogs, vitronectin receptor binders (including agonists and antagonists), and matrix metalloproteinase inhibitors; and $Y^1$ is C(O)NH or NHC(O);

In yet further preferred macrocyclic metal complex-conjugates of Formula IV:

$R^9$, $R^{10}$, $R^{11}$ and $R^{12}$ are H or $R^{13}$;

$R^{13}$ is C(=O)OCH$_3$;

Z is CH$_2$ or C(O)NH; and $Y^1$ is C(O)NH.

Preferred macrocyclic metal complex-conjugates of Formula IV include:

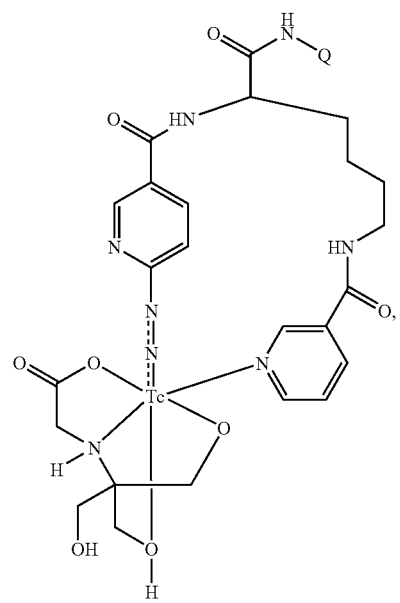

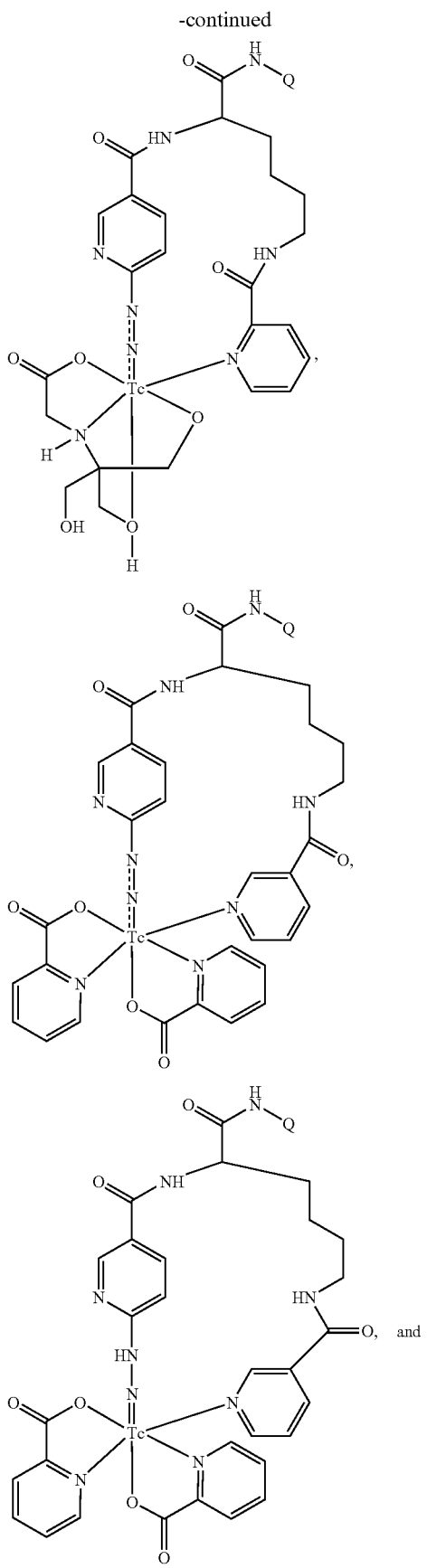

In other embodiments, the invention is directed to radiopharmaceutical compositions, comprising said macrocyclic metal complex-conjugate of Formula III.

In yet another embodiment, the invention is directed to kits for forming a macrocyclic metal complex radiopharmaceutical, comprising:
   a conjugate of Formula III;
   a coligand selected from the group: dioxygen chelating agent, functionalized pyridinecarboxylate, and functionalized aminocarboxylate, preferably tricine;
   a reducing agent, preferably stannous chloride; and
   instructions for contacting said compound, said coligand and said reducing agent with a radionuclide, preferably [$^{99m}$Tc]pertechnetate, under conditions sufficient to produce said macrocyclic metal complex radiopharmaceutical.

In yet another embodiment, the invention is directed to kits for forming a macrocyclic metal complex-conjugate radiopharmaceutical, comprising:
   a predetermined quantity of a sterile, pharmaceutically-acceptable conjugate of Formula III;
   a predetermined quantity of sterile, pharmaceutically-acceptable stabilizing coligand selected from the group: dioxygen chelating agent, functionalized pyridinecarboxylate, and functionalized aminocarboxylate, preferably tricine;
   a predetermined quantity of a sterile, pharmaceutically-acceptable reducing agent, preferably stannous chloride; and
   optionally, a predetermined quantity of one or more sterile, pharmaceutically acceptable components selected from the group: buffers, lyophilization aids, stabilization aids, solubilization aids and bacteriostats.

In other embodiments, the invention is directed to diagnostic compositions, comprising:
   a diagnostically-effective amount of the conjugate of Formula II; and
   a pharmaceutically acceptable carrier.

In other embodiments, the invention is directed to methods for radioimaging a patient, comprising the steps of:
   administering to said patient an effective amount of said conjugate of Formula III; and scanning said patient using a radioimaging device.

In yet other embodiments, the invention is directed to methods for visualizing sites of platelet deposition in a patient by radioimaging, comprising the steps of:
- administering to said patient an effective amount of a conjugate of Formula III; and
- scanning said patient using a radioimaging device;
- wherein Q is a IIb/IIIa receptor ligand or fibrin binding compound.

In another embodiment, the invention is directed to methods of determining platelet deposition in a patient, comprising the steps of:
- administering to said patient an effective amount of a conjugate of Formula III; and
- imaging said patient;
- wherein Q is a IIb/IIIa receptor ligand or fibrin binding compound.

In other embodiments, the invention is directed to methods of diagnosing a disorder associated with platelet deposition in a patient, comprising the steps of:
- administering to said patient an effective amount of a conjugate of Formula III; and
- imaging said patient;
- wherein Q is a IIb/IIIa receptor ligand or fibrin binding compound.

In another embodiment, the invention is directed to methods of diagnosing thromboembolic disorders or atherosclerosis in a patient, comprising the steps of:
- administering to said patient an effective amount of a conjugate of Formula III; and
- generating a radioimage of at least a part of said patient's body;
- wherein Q is a IIb/IIIa receptor ligand or fibrin binding compound.

In yet another embodiment, the invention is directed to methods of diagnosing infection, inflammation or transplant rejection in a patient, comprising the steps of:
- administering to said patient an effective amount of a conjugate of Formula III; and
- generating a radioimage of at least a part of said patient's body;
- wherein Q is selected from the group consisting of a leukocyte binding compound, a chemotactic compound (including peptide), and a $LTB_4$ receptor binder (including agonist or antagonist).

In another preferred embodiment, the invention is directed to methods of detecting new angiogenic vasculature in a patient, comprising the steps of:
- administering to said patient an effective amount of a conjugate of Formula III; and
- generating a radioimage of at least a part of said patient's body;
- wherein Q is a vitronectin receptor binder (including agonist or antagonist), preferably IIb/IIIa receptor ligands, a somatostatin analog, or a growth factor receptor binder (including agonist or antagonist).

It is appreciated that certain features of the invention, which are, for clarity, described in the context of separate embodiments, may also be provided in combination in a single embodiment. Conversely, various features of the invention, which are for brevity, described in the context of a single embodiment, may also be provided separately or in any subcombination.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then two hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0-2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with one or more halogen (for example —$C_vF_w$ where v is 1 to 3 and w is 1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl"

is intended to include saturated ring groups, such as cyclopropyl, cyclobutyl, or cyclopentyl. "Alkenyl" is intended to include hydrocarbon chains of either a straight or branched configuration and one or more unsaturated carbon-carbon bonds that may occur in any stable point along the chain, such as ethenyl and propenyl. "Alkynyl" is intended to include hydrocarbon chains of either a straight or branched configuration and one or more triple carbon-carbon bonds that may occur in any stable point along the chain, such as ethynyl and propynyl.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio, *The Peptides,* 1983 5: 342429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotyrosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "peptide" as used herein means a linear compound that consists of two or more amino acids (as defined herein) that are linked by means of a peptide bond. A "peptide" as used in the presently claimed invention is intended to refer to a moiety with a molecular weight of less than about 10,000 Daltons, preferable less than about 5,000 Daltons, and more preferably less than about 2,500 Daltons. The term "peptide" also includes compounds containing both peptide and non-peptide components, such as pseudopeptide or peptidomimetic residues or other non-amino acid components. Such a compound containing both peptide and non-peptide components may also be referred to as a "peptide analog."

A "pseudopeptide" or "peptidomimetic" is a compound that mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue. A "pseudopeptide residue" means that portion of a pseudopeptide or peptidomimetic that is present in a peptide.

The term "peptide bond" means a covalent amide linkage formed by loss of a molecule of water between the carboxyl group of one amino acid and the amino group of a second amino acid.

The term "pseudopeptide bonds" includes peptide bond isosteres that may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic or diagnostic agent.

A radiopharmaceutical kit is used for routine preparation of the metal complex radiopharmaceutical of a specific chelant. The kit formulation usually contains the chelant or chelant-biomolecule (BFC-BM) conjugate, a coligand or transferring ligand, if needed, a reducing agent, and other optional components, such as buffer, lyophilization aid, stabilization aid, solubilizing aids, and bacteriostats. A radiopharmaceutical composition usually contains the metal complex radiopharmaceutical, a buffer, a stabilization aid to prevent autoradiolysis, and a bacteriostats. If radiopharmaceutical is prepared using the kit formulation, the radiopharmaceutical composition may contain the metal complex radiopharmaceutical and kit components, including unlabeled chelant or chelant-biomolecule (BFC-BM) conjugate, coligand or transferring ligand, a reducing agent, buffer, lyophilization aid, stabilization aid, solubilizing aids, and bacteriostats.

One aspect of the present invention is to provide a new chelant containing an aromatic hydrazine moiety and a monodentate triarylphosphine moiety. The new chelant described in this invention is designed in such a way that the aromatic hydrazine moiety and the monodentate triarylphosphine moiety are covalently connected via a linker. The aromatic hydrazine moieties include derivatives of hydrazinobenzene, hydrazinothiazole, hydrazinoimidazole, and more preferably hydrazinopyridine. The aromatic hydrazine moieties can be free hydrazine or in the protected forms by forming the corresponding hydrazones. The aryl groups in the monodentate triarylphosphine moiety include substituted phenyl, furyl, thienyl, and pyridyl. The number of heteroaryl groups in the monodentate triarylphosphine moiety can be varied from 0 to 3. The linker between the hydrazine moiety and phosphine-P atom may be a simple alkylene chain or a small peptide sequence. The chelant is able to form a macrocyclic chelate ring in bonding to the Tc or Re.

The site for attachment of the linker may vary for both the aromatic hydrazine moiety and the triarylphosphine moiety. The attachment site on the triarylphosphine moiety also depends on the choice of the attachment site at the aromatic hydrazine moiety. For example, the site for attaching the linker onto the triphenylphosphine moiety can be ortho (2-position), meta (3-position), or para (4-position) relative to the C—P bond. If the aromatic hydrazine moiety is 6-hydrazinonicotinamide, in which the amide group (—CONH—) is at the para position relative to the hydrazine moiety, the preferred position for attachment of the linker to the triphenylphosphine moiety is para (4-position). The attachment site of the linker can also be at the α-N of the aromatic hydrazine moiety.

The organic hydrazines are not stable to oxidation, particularly under basic conditions, and react readily with aldehydes or ketones, which are extracted from various plastic and rubber materials. This makes it very difficult to maintain the purity and the stability of the hydrazine-containing chelants. U.S. Pat. No. 5,206,370 discloses the use of a lower alkyl hydrazone (propylaldehyde hydrazone) to stabilize hydrazine-modified proteins. Although its use can prevent the cross-reaction of the hydrazine with other reactive groups on the protein, the propylaldehyde hydrazone can be displaced by other aldehydes, formaldehyde in particular, and ketones to form different hydrazones. U.S. Pat. No. 5,750,088 and U.S. Pat. No. 6,015,904 discloses the use of stable hydrazones useful for preparation of $^{99m}$Tc-labeled hydrazine-modified bioconjugates. It was found that for a hydrazone to be stable in aqueous solution there must be a conjugated π-system (Harris, et al., *Bioconjugate Chem.* 1999, 10, 808). Examples of the chelants described in this invention are stable hydrazones derived from 2-sulfonato-benzaldehyde.

Another aspect of the present invention is to provide a macrocyclic metal complex radiopharmaceutical with high solution stability. The macrocyclic metal complex radiopharmaceutical is comprised of the chelant having an aromatic hydrazine moiety and a monodentate triarylphosphine group, and a stabilizing coligand. The aromatic hydrazine moiety and the monodentate triarylphosphine group are covalently connected via a linker. In doing so, the triarylphosphine moiety can readily coordinate to the Tc or Re once the aromatic hydrazine moiety is bonded to the Tc or Re; thereby eliminating the need for a large excess of water-soluble phosphine coligand as in the ternary ligand system reported in Edwards, et al., *Bioconjugate Chem.* 1997, 8, 146).

The incorporation of the metallic radionuclide into the macrocyclic framework offers many opportunities for the design of new metal complex radiopharmaceuticals by modifying the coordination environment around the metal with a variety of chelant and coligand. For example, the aromatic hydrazine can be analogues of hydrazinobenzene, hydrazinothiazole, hydrazinoimidazole, or more preferably hydrazinopyridine. The aryl groups in the monodentate triarylphosphine moiety include substituted phenyl, furyl, thienyl, or pyridine. The number of heteroaryl groups in the monodentate triarylphosphine moiety can be varied from 0 to 3. Since the new chelant is most likely bidentate, a coligand is needed to complete the coordination sphere of the metal, such as technetium or rhenium. The new chelant forms a macrocyclic metal complex when used in combination with a coligand. Because of the macrocyclic effect, the bonding between the phosphine-P and the Tc is strong and the resulting macrocyclic metal complex has very high solution stability. On the other hand, the bonding of the aromatic hydrazine moiety to the metal can dramatically increase the "local concentration" of the monodentate triarylphosphine group around the metal, thereby increasing the radiolabeling kinetics and the radiolabeling efficiency of the new chelant.

The metallic radionuclide, M, is selected from the group: $^{99m}$Tc, $^{186}$Re and $^{188}$Re. For diagnostic purposes $^{99m}$Tc is the preferred isotope. Its 6-hour half-life and 140 keV gamma ray emission energy are almost ideal for gamma scintigraphy using equipment and procedures well established for those skilled in the art. The rhenium isotopes also have gamma ray emission energies that are compatible with gamma scintigraphy, however, they also emit high energy beta particles that are more damaging to living tissues. These beta particle emissions can be utilized for therapeutic purposes, for example, cancer radiotherapy.

The related chemistry, medical applications, and radiolabeling with $^{186/188}$Re by direct and indirect methods have been reviewed (Fritzberg, et al., *Pharmaceutical Res.* 1988, 5, 325; Liu et al., *Bioconjugate Chem.* 1997, 8, 621; Dilworth, J. R. and Parrott, S. J. *Chem. Soc. Rev.* 1998, 27, 43).

The Hz group in the macrocyclic metal complex is termed a hydrazido (formula —N(R$^1$)—N═), or diazenido (formula: —N═N$^+$═ or —N═N(H)—) group and serves as one point of attachment of the metallic radionuclide to the chelant. A diazenido group can be either terminal (only one atom of the group is bound to the radionuclide) or chelating. In order to have a chelating diazenido group at least one other atom of the group, located on the aromatic ring, A$^1$, must also be bound to the radionuclide. The atoms bound to the metal are termed donor atoms.

The coordination sphere of the metal includes all the ligands or groups bound to the metallic radionuclide. For the metal complex to be stable, the metal atom typically has a coordination number (number of donor atoms) comprised of an integer greater than or equal to 4 and less than or equal to 8; that is there are 4 to 8 atoms bound to the metal and it is said to have a complete coordination sphere. The coordination number for a stable metal complex is determined by the identity and oxidation state of the metallic radionuclide, and the type of donor atoms. In case of technetium and rhenium, the most common coordination number is 5 or 6. If the chelant does not provide all of the atoms necessary to stabilize the metallic radionuclide by completing its coordination sphere, a coligand is needed to complete the coordination sphere. The coligand can be terminal or chelating. If the coligand is a chelating agent, or chelator, it can be bidentate, tridentate, or tetradentate depending on the donor atoms available for coordination to the metal center.

A large number of chelators can serve as coligands, the choice of which is determined by a variety of factors such as the ease of synthesis of the metal complex, chemical and physical properties of the coligand, the radiolabeling efficiency, the radiolabeling yield, and the number of isomeric forms of the resulting metal complex, the ability to administer said coligand to a patient without adverse physiological consequences to said patient, and the compatibility of the coligand in a lyophilized kit formulation. The charge and lipophilicity of the coligand will affect the charge and lipophilicity of the metal complex. For example, the use of 4,5-dihydroxy-1,3-benzene disulfonate results in metal complexes with an additional two anionic groups because the sulfonate groups will be anionic under physiological conditions. The use of N-alkyl substituted 3,4-hydroxypyridinones results in metal complexes with varying degrees of lipophilicity depending on the size of the alkyl substituents.

The macrocyclic metal complex of the present invention is comprised of the chelant having an aromatic hydrazine moiety and a monodentate triarylphosphine group, and a stabilizing coligand (L). The chelant has two donor atoms: one from the hydrazine moiety and the other from the triarylphosphine group. The coligand can be bidentate with two hard donor atoms such as oxygen and amine nitrogen (sp$^3$ hydribidized) or tetradentate with four donor atoms capable of occupying four sites in the coordination sphere of the metallic radionuclide. Examples of stabilizing coligands include but are not limited to dioxygen chelating agents, functionalized pyridinecarboxylates, and functionalized aminocarboxylates. A large number of such ligands are available from commercial sources.

Dioxygen-containing coligands include but are not limited to: glycine, glucoheptonate, gluconate, 2-hydroxyisobutyrate, lactate, tartrate, mannitol, glucarate, maltol, Kojic acid, 2,2-bis(hydroxymethyl)propionic acid, 4,5-dihydroxy-1,3-benzene disulfonate, or substituted 1,2 or 3,4 hydroxypyridinones. The names for the ligands in these examples refer to either the protonated or non-protonated forms of the ligands.

Functionalized tetradentate aminocarboxylates include those that have a combination of amine nitrogen and oxygen donor atoms. Examples include but are not limited to: N-[tris(hydroxymethyl)methyl]glycine (tricine), N-[bis(hydroxymethyl)methyl]glycine (dicine), N,N-bis(2-hydroxyethyl)glycine (bicine), nitrilotriacetic acid (NTA), N-(2-hydroxyethyl)iminodiacetic acid (HIDA), ethylenediamine-N,N'-diacetic acid (EDDA), N-(hydroxyethyl)-ethylenediamine triacetic acid (HEDTA). (The names for the ligands in these examples refer to either the protonated or non-protonated forms of the ligands.)

A series of functionalized aminocarboxylates are disclosed in U.S. Pat. No. 5,350,837, herein incorporated by reference, that result in improved the $^{99m}$Tc-labeling rate of hydrazino-modified proteins. Preferred coligands are functionalized aminocarboxylates, which are derivatives of glycine; the most preferred is tricine.

The structure of a particular macrocyclic metal complex described in the present invention will depend on the identity of the chelant, the identity of the coligand, and the identity of the radionuclide M. The number of the coligand in a specific macrocyclic metal complex will depend on the number of donor atoms in the stabilizing coligand. If the coligand is bidentate, at least two said coligands are needed to complete the coordination sphere of the metallic radionuclide. If the coligand is tetradentate, one said coligand is sufficient to complete the coordination sphere of the metallic radionuclide, such as $^{99m}$Tc.

Another aspect of the present invention is to provide a method for preparing the macrocyclic metal complex radiopharmaceuticals comprised of the chelants having an aromatic hydrazine moiety and a monodentate triarylphosphine group, and a stabilizing coligand.

The technetium and rhenium radionuclides are preferably in the chemical form of [$^{99m}$Tc]pertechnetate or [$^{186/188}$Re] perrhenate and a pharmaceutically acceptable cation. The [$^{99m}$Tc]pertechnetate salt form is preferably sodium [$^{99m}$Tc] pertechnetate such as obtained from commercial $^{99m}$Tc generators. The amount of [$^{99m}$Tc]pertechnetate used to prepare the macrocyclic metal complexes of the present invention can range from about 1 mCi to about 1000 mCi, or more preferably from about 1 mCi to about 100 mCi. Since there is no effective chemistry that can be used to attach the [$^{99m}$Tc]pertechnetate anion to a small biomolecule, the [$^{99m}$Tc]pertechnetate has to be reduced by a reducing agent to a lower oxidation state in order to produce a stable macrocyclic $^{99m}$Tc complex or to a reactive intermediate complex from which $^{99m}$Tc can be easily transferred to the new chelant to form the expected macrocyclic $^{99m}$Tc complex. The rhenium chemistry is very similar to technetium chemistry due to the periodic relationship. Therefore, the methods used for molecules labeled with $^{99m}$Tc should apply to those labeled with $^{186/188}$Re.

Suitable reducing agents for the synthesis of the macrocyclic metal complex radiopharmaceuticals of the present invention include stannous salts, dithionite or bisulfite salts, borohydride salts, and formamidinesulfinic acid, wherein the salts are of any pharmaceutically acceptable form. The preferred reducing agent is a stannous salt. The amount of a reducing agent used can range from about 0.001 mg to about 10 mg, or more preferably from about 0.005 mg to about 1 mg.

Synthesis of the macrocyclic metal complex radiopharmaceutical can be achieved by either one-step or two-step approach. In the two-step approach, the [$^{99m}$Tc]pertechnetate is first reduced by a reducing agent, such as stannous chloride, to form an intermediate $^{99m}$Tc-coligand complex (Larsen, et al., *Bioconjugate Chem.* 1995, 6, 635; Edwards, et al., *Bioconjugate Chem.* 1997, 8, 146). The intermediate $^{99m}$Tc-coligand complex is then reacted with the new chelant to form the expected macrocyclic $^{99m}$Tc complex. In the one-step approach, the macrocyclic $^{99m}$Tc complex is prepared by reacting the [$^{99m}$Tc]pertechnetate directly with the chelant in the presence of stannous chloride and an excess of a stabilizing coligand. The radiolabeling can be performed at temperatures from room temperature to about 100° C., depending on the reaction kinetics, and the choice of the aromatic hydrazine moiety. If the hydrazine is in its hydrazone form, the radiolabeling should be performed at temperatures ranging from about 50° C. to about 100° C.

The total time of preparation will vary depending on the metallic radionuclide, the identities and amounts of the reactants and the procedure used for the preparation. The preparations may be complete, resulting in >80% yield of the macrocyclic metal complex, in one minute or may require more time. After the radiolabeling, the resulting reaction mixture may optionally be purified using one or more chromatographic methods, such as Sep-Pack or high performance liquid chromatography (HPLC). The preferred methods are those, in which the macrocyclic $^{99m}$Tc complex is prepared in high yield and high radiochemical purity without post-labeling purification.

The $^{99m}$Tc-labeling efficiency of the new chelant depends on the identity of the hydrazine moiety in said chelant. The preferred aromatic hydrazine is hydrazinopyridine, particularly 6-hydrazinonicotinamide (HYNIC). The $^{99m}$Tc-labeling efficiency of the new chelant also depends on the coligand used for the radiolabeling. During the radiolabeling, [$^{99m}$Tc]pertechnetate is first reduced by a reducing agent, such as stannous chloride, to form a intermediate $^{99m}$Tc-coligand complex, which reacts with the chelant to form the expected macrocyclic $^{99m}$Tc complex. The yield of the macrocyclic $^{99m}$Tc complex is dependent on the stability or reactivity the intermediate $^{99m}$Tc-coligand complex. If the intermediate $^{99m}$Tc-coligand complex is not stable, it may undergo disproportionation to form the [$^{99m}$Tc] $O_2$ colloid and [$^{99m}$Tc]pertechnetate, which will significantly compromise the yield of the macrocyclic $^{99m}$Tc complex. If the intermediate $^{99m}$Tc-coligand complex is too stable, the reactivity of intermediate $^{99m}$Tc-coligand complex with the chelant will be low, which also compromises the yield of the macrocyclic $^{99m}$Tc complex. Among various coligands, tricine is the best with respect to yield and radiochemical purity, and the number of isomers of the macrocyclic $^{99m}$Tc complex.

The amount of said chelant used for preparation of macrocyclic metal complex could range from about 1 µg to about 1000 µg, or more preferably from about 5 µg to about 20 µg. The exact amount of the chelant depends upon the identity of the chelant, the procedure used for preparation of the macrocyclic metal complex, and the identity of the stabilizing coligand used for the radiolabeling.

Uncoordinated trialkyl- and triarylphosphines are prone to oxidation by an oxidant such as oxygen. Since the chelant is used in such a small amount (about 1 µg to about 1000 µg), it is preferred that the radiolabeling is performed under anaerobic conditions by exclusion of dissolved oxygen from the reaction mixture in order to minimize the oxidation of the triarylphosphine moiety of the chelant. Generally, exclusion of oxygen can be achieved by bubbling an inert gas (such as nitrogen and argon) through the reaction mixture or by evacuate the head space of the reaction vial before the addition of [$^{99m}$Tc]pertechnetate stock solution.

The amounts of the coligand used for preparation of macrocyclic metal complex can range from about 1 mg to about 1000 mg, or more preferably from about 1 mg to about 50 mg. The exact amount of the coligand is a function of the identity of for a specific macrocyclic metal complex, the procedure used for preparation of the macrocyclic metal complex, and the amount and identities of the other reactants used for the radiolabeling.

Hydrazones are used as protecting groups for the hydrazine moiety of the chelant. The hydrazone moiety preferably hydrolyzes to produce sufficient quantity of the free hydrazine moiety, which may or may not be protonated, prior to complexation with the metal radionuclide, M. The yield of the macrocyclic $^{99m}$Tc complex depends on the kinetics of hydrolysis of the hydrazone moiety of the chelant. The higher the degree of hydrolysis is, the higher the yield would be for the macrocyclic $^{99m}$Tc complex, within certain limits. However, the hydrolysis may not need to go to completion since there are typically about 5 to 100 equivalents of the hydrazone to the total Tc in each reaction mixture (Edwards, et al., Bioconjugate Chem. 1999, 10, 808).

Another aspect of the present invention is related to the use of the macrocyclic metal complexes as radiopharmaceuticals for the diagnosis of cardiovascular disorders, infectious disease and cancer. For "metal essential" $^{99m}$Tc complex radiopharmaceuticals, there is no targeting moiety and the biodistribution is exclusively determined by the physical properties of the macrocyclic $^{99m}$Tc complex. The use of three different ligating groups (aromatic hydrazine, triarylphosphine, and aminocarboxylate coligand) offers many opportunities to control the physical and biological characteristics of the macrocyclic $^{99m}$Tc complex. The extent of such control is dependent on the choice of three different ligating groups, and the degree of functionalization of the aromatic hydrazine moiety, the triarylphosphine moiety, and the linker between the aromatic hydrazine moiety.

Another aspect of the present invention is related to the use of new chelants as BFCs for the $^{99m}$Tc-labeling of biomolecules. For "metal essential" $^{99m}$Tc complex radiopharmaceuticals, such as $^{99m}$Tc-sestamibi, $[^{99m}Tc(MIBI)_6]^+$ (MIBI is 2-methoxy-2-methylpropyl-isonitrile) and $^{99m}$Tc-bicisate, $[^{99m}TcO(ECD)]$ (ECD is l,l-ethylene dicyteine diethyl ester), the ligand (MIBI or ECD) is preferably present in large excess. For receptor-based target specific radiopharmaceuticals, however, the use of large amount of BFC-BM may result in receptor site saturation, blocking the docking of the $^{99m}$Tc-labeled BFC-BM conjugate, as well as unwanted side effects. In order to avoid these problems, the concentration of the BFC-BM in the radiopharmaceutical kit is preferably very low (about $10^{-6}$-$10^{-4}$ M). Therefore, it may be necessary that the BFC attached to the biomolecule have high radiolabeling efficiency in order to achieve high specific activity, and to minimize the amount of unlabeled BFC-BM conjugate used to synthesize the radiopharmaceutical.

The new chelant disclosed in this invention contains an aromatic hydrazine moiety and a monodentate triarylphosphine moiety, and forms a macrocyclic metal complex with extremely high specific activity if the aromatic hydrazine is HYNIC, the monodentate ligating moiety is a functionalized triphenylphosphine, and the coligand is tricine. We found that the $^{99m}$Tc-labeling efficiency of the new chelant is better than or at least comparable to that reported for organic hydrazines (U.S. Pat. Nos. 5,206,370 and 5,753,520) and for various ternary ligand systems (Edwards, et al., Bioconjugate Chem. 1997, 8, 146; Liu, et al., Bioconjugate Chem. 1998, 9, 583; Edwards, et al., Bioconjugate Chem. 1999, 10, 884; Liu, S. and Edwards, D. S. Chem. Rev. 1999, 99, 2235).

Another aspect of the present invention is to provide a chelant-biomolecule conjugate. The chelant contains an aromatic hydrazine moiety and a monodentate triarylphosphine moiety. The aromatic hydrazine moiety and the monodentate triarylphosphine moiety are covalently connected via a linker. The aromatic hydrazine moieties include derivatives of hydrazinobenzene, hydrazinothiazole, hydrazinoimidazole, and more preferably hydrazinopyridine. The aryl groups in the monodentate triarylphosphine moiety include substituted phenyl, furyl, thienyl, or pyridyl. The linker between the hydrazine moiety and phosphine-P atom may be a simple alkylene chain or a small peptide sequence. The new BFC-BM conjugate may form macrocyclic metal complex-conjugates, when it is used in combination with a coligand.

The pharmacokinetic modifier (PKM), D', is often used to modify pharmacokinetics of a radiopharmaceutical. Various pharmacokinetic modifiers have been discussed in a recent review (Liu, S. and Edwards, D. S., Bioconjugate Chem. 2001, 12, 7-34). The choice of a linker depends upon the pharmacokinetic requirements for the radiopharmaceutical. The linker can be a simple hydrocarbon chain to increase lipophilicity, a peptide sequence (such as polyglycine, polyserine, or polyaspartic acid) to improve the hydrophilicity and renal clearance, or a poly(ethyleneglycol) linker to slow extraction by the hepatocytes. Sometimes, a metabolizable linker is used to increase the blood clearance and to reduce the background activity, thereby improving the target-to-background ratio.

The targeting biomolecule can be a protein, antibody, antibody fragment, peptide or polypeptide, or,peptidomimetic that is comprised of a recognition sequence or unit for a receptor or binding site expressed at the site of the disease, or for a receptor or binding site expressed on platelets or leukocytes. The exact chemical composition of targeting biomolecule is selected based on the disease state to be diagnosed, the mechanism of localization to be utilized, and to provide an optimal combination of rates of localization, clearance and radio-decay. The targeting biomolecules include platelet GPIIb/IIIa receptor antagonists, fibrin binding compounds (including peptides), leukocyte binding compounds (including peptides), chemotactic compounds (including peptides), LTB$_4$ receptor binders (including agonists and antagonists), somatostatin analogs, selectin binding compounds (including peptides), vitronectin receptor binders (including agonists and antagonists), kinase inhibitors (including tyrosine kinase inhibitors), matrix metalloproteinase inhibitors, oligonucleotides, fatty acids, nitroimidazoles, and carbohydrates.

The targeting biomolecule may also be in the form of proteins, antibodies, antibody fragments, peptides, polypeptides, or peptidomimetics that bind to receptors or binding sites on other tissues, organs, enzymes or fluids. Examples include the amyloid proteins that have been demonstrated to accumulate in patients with Alzheimer's disease, atrial naturetic factor derived peptides that bind to myocardial and renal receptors, antimyosin antibodies that bind to areas of infracted tissues, or nitroimidazoles derivatives that localize in hypoxic areas in vivo.

Another aspect of the present invention is to provide a macrocyclic metal complex radiopharmaceutical with high specific activity and high solution stability. The macrocyclic complex contains a chelant-conjugated biomolecule ("conjugate" in short) and a stabilizing coligand. The chelant contains an aromatic hydrazine moiety and a monodentate triarylphosphine moiety, and the aromatic hydrazine moiety and the monodentate triarylphosphine moiety are covalently connected via a linker. The aromatic hydrazine can be analogues of hydrazinobenzene, hydrazinothiazole, hydrazinoimidazole, or more preferably hydrazinopyridine, particularly HYNIC. The monodentate triarylphosphine moiety can be those containing substituted phenyl, furyl, thienyl, or pyridyl. The preferred triarylphosphine moiety is triphenylphosphine with the linker attached to the ortho or more preferably para-position relative to the C—P bond. The stabilizing coligand can be bidentate having two donor atoms such as oxygen and amine nitrogen or tetradentate with four donor atoms capable of occupying four sites in the coordination sphere of the metallic radionuclide.

Examples of bidentate coligands include but are not limited to: glycine, glucoheptonate, gluconate, 2-hydroxyisobutyrate, lactate, tartrate, mannitol, glucarate, maltol, Kojic acid, 2,2-bis(hydroxymethyl)propionic acid, 4,5-dihydroxy-1,3-benzene disulfonate, or substituted or unsubstituted 1,2 or 3,4 hydroxypyridinones. (The names for the ligands in these examples refer to either the protonated or non-protonated forms of the ligands.)

The functionalized aminocarboxylates have a combination of amine nitrogen and oxygen donor atoms. Examples include but are not limited to: N-[tris(hydroxymethyl)methyl]glycine (tricine), N-[bis(hydroxymethyl)methyl]glycine (dicine), N,N-bis(2-hydroxyethyl)glycine (bicine), nitrilotriacetic acid (NTA), N-(2-hydroxyethyl)iminodiacetic acid (HIDA), ethylenediamine-N,N'-diacetic acid (EDDA), N-(hydroxy)-ethylenediamine triacetic acid (HEDTA). The names for the ligands in these examples refer to either the protonated or non-protonated forms of the ligands.

Another aspect of the present invention is to provide methods for preparing a macrocyclic metal complex-conjugate radiopharmaceutical containing a chelant-conjugated biomolecule and a stabilizing coligand. For example, synthesis of the macrocyclic $^{99m}$Tc complex can be achieved by reacting [$^{99m}$Tc]pertechnetate with the conjugate in the presence of a reducing agent, such as stannous chloride, and an excess stabilizing coligand, preferably tricine. After the radiolabeling, the resulting reaction mixture may optionally be purified using one or more chromatographic methods, such as Sep-Pack or high performance liquid chromatography (HPLC). The preferred radiolabeling method are those, in which the macrocyclic metal complex radiopharmaceutical is prepared with high specific activity and high radiochemical purity without the post-labeling purification.

Another aspect of the present invention is to provide methods of using the target-specific macrocyclic metal complex-conjugate radiopharmaceutical containing a chelant-conjugated biomolecule ("conjugate" in short) as an imaging agent for the diagnosis of cardiovascular disorders such as thromboembolic disease or atherosclerosis, infectious disease and cancer.

For target-specific radiopharmaceuticals, the metal chelate (radionuclide chelated by a chelant and coligand) may have significant impact on the target uptake and biodistribution of the radiopharmaceutical. This is especially true for radiopharmaceuticals based on small molecules since in many cases the metal chelate contributes greatly to the overall size and molecular weight. Therefore, the choice of the aromatic hydrazine, the triarylphosphine, and the stabilizing coligand offers opportunities to modify the physical and biological properties of the macrocyclic metal complex.

However, the biological characteristics and the intended medical use of the macrocyclic metal complex radiopharmaceutical are dependent on the targeting biomolecule. For example, macrocyclic metal complex radiopharmaceuticals containing chelant-conjugated platelet GPIIb/IIIa receptor binders (including agonists and antagonists) or fibrin binding compounds (including peptides) are useful for detection of both arterial and venous thrombi. Macrocyclic metal complex radiopharmaceuticals containing chelant-conjugated platelet GPIIb/IIIa receptor binders (including agonists and antagonists) or fibrin binding compounds (including peptides) are also useful for detection of pulmonary embolism. Macrocyclic metal complex radiopharmaceuticals containing chelant-conjugated leukocyte binding compounds (including peptides), chemotactic compounds (including peptides), LTB$_4$ receptor binders (including agonists and antagonists), or selectin binding compounds (including peptides) are useful for the detection of the foci of infection or inflammation. Macrocyclic metal complex radiopharmaceuticals containing chelant-conjugated somatostatin analogs, vitronectin receptor binders (including agonists and antagonists), kinase inhibitors (including tyrosine kinase inhibitors), matrix metalloproteinase inhibitors, or antisense oligonucleotides are useful for early diagnosis of cancer.

For the purposes of this invention, the term "thromboembolic disease" is taken to include both venous and arterial disorders and pulmonary embolism, resulting from the formation of blood clots. For the diagnosis of thromboembolic disorders or atherosclerosis, the targeting biomolecule is selected from the group including, but not limited to, the cyclic IIb/IIIa receptor antagonists described in U.S. Pat. No. 6,022,523; the RGD containing peptides described in U.S. Pat. No. 4,578,079, U.S. Pat. No. 4,792,525, WO 89/05150, WO 89/10135, WO 91/01331, WO 91/15515 and by Ojima et al., 204$^{th}$ Meeting of the Am. Chem. Soc., 1992, Abstract 44; the peptides that are fibrinogen receptor antagonists described in EP-A-0,410,537, EP-A-0,410,539, EP-A-0,410,541, EP-A-0,422,937, EP-A-0,422,938, and EP-A-0,425,212, the specific binding peptides and polypeptides described as IIb/IIIa receptor ligands, ligands for the polymerization site of fibrin, laminin derivatives, ligands for fibrinogen, or thrombin ligands in WO 93/23085 (excluding the technetium binding groups); the oligopeptides that correspond to the IIIa protein described in WO 0/00178; the hirudin-based peptides described in WO 90/03391; the IIb/IIIa receptor ligands described in WO 90/15818; the thrombus, platelet binding or atherosclerotic plaque binding peptides described in WO 92/13572 (excluding the technetium binding group) or GB-A-2,268,494; the fibrin binding peptides described in U.S. Pat. Nos. 4,427,646 and 5,270,030; the hirudin-based peptides described in U.S. Pat. No. 5,279,812; or the fibrin binding proteins described in U.S. Pat. No. 5,217,705; the guanine derivatives that bind to the IIb/IIIa receptor described in U.S. Pat. No. 5,086,069; or the tyrosine derivatives described in EP-A-0,478,328, and by Hartman et al., J. Med. Chem., 1992, 35, 4640; or oxidized low density lipoprotein (LDL).

For the diagnosis of infection, inflammation or transplant rejection, the targeting biomolecule may be selected from the group including the leukocyte binding compounds (including peptides) described in WO 93/17719 (excluding the technetium binding group), WO 92/13572 (excluding the technetium binding group) or U.S. Pat. No. 5,792,444; the chemotactic compounds (including peptides) described in EP-A-0.398,143 or A. Fischman et al., Semin. Nuc. Med., 1994, 24, 154; or the leukostimulatory agents described in U.S. Pat. No. 5,277,892.

For the diagnosis of cancer, the targeting biomolecule may be selected from the group of somatostatin analogs described in U.S. Pat. Nos. 5,776,894 or U.S. Pat. No. 5,871,711, the selectin binding compounds (including peptides) described in WO 94/05269, the biological-function domains described in WO 93/12819, Platelet Factor 4 or the growth factors (PDGF, EGF, FGF, TNF, MCSF or Il-8).

Another aspect of the present invention is diagnostic kits for the preparation of radiopharmaceuticals useful as imaging agents for the diagnosis of cardiovascular disorders, infectious disease, inflammatory disease and cancer. Diagnostic kits of the present invention contain one or more vials containing the sterile, non-pyrogenic, formulation comprised of a predetermined amount of the chelant described in this invention, a stabilizing coligand, a reducing agent, and optionally other components such as buffers, lyophilization aids, stabilization aids, solubilization aids and bacteriostats.

The inclusion of one or more optional components in the formulation will frequently improve the ease of synthesis of the radiopharmaceutical by practicing end user, the ease of manufacturing the kit, the shelf-life of the kit, or the stability and shelf-life of the radiopharmaceutical. The improvement achieved by the inclusion of an optional component in the formulation must be weighed against the added complexity of the formulation and added cost to manufacture the kit. The one or more vials that contain all or part of the formulation can independently be in the form of a sterile solution or a lyophilized solid.

Buffers useful in the preparation of radiopharmaceuticals and in diagnostic kits useful for the preparation of said radiopharmaceuticals include but are not limited to phosphate, citrate, sulfosalicylate, and acetate. A more complete list can be found in the *United States Pharmacopeia*.

Lyophilization aids useful in the preparation of diagnostic kits useful for the preparation of radiopharmaceuticals include but are not limited to mannitol, lactose, sorbitol, dextran, Ficoll, and polyvinylpyrrolidine (PVP).

Stabilization aids useful in the preparation of radiopharmaceuticals and in diagnostic kits useful for the preparation of said radiopharmaceuticals include but are not limited to ascorbic acid, cysteine, monothioglycerol, sodium bisulfite, sodium metabisulfite, gentisic acid, and inositol.

Solubilization aids useful in the preparation of radiopharmaceuticals and in diagnostic kits useful for the preparation of said radiopharmaceuticals include but are not limited to ethanol, glycerin, polyethylene glycol, propylene glycol, polyoxyethylene sorbitan monooleate, sorbitan monoloeate, polysorbates, poly(oxyethylene)-poly(oxypropylene)poly(oxyethylene) block copolymers (Pluronics) and lecithin. Preferred solubilizing aids are polyethylene glycol, and Pluronics copolymers.

Bacteriostats useful in the preparation of radiopharmaceuticals and in diagnostic kits useful for the preparation of said radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or coligand and so forth.

The predetermined amounts of each component in the formulation are determined by a variety of considerations that are in some cases specific for that component and in other cases dependent on the amount of another component or the presence and amount of an optional component. In general, the minimal amount of each component is used that will give the desired effect of the formulation. The desired effect of the formulation is that the practicing end user can synthesize the radiopharmaceutical and have a high degree of certainty that the radiopharmaceutical can be injected safely into a patient and will provide diagnostic information about the disease state of that patient.

The diagnostic kits of the present invention can also contain written instructions for the practicing end user to follow to synthesize the radiopharmaceuticals. These instructions may be affixed to one or more of the vials or to the container in which the vial or vials are packaged for shipping or may be a separate insert, termed the package insert.

Another aspect of the present invention contemplates methods of imaging the site of thrombotic disease in a patient involving:
  providing a radiopharmaceutical using a reagent of the present invention capable of localizing at sites of thrombotic disease due to an interaction between the targeting biomolecule of the radiopharmaceutical and a receptor or binding site expressed at the site of the disease or with a receptor or binding site on an endogenous blood component that accumulates at the site;
  administering said radiopharmaceutical to a patient by injection or infusion; and
  imaging the patient using either planar or SPECT gamma scintigraphy.

Another aspect of the present invention contemplates methods of imaging the site of infection or infectious disease in a patient involving:
  providing a radiopharmaceutical using a reagent of the present invention capable of localizing at sites of infection or infectious disease due to an interaction between the targeting biomolecule of the radiopharmaceutical and a receptor or binding site expressed at the site of the disease or with a receptor or binding site on an endogenous blood component that accumulates at the site;
  administering said radiopharmaceutical to a patient by injection or infusion; and
  imaging the patient using either planar or SPECT gamma scintigraphy.

Another aspect of the present invention contemplates methods of imaging the site of inflammation in a patient involving:
  providing a radiopharmaceutical using a reagent of the present invention capable of localizing at sites of inflammation due to an interaction between the targeting biomolecule of the radiopharmaceutical and a receptor or binding site expressed at the site of inflammation or with a receptor or binding site on an endogenous blood component that accumulates at the site;
  administering said radiopharmaceutical to a patient by injection or infusion; and
  imaging the patient using either planar or SPECT gamma scintigraphy.

Another aspect of the present invention contemplates methods of imaging the site of cancer in a patient involving:
  providing a radiopharmaceutical using a reagent of the present invention capable of localizing at sites of cancer due to an interaction between the targeting biomolecule of the radiopharmaceutical and a receptor or binding site expressed at the site of the cancer or with a receptor or binding site on an endogenous blood component that accumulates at the site;
  administering said radiopharmaceutical to a patient by injection or infusion; and
  imaging the patient using either planar or SPECT gamma scintigraphy.

Other features of the invention will become apparent in the course of the following descriptions of exemplary embodiments which are given for illustration of the invention and are not intended to be limiting thereof. The present invention will now be illustrated by reference to the following specific, non-limiting examples. Those skilled in the art of organic synthesis may be aware of still other synthetic routes to the invention compounds. The reagents and intermediates used herein are either commercially available or prepared according to standard literature procedures, unless otherwise described.

EXAMPLES

Chemicals, such as N-$\epsilon$-(t-butoxycarbonyl)lysine methyl ester hydrochloride, N-$\alpha$-(t-butoxycarbonyl)-N$^{imidazole}$-(t-butoxycarbonyl)histidine were purchased from Calbiochem Inc. and were used as received. Diethylenetriamine, ethylenediamine, ethylenediamine-N,N'-diacetic acid (EDDA), 1,6-diaminohexane, 1-hydroxybenzotriazole, 1-hydroxyazabenzotriazole, N-(2-hydroxyethyl)iminediacetic acid (HEIDA), 1-hydroxybenzotriazole, 4 M HCl in dioxane, isonicotinic acid, nicotinic acid, nitrilotriacetic acid (NTA), picolinic acid, 3-pyridineacetic acid, 1-O-(N,N',N'',N'''-tetramethyluronium)benzotriazoloxy hexafluorophosphate, 1-O-(N,N',N'',N'''-tetramethyluronium)azabenzotriazoloxy hexafluorophosphate, 1-O-(N,N',N'',N'''-tetramethyluronium)benzotriazoloxy hexafluorophosphate, spermidine, tricine, and tris were purchased from Aldrich or Sigma Chemical Co., and were used as received. $Na^{99m}TcO_4$ was obtained from a Technelite® $^{99}Mo/^{99m}Tc$ generator, Bristol-Myers Squibb Medical Imaging Inc., North Billerica, Mass. Sodium succinimidyl 6-(2-(2-sulfonatobenzaldehyde)hydrazono)nicotinate was prepared according to published procedure (Harris, et al. *Bioconjugate Chem.* 1999, 10, 808).

Instruments and Methods

NMR spectral data ($^1$H) were recorded on a 600 MHz Bruker DRX FT NMR spectrometer. The $^1$H NMR data were reported as δ (ppm) relative to TMS. Electrospray MS analyses were performed using an IonSpec Ultima FT Mass Spectrometer in the positive ion mode. LC-MS spectra were collected using a HP1100 LC/MSD system with API-electrospray interface in the positive ion mode (Zorbax SB—$C_{18}$ column, 4.6 mm×250 mm, 80 Å pore size). The flow rate was 1 ml/minute with a gradient mobile phase starting 98% solvent A (0.1% formic acid in water) and 2% solvent B (0.1% formic acid in 90% acetonitrile) to 100% solvent B at 14 minutes.

Preparative HPLC methods used a Varian Prep Star system equipped with a UV/visible detector (λ=220 nm) and a Jupiter $C_{18}$ prep column (15 μm, 300 Å, 21.2×250 mm). The flow rate was 20 mL/minute with the following gradients:

| Time | 0 min | |
|---|---|---|
| Gradient A | | |
| | | 40 min |
| Solvent A (0.1% TFA in water): | 80% | 10% |
| Solvent B (0.1% TFA in 90% acetonitrile) | 20% | 90% |
| Gradient B | | |
| | | 30 min |
| Solvent A (0.1% TFA in water): | 100% | 60% |
| Solvent B (0.1% TFA in 90% acetonitrile) | 0% | 40% |
| Gradient C | | |
| | | 40 min |
| Solvent A (0.1% TFA in water): | 100% | 20% |
| Solvent B (0.1% TFA in 90% acetonitrile) | 0% | 80% |
| Gradient D | | |
| | | 40 min |
| Solvent A (0.1% TFA in water): | 100% | 50% |
| Solvent B (0.1% TFA in 90% acetonitrile) | 0% | 50% |
| Gradient E | | |
| | | 30 min |
| Solvent A (0.1% TFA in water): | 100% | 20% |
| Solvent B (0.1% TFA in 90% acetonitrile) | 0% | 80% |
| Gradient F | | |
| | | 40 min |
| Solvent A (0.1% TFA in water): | 100% | 10% |
| Solvent B (0.1% TFA in 90% acetonitrile) | 0% | 90% |

The radio-HPLC methods used a HP-1000 HPLC system with a UV/visible detector (λ=230 nm), an IN-US radio-detector, and a Zorbax $C_{18}$ column (4.6 mm×250 mm, 80 Å pore size). The flow rate was 1 mL/min with a gradient mobile phase Solvent A was 25 mM ammonium acetate buffer, pH 6.8, and solvent B was acetonitrile.

| Time | 0 min | 20 min |
|---|---|---|
| Gradient I | | |
| Solvent A: | 90% | 80% |
| Solvent B: | 10% | 20% |
| Gradient J | | |
| Solvent A: | 80% | 60% |
| Solvent B: | 20% | 40% |
| Gradient K | | |
| Solvent A: | 100% | 80% |
| Solvent B: | 0% | 20% |
| Gradient L | | |
| Solvent A: | 100% | 70% |
| Solvent B: | 0% | 30% |

The ITLC method used GelmanSciences silica-gel paper strips and a 1:1 mixture of acetone and saline as eluant. By this method, the macrocyclic $^{99m}$Tc complexes migrate to the solvent front while the [$^{99m}$Tc]pertechnetate and [$^{99m}$Tc] colloid remain at the origin. The corrected radiolabeling yield was calculated by subtraction of the percentage of [$^{99m}$Tc]pertechnetate and [$^{99m}$Tc]colloid as determined by ITLC from the yield determined by radio-HPLC.

Synthesis of N-ε-(t-butoxycarbonyl)-N-α-(6-(2-(2-Sulfonatobenzaldehyde)hydrazono)nicotinyl)lysine Methyl Ester

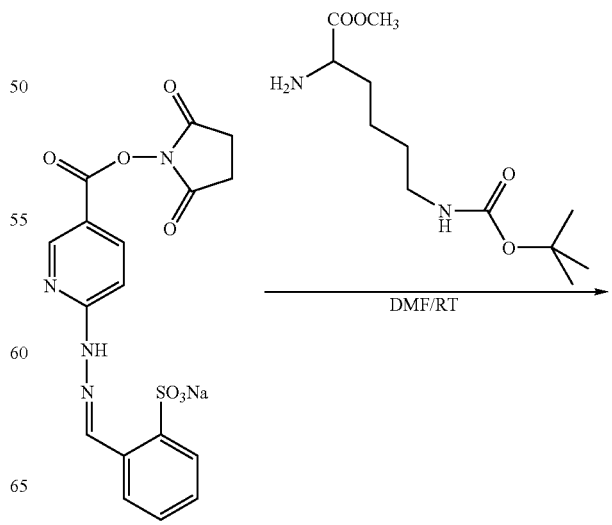

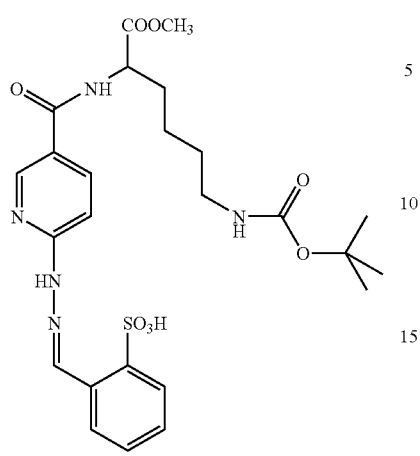

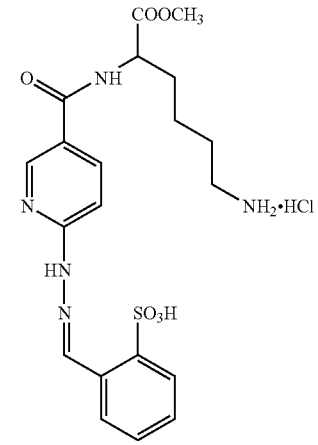

To a 25 mL round bottom flask were added sodium succinimidyl 6-(2-(2-sulfonatobenzaldehyde)hydrazono)-nicotinate (250 mg, 0.57 mmol) and 3 mL of DMF. To the solution was added N-ε-(t-butoxycarbonyl)lysine methyl ester hydrochloride (184 mg, 0.62 mmol), followed by the addition of diisopropylethylamine (0.32 mg, 0.43 mL). The resulting solution was stirred under a nitrogen atmosphere for 15 h. DMF was removed in vacuo and the crude oil subjected to HPLC purification using the preparative HPLC (Gradient A). The collected fractions were combined, and were lyophilized to give a fluffy white powder. The yield was 239 mg (~75%). MS (ESI, +ve): M/Z=564.2244 for $C_{25}H_{33}N_5O_8S$ ([M+H]$^+$). $^1$H NMR (600 MHz, DMSO-d$_6$+DCl): 9.376 (s, 1H), 8.617 (s, 1H), 8.466 (dd, 1H, J=2.4 Hz), 7.8 (m, 1H), 7.4 (m, 2H), 7.25 (bd, 1H), 4.38 (t, 1H, J=7.2 Hz), 3.64 (s, 3H), 2.89 (m, 2H), 1.8 (q, 2H, J=7.2 Hz), 1.34-1.38 (13H). $^{13}$C (DMSO-d$_6$+DCl): 172.4, 162.5, 155.5, 149.8, 147.5, 129.5, 120.2, 77.43, 52.84, 51.97, 31.25, 30.07, 29.6, 29, 28.2, 26.5, 23.

Synthesis of N-α-(6-(2-(2-Sulfonatobenzaldehyde)hydrazono)nicotinyl)lysine Methyl Ester Hydrochloride Salt To a 25 mL round bottom flask was added N-ε-(t-butoxycarbonyl)-N-α-(6-(2-(2-sulfonatobenzaldehyde)-hydrazono)nicotinoyl)lysine methyl ester (200 mg, 0.36 mmol). The flask cooled to 0° C. Upon dropwise addition of 2.0 mL of 4M HCl in dioxane, the fluffy white starting material immediately turned to a pale yellow solid. The reaction mixture was allowed to stand at 0° C. for 5 minutes and then at room temperature for 25 minutes with occasional shaking. The pale yellow solid was separated by filtration and dried under vacuum overnight. The LC-MS showed that the product was has >95% purity. The yield was 164 mg (~100%). The crude product was used for next step of reactions without further purification. MS (ESI, +ve): M/Z=464.1526 for $C_{25}H_{33}N_5O_8S$ ([M+H]$^+$). $^1$H NMR (DMSO-d$_6$+D$_2$O): 9.23 (s, 1H) 8.55 (d, 1H, J=1.8 Hz), 8.33 (d, 1H), 8.23 (d, 1H), 7.8 (d of d, 1H, J=7.2, 1.8 Hz), 7.4 (m, 2H), 7.2 (d, 2H, J=9.6 Hz), 4.4 (m, 1H), 3.65 (s, 3H), 2.7 (t, 2 H, J=7.2 Hz), 1.8 (m, 2H), 1.5 (m, 2H), 1.38-1.42 (m, 2H).

Example I

Synthesis of N-ε-(Isonicotinyl)-N-α-(6-(2-(2-Sulfonatobenzaldehyde)hydrazono)nicotinyl)lysine Methyl Ester (HYNIC-Lys(OMe)-ISONIC)

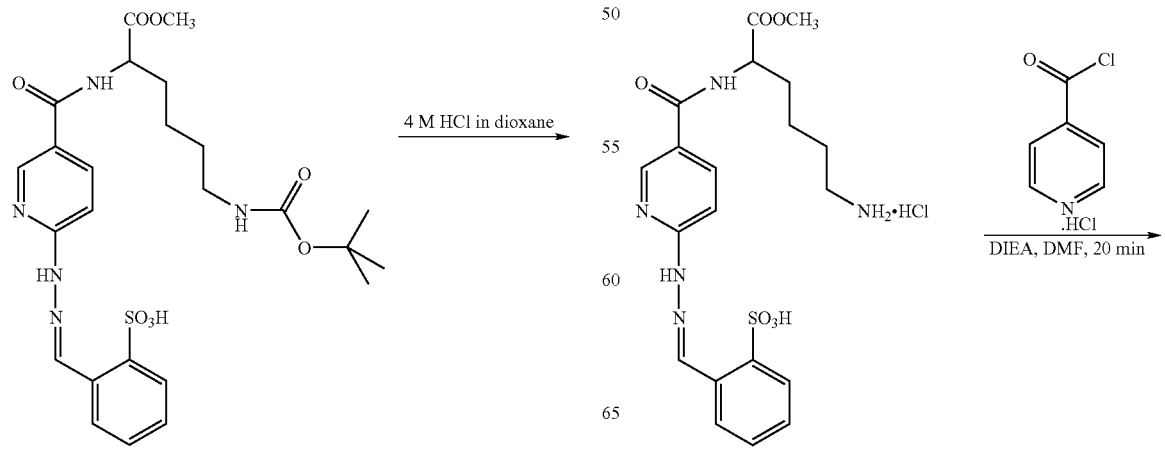

-continued

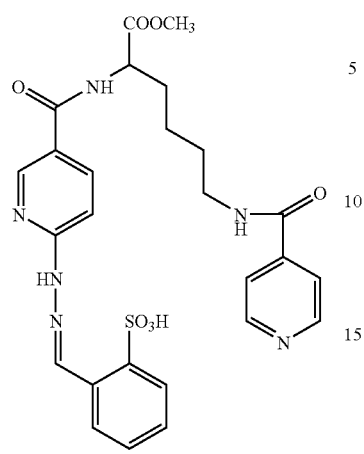

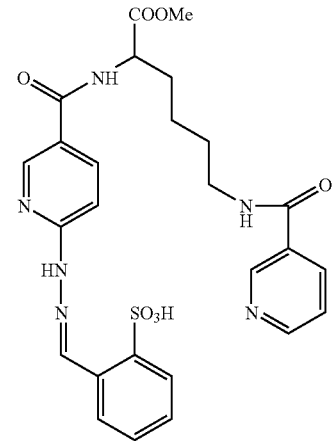

To a 25 mL round bottom flask was added isonicotinoyl chloride hydrochloride (16.0 mg, 0.90 mmol) and 3 mL of DMF. To the solution above was added N-α-(6-(2-(2-sulfonatobenzaldehyde)hydrazono)nicotinyl)lysine methyl ester hydrochloride (50 mg, 0.10 mmol), followed by addition of DIEA (0.0695 mL, 51.62 mg) and 1 mL of DMF. The reaction mixture was stirred for 20 minutes. DMF was removed in vacuo and the crude oil subjected to HPLC purification using preparative HPLC (Gradient B). The collected fractions were combined, and were lyophilized to give a fluffy white powder. The yield was 35.5 mg (~70%). MS (ESI, +ve): M/Z=569.1815 for $C_{26}H_{28}N_6O_7S$ ([M+H]$^+$). $^1$H NMR (DMSO-d$_6$+D$_2$O): 9.38 (s, 1H), 9.06 (d, 2H, J=6.6 Hz), 8.632 (s, 1H), 8.49-8.36 (m, 4H), 7.81 (dd, 1H, J=8.4, 7 Hz), 7.4 (m, 2H), 7.22 (br, 1H), 4.4 (m, 1H), 3.65 (s, 3H), 3.3 (m, 2H), 1.86 (m, 2H), 1.59-1.43 (m, 4H).

Example II

Synthesis of N-ε-(Nicotinyl)-N-α-(6-(2-(2-Sulfonatobenzaldehyde)hydrazono)nicotinyl)lysine Methyl Ester (HYNIC-Lys(OMe)-NIC)

To a 25 mL round bottom flask was added nicotinic acid hydrochloride (14.32 mg, 0.01 mmol), followed by 5 mL DMF and 1-O-(N,N',N'',N'''-tetramethyluronium)azabenzotriazoloxy hexafluorophosphate (41 mg, 0.01 mmol), 1-hydroxyazabenzotriazole (14.6 mg, 0.01 mmol) and DIEA (0.104 mL, 0.774 gm). After stirring for 5 minutes, N-α-(6-(2-(2-sulfonatobenzaldehyde)hydrazono)nicotinyl)lysine methyl ester hydrochloride (50 mg, 0.0998 mmol) was added and the resulting solution was stirred for 30 minutes. The DMF was removed in vacuo and the crude oil subjected to HPLC purification using the preparative HPLC (Gradient C). The collected fractions were combined, and were lyophilized to give a fluffy white solid. The yield was 42 mg (82%). MS (ESI, +ve): M/Z=569.1815 for $C_{26}H_{28}N_6O_7S$ ([M+H]$^+$). $^1$H NMR (DMSO-d$_6$+DCl): 9.3 (d, 2H, J=16.2 Hz), 9.0 (d, 1H, J=4.8 Hz), 8.9 (d, 1H, J=8.4 Hz), 8.6 (s, 1H), 8.49 (d of d, 1H, J=2.4, 7.2 Hz), 8.43 (d, 1H), 8.1 (m, 1H), 7.8 (dd, 1H, J=2.4, 1.2 Hz), 7.4(m, 2H). 7.28(d, 1H), 4.4 (m, 1H), 3.65 (s, 3H), 3.29 (m, 2H), 1.8 (m, 2H), 1.59-1.44 (m, 4H).

Example III

Synthesis of N-ε-(Picolinyl)-N-α-(6-(2-(2-Sulfonatobenzaldehyde)hydrazono)nicotinyl)lysine Methyl Ester (HYNIC-Lys(OMe)-Pic)

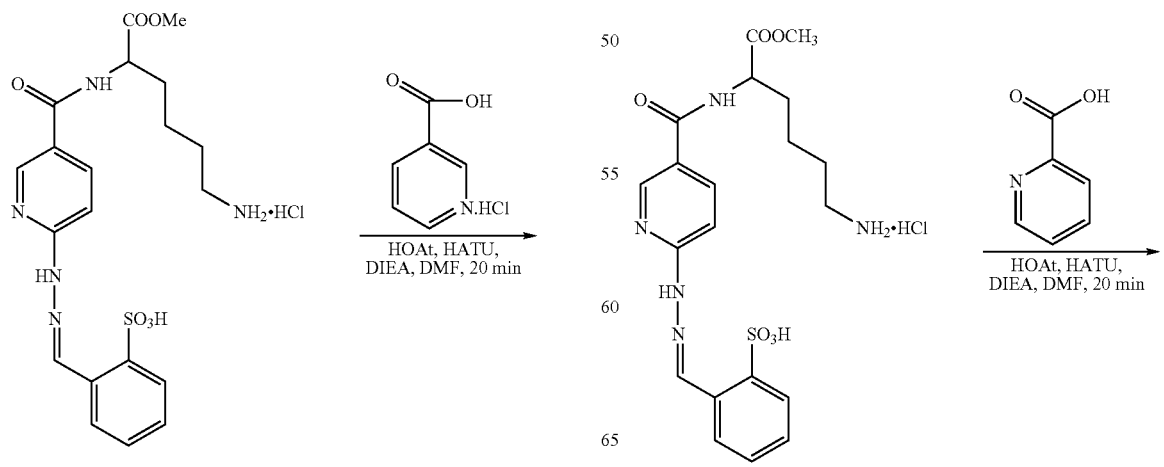

-continued

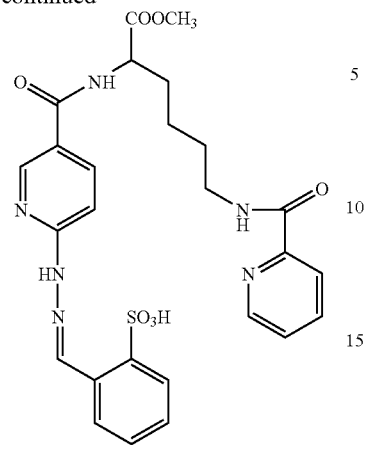

To a round bottom flask were added picolinic acid (10 mg, 0.08 mmol), 5 mL of DMF, 1-O-(N,N',N'',N'''-tetramethyluronium)azabenotriazoloxy hexafluorophosphate (38 mg, 0.01 mmol), 1-hydroxyazabenzotriazole (14.6 mg, 0.01 mmol) and DIEA (0.104 mL, 0.077 gm). After the solution was stirred for 7 minutes, N-α-(6-(2-(2-sulfonatobenzaldehyde)hydrazono)nicotinyl)lysine methyl ester hydrochloride (50 mg, 0.01 mmol) was added. The reaction mixture was stirred for another 30 minutes. DMF was removed in vacuo and the crude oil subjected to HPLC purification using the preparative HPLC (Gradient D). The collected fractions were combined, and were lyophilized to give a fluffy white solid. The yield was 34 mg (73%). MS (ESI, +ve): M/Z=569.1815 for $C_{26}H_{28}N_6O_7S$ ([M+H]$^+$). $^1$H NMR (DMSO-d$_6$+DCl): 9.32 (br s, 1H), 8.62 (m, 1H), 8.52 (s, 1H), 8.3 & 8.24 (bs, 2H), 8.0-7.9 (m, 2H), 7.8 (dd, 1H, J=1.2 Hz, J=6 Hz), 7.5 (m, 1H), 7.4 (m, 2H), 7.19 (d, 1H, 9.6 Hz), 4.4 (m, 1H), 3.64 (s, 3H), 3.3 (m, 2H), 1.9-1.8 (m, 2H), 1.6-1.54 (m, 2H), 1.45-1.25 (m, 2H).

Example IV

Synthesis of N-ε-(3-Pyridineacetyl)-N-α-(6-(2-(2-Sulfonatobenzaldehyde)hydrazono)-nicotinyl)lysine Methyl Ester (HYNIC-Lys(OMe)-PA)

To a 15 mL round bottom flask were added 3-pyridylacetic acid hydrochloride (17.9 mg, 0.10 mmol), 5 mL of DMF, 1-O-(N,N',N'',N'''-tetramethyluronium)azabenzotriazoloxy hexafluorophosphate (47.22 mg, 0.12 mmol) and DIEA (0.104 mL, 0.0774 g). After stirring at room temperature for 7 minutes, N-α-(6-(2-(2-sulfonatobenzaldehyde)-hydrazono)nicotinyl)lysine methyl ester hydrochloride (57 mg, 0.11 mmol) was added. The resulting solution stirred for an additional 2 hours. DMF was removed in vacuo and the crude oil subjected to HPLC purification using the preparative HPLC (Gradient C). The collected fractions were combined, and were lyophilized to give a white solid. The yield was 17.5 mg (~30%). MS (ESI, +ve): M/Z=583.1973 for $C_{27}H_{30}N_6O_7S$ ([M+H]$^+$). $^1$H NMR (DMSO-d$_6$): 9.22 (s, 1H), 8.8-8.5 (m, 5H), 8.24-8.15 (m, 3H), 7.99 (t, 1H), 7.79 (dd, 2H, J=1.2 Hz, J=13.8 Hz), 7.42-7.37 (m, 3H), 7.22 (m, 2H), 4.4 (m, 1H), 3.6 (s, 3H), 3.07 (m, 2H), 1.79 (m, 2H), 1.45-1.33 (m, 4H).

Example V

Synthesis of 1-(N-(6-(2-(2-Sulfonatobenzaldehyde)hydrazono)nicotinyl))-6-(nicotinoyl) hexanediamine (HYNIC-HD-NIC)

1-(N-(6-(2-(2-Sulfonatobenzaldehyde)hydrazono)-Nicotinyl))hexanediamine

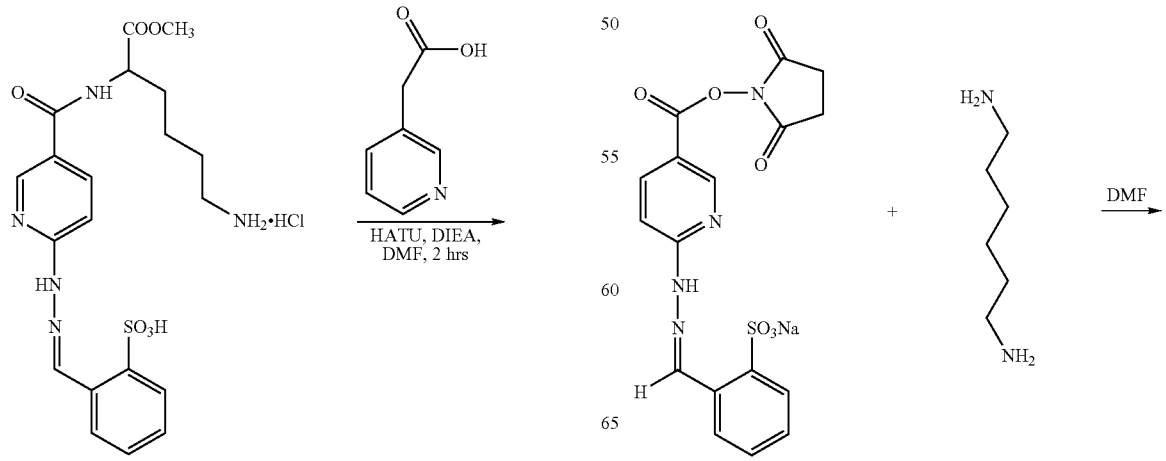

-continued

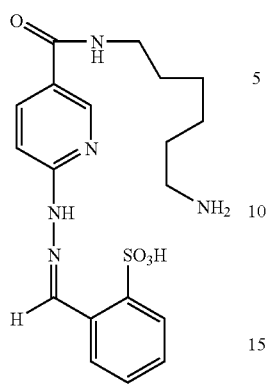

To a 15 ml round bottom flask was added sodium succinimidyl 6-(2-(2-sulfonatobenzaldehyde)hydrazono)nicotinate (100 mg, 0.226 mmol) followed by DMF (3 mL) followed by hexamethylenediamine (26.3 mg, 0.226 mmol). The mixture was stirred for 10 minutes. The DMF was removed in vacuo and the crude mixture subjected to purification by HPLC (Gradient E). The collected fractions were combined, and were lyophilized to give a white solid. The yield was 46 mg (~49%). MS (ESI, +ve): M/Z=420.1689 for $C_{19}H_{25}N_5O_4S$ ([M+H]$^+$). $^1$H NMR (DMSO-d$_6$+DCl): 9.34 (s, 1H), 8.59 (s, 1H), 8.50 (dd, 2H, J=2.0, 7.2 Hz), 8.09 (t, 1 H), 7.8 (m, 1H), 7.4 (m, 2H), 7.23 (br, 1H), 3.25 (t, 2H), 2.73 (m, 2H), 1.5 (m, 4H), 1.31 (m, 4H).

1-(N-(6-(2-(2-Sulfonatobenzaldehyde)hydrazono)-Nicotinyl))-6-(Nicotinoyl)hexanediamine To a 15 mL round bottom flask was added nicotinic acid (5.34 mmol, 0.043 mmol) followed by 1-O-(N,N',N'',N'''-tetramethyluronium)azabenzotriazoloxy hexafluorophosphate(18.14 mg, 0.047 mmol). To the above mixture was then added DMF (3 mL) and diisopropylethylamine (16.78 mg, 0.129 mmol, 0.022 mL). The solution was stirred for 5 minutes after which 1-(N-(6-(2-(2-sulfonatobenzaldehyde)hydrazono)nicotinyl))hexanediamine (20 mg, 0.047 mmol) was added in one lot. The reaction mixture was stirred for 30 minutes. The DMF was then removed in vacuo and the crude oil subjected to HPLC purification (Gradient F). The collected fractions were combined, and were lyophilized to give a white solid. The yield was 18 mg (80%). MS (ESI, +ve): M/Z=525.1915 for $C_{25}H_{28}N_6O_5S$ ([M+H]$^+$). $^1$H NMR (600 MHz, DMSO-d$_6$+DCl): 9.3 (d, 2H, J=7.2 Hz), 9.04 (d, 1H, J=5.4 Hz), 9.02 (d, 1H, J=8.4 Hz), 8.58 (s, 1H), 8.48 (dd, 2H, J=1.8, 7.8 Hz), 8.17 (m, 1H), 7.79 (m, 1H), 7.4 (m, 2H), 7.23 (br, 1H), 3.3 (t, 2H, J=7.2 Hz), 3.2 (t, 2H, J=7.2 Hz), 1.54 9m, 4H), 1.35 (m, 4H).

Example VI

Synthesis of 2-{[5-(3-{4-[(Pyridine-3-Carbonyl)amino]-Butylamino}propylcarbamoyl)-Pyridin-2-yl]-hydrazonomethyl}-Benzenesulfonic Acid (HYNIC-SP-NIC)

N-(6-(2-(2-Sulfonatobenzaldehyde)hydrazono)nicotinyl)-spermidine

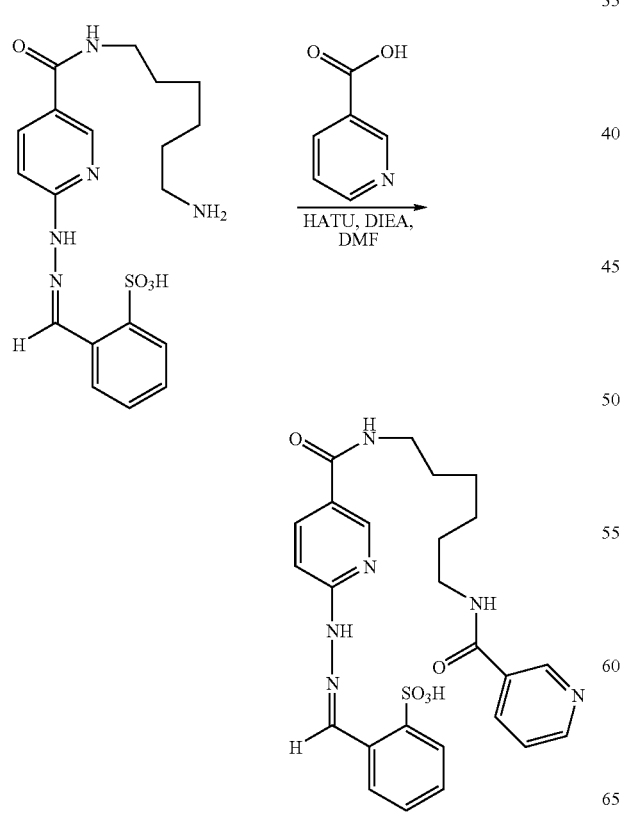

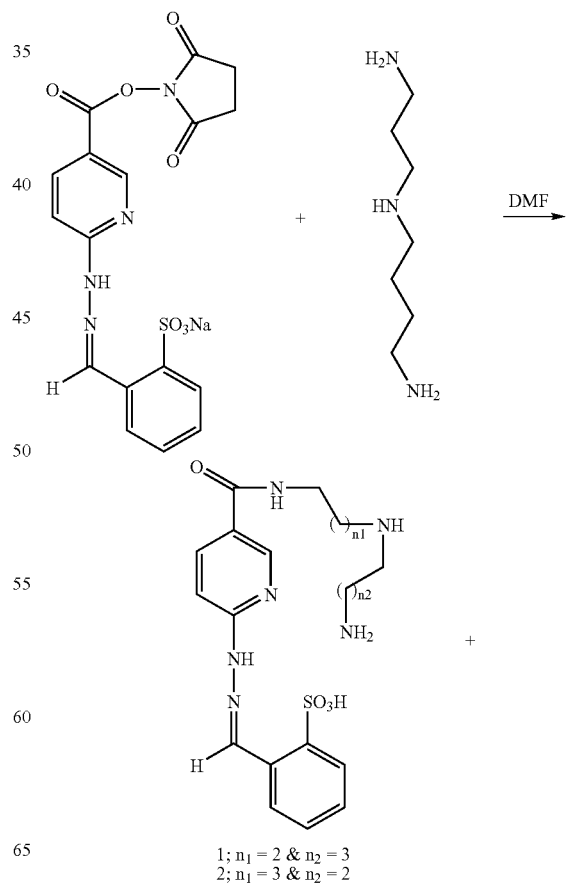

1; n$_1$ = 2 & n$_2$ = 3
2; n$_1$ = 3 & n$_2$ = 2

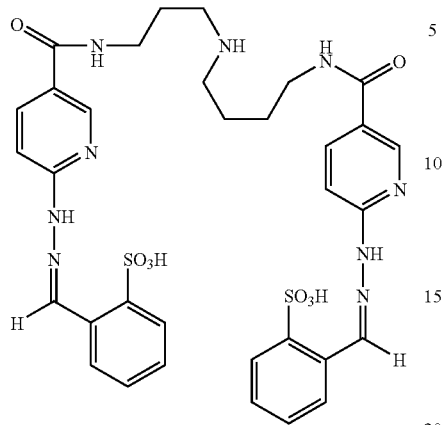

To a round bottom flask was added sodium succinimidyl 6-(2-(2-sulfonatobenzaldehyde)hydrazono)-nicotinate (50 mg, 0.113 mmol) followed by 3 mL of DMF. To this mixture was then added spermidine (16.46 mg, 17.79 µL). The reaction mixture was stirred for 1 hour under a nitrogen atmosphere. DMF was removed and the crude mixture was purified by HPLC (Gradient D). A combined 19.4 mg of compounds 1 and 2 was isolated in 38.5% yield along with 14.6 mg of compound 3 (by-product). Both 1 and 2 were collected as pure fractions; but it was not determined as to which fraction was compound 1 or 2. MS (ESI, +ve): M/Z=449.1959 for $C_{20}H_{28}N_6O_4S$ ([M+H]$^+$). $^1$H NMR of fraction 4 (600 MHz, DMSO-d$_6$+DCl): 9.1 (s, 1H), 8.6 (s, 1H), 8.3 (br, 2H), 8.1 (d, 2H), 7.8 (m, 3H), 7.25 (m, 3H), 3.4 (m, 3H), 3.0 (br, 4H), 2.89 (br, 2H), 1.8 (m, 2H), 1.6 (br, 4H).

2-{[5-(3-{4-[(Pyridine-3-Carbonyl)amino]-Butylamino}propylcarbamoyl)-Pyridin-2-yl]-hydrazonomethyl}-Benzenesulfonic Acid

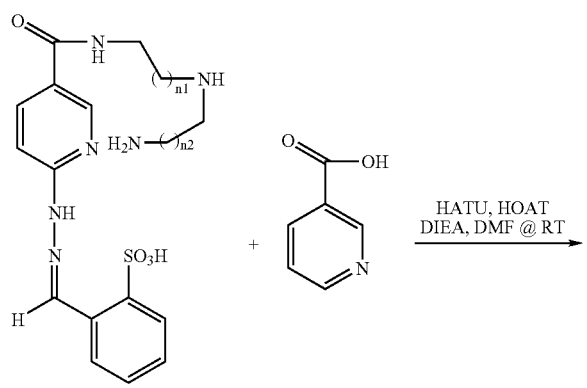

1; $n_1 = 2$ & $n_2 = 3$
2; $n_1 = 3$ & $n_2 = 2$
only one isomer used

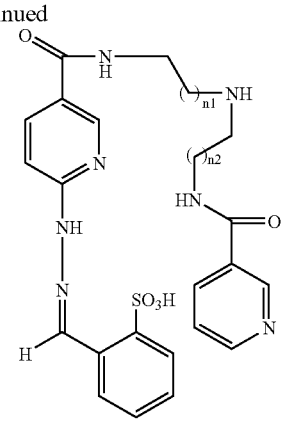

To a round bottom flask was added nicotinic acid (3.46 mg, 0.028 mmol) followed by 1-O-(N,N',N",N'"-tetramethyluronium)azabenzotriazoloxy hexafluorophosphate (10.9 mg, 0.031 mmol). The mixture was dissolved in 3 mL of DMF, followed by addition of N-(6-(2-(2-sulfonato-benzaldehyde)hydrazono)nicotinyl)spermidine (14 mg, 0.0312 mmol; fraction 4 from above) in one lot. The reaction mixture was stirred for 30 minutes. DMF was then removed in vacuo and the crude oil subjected to HPLC purification (Gradient D). The collected fractions were combined, and were lyophilized to give a white solid. The yield was 10.2 mg (59%). MS (ESI, +ve): =554.2168 for $C_{26}H_{31}N_7O_5S$ ([M+H]$^+$). $^1$H NMR (DMSO-d$_6$+DCl): 9.25 (s, 1H), 9.23 (s, 1H), 9.0 (dd, 2H), 8.6 (s, 1H), 8.5 (d, 1H), 8.4 (br s, 1H), 8.18 (d of d, 1H), 7.75 (d, 1H), 7.43 (m, 2H), 7.23 (br, 1H), 3.28 (m, 4H), 2.9 (m, 4H), 1.88 (m, 2H), 1.6 (m, 4H).

Example VII

[$^{99m}$Tc(HYNIC-Lys(OMe)-His)(tricine)]

To a sealed 5.0 mL vial were added HYNIC-Lys(OMe)-His (100 µg), 1.0 mL of in 0.25 M succinate buffer (pH=5.0), and 0.3 mL of tricine solution (100 mg/mL in 0.25 M succinate buffer, pH=5.0). After addition of 0.3 mL of $^{99m}$TcO$_4^-$ solution (~30 mCi) and 25 µL of SnCl$_2$.2H$_2$O solution (1.0 mg/mL in 0.1 N HCl), the mixture was heated in a water-bath at 100° C. for 15 minutes. After cooling to room temperature, a sample of the resulting solution was analyzed by radio-HPLC (Gradient I) and ITLC. The radiolabeling yield was >95%.

Example VIII

[$^{99m}$Tc(HYNIC-Lys(OMe)-NIC)(tricine)]

To a sealed 5.0 mL vial were added 0.5 mL of HYNIC-Lys(OMe)-NIC solution (10 µg/mL) in 0.25 M succinate buffer (pH=5.0), and 0.2 mL of tricine solution (100 mg/mL in 0.25 M succinate buffer, pH=5.0). After addition of 0.4 mL of $^{99m}$TcO$_4^-$ solution (~30 mCi) and 25 µL of SnCl$_2$.2H$_2$O solution (1.0 mg/mL in 0.1 N HCl), the mixture was heated in a water-bath at 100° C. for 10 minutes. After cooling to room temperature, a sample of the resulting solution was analyzed by radio-HPLC (Gradient I) and ITLC. The radiolabeling yield was >95%.

Example IX

[$^{99m}$Tc(HYNIC-Lys(OMe)-NIC)(Pic)$_2$]

To a sealed 5.0 mL vial were added 0.8 mL of HYNIC-Lys(OMe)-NIC solution (12 μg/mL) in 0.25 M succinate buffer (pH=5.0) and 0.2 mL of picolinic acid solution (5 mg/mL in 0.25 M succinate buffer, pH=5.0). After addition of 0.2 mL of $^{99m}$TcO$_4^-$ solution (~20 mCi) and 25 μL of SnCl$_2$.2H$_2$O solution (1.0 mg/mL in 0.1 N HCl), the mixture was heated in a water-bath at 100° C. for 10 minutes. After cooling to room temperature, a sample of the resulting solution was analyzed by radio-HPLC (Gradient J) and ITLC. The radiolabeling yield was 50.2%.

Example X

[$^{99m}$Tc(HYNIC-Lys(OMe)-NIC)(NTA)]

To a sealed 5.0 mL vial were added 0.6 mL of HYNIC-Lys(OMe)-NIC solution (10 μg/mL) in 0.25 M succinate buffer (pH=5.0), and 0.5 mL of NTA solution (20 mg/mL in 0.25 M succinate buffer, pH=5.0). After addition of 0.3 mL of $^{99m}$TcO$_4^-$ solution (~30 mCi) and 25 μL of SnCl$_2$.2H$_2$O solution (1.0 mg/mL in 0.1 N HCl), the mixture was heated in a water-bath at 100° C. for 10 minutes. After cooling to room temperature, a sample of the resulting solution was analyzed by radio-HPLC (Gradient I) and ITLC. The radiolabeling yield was ~65%.

Example XI

[$^{99m}$Tc(HYNIC-Lys(OMe)-NIC)(Et-EDTA)]

To a sealed 5.0 mL vial were added 0.6 mL of HYNIC-Lys(OMe)-NIC solution (10 μg/mL) in 0.25 M succinate buffer (pH=5.0), and 0.5 mL of ET-EDTA solution (20 mg/mL in 0.25 M succinate buffer, pH=5.0). After addition of 0.3 mL of $^{99m}$TcO$_4^-$ solution (~30 mCi) and 25 μL of SnCl$_2$.2H$_2$O solution (1.0 mg/mL in 0.1 N HCl), the mixture was heated in a water-bath at 100° C. for 10 minutes. After cooling to room temperature, a sample of the resulting solution was analyzed by radio-HPLC (Gradient I) and ITLC. The radiolabeling yield was 27.5%.

Example XII

[$^{99m}$Tc(HYNIC-Lys(OMe)-NIC)(Tris)]

To a sealed 5.0 mL vial were added 0.7 mL of HYNIC-Lys(OMe)-NIC solution (14 μg/mL) in 0.25 M succinate buffer (pH=5.0), and 0.5 mL of Tris solution (20 mg/mL in 0.25 M succinate buffer, pH=5.0). After addition of 0.2 mL of $^{99m}$TcO$_4^-$ solution (~20 mCi) and 25 μL of SnCl$_2$.2H$_2$O solution (1.0 mg/mL in 0.1 N HCl), the mixture was heated in a water-bath at 100° C. for 10 minutes. After cooling to room temperature, a sample of the resulting solution was analyzed by radio-HPLC (Gradient L) and ITLC. The radiolabeling yield was >95%.

Example XIII

[$^{99m}$Tc(HYNIC-Lys(OMe)-NIC)(Glucoheptonate)$_2$]

To a sealed 5.0 mL vial were added 0.7 mL of HYNIC-Lys(OMe)-NIC solution (14 μg/mL) in 0.25 M succinate buffer (pH=5.0), and 0.5 mL of sodium glucoheptonate solution (20 mg/mL in 0.25 M succinate buffer, pH=5.0). After addition of 0.2 mL of $^{99m}$TcO$_4^-$ solution (~20 mCi) and 25 μL of SnCl$_2$.2H$_2$O solution (1.0 mg/mL in 0.1 N HCl), the mixture was heated in a water-bath at 100° C. for 10 minutes. After cooling to room temperature, a sample of the resulting solution was analyzed by radio-HPLC (Gradient L) and ITLC. The radiolabeling yield was ~93%.

Example XIV

[$^{99m}$Tc(HYNIC-Lys(OMe)-Pic)(tricine)]

To a sealed 5.0 mL vial were added 0.8 mL of HYNIC-Lys(OMe)-Pic solution (12 μg/mL) in 0.25 M succinate buffer (pH=5.0), and 0.2 mL of tricine solution (100 mg/mL in 0.25 M succinate buffer, pH=5.0). After addition of 0.3 mL of $^{99m}$TcO$_4^-$ solution (~35 mCi) and 25 μL of SnCl$_2$.2H$_2$O solution (1.0 mg/mL in 0.1 N HCl), the mixture was heated in a water-bath at 100° C. for 10 minutes. After cooling to room temperature, a sample of the resulting solution was analyzed by radio-HPLC (Gradient J) and ITLC. The radiolabeling yield was ~50%.

Example XV

[$^{99m}$Tc(HYNIC-HD-NIC)(tricine)]

To a sealed 5.0 mL vial were added 0.2 mL of HYNIC-HD-NIC solution (10 μg/mL) in ethanol, 0.5 mL of 0.25 M succinate buffer (pH=5.0), and 0.2 mL of tricine solution (100 mg/mL in 0.25 M succinate buffer, pH=5.0). After addition of 0.3 mL of $^{99m}$TcO$_4^-$ solution (~25 mCi) and 25 μL of SnCl$_2$.2H$_2$O solution (1.0 mg/mL in 0.1 N HCl), the mixture was heated in a water-bath at 100° C. for 10 minutes. After cooling to room temperature, a sample of the resulting solution was analyzed by radio-HPLC (Gradient I) and ITLC. The radiolabeling yield was >95%.

Example XVI

[$^{99m}$Tc(HYNIC-SP-NIC)(tricine)]

To a sealed 5.0 mL vial were added 0.2 mL of HYNIC-SP-NIC solution (10 μg/mL) in ethanol, 0.5 mL of 0.25 M succinate buffer (pH=5.0), and 0.2 mL of tricine solution (100 mg/mL in 0.25 M succinate buffer, pH=5.0). After addition of 0.3 mL of $^{99m}$TcO$_4^-$ solution (~25 mCi) and 25 μL of SnCl$_2$.2H$_2$O solution (1.0 mg/mL in 0.1 N HCl), the mixture was heated in a water-bath at 100° C. for 10 minutes. After cooling to room temperature, a sample of the resulting solution was analyzed by radio-HPLC (Gradient K) and ITLC. The radiolabeling yield was >95%.

Radiolabeling Efficiency Experiment. This experiment was designed to study the radiolabeling efficiency of HYNIC-Lys(OMe)-NIC. To a sealed 5.0 mL vial were added 0.1 to 0.4 mL of HYNIC-Lys(OMe)-NIC solution (10 μg/mL) in 0.25 M succinate buffer (pH=5.0), 0.1-0.4 mL of 0.25 M succinate buffer, pH=5.0), and 0.2 mL of tricine solution (100 mg/mL in 0.25 M succinate buffer, pH=5.0). After addition of 0.3 mL of $^{99m}$TcO$_4^-$ solution (~30 mCi) and 25 μL of SnCl$_2$.2H$_2$O solution (1.0 mg/mL in 0.1 N HCl), the mixture was heated in a water-bath at 100° C. for 10 minutes. After cooling to room temperature, a sample of the resulting solution was analyzed by radio-HPLC (Gradient I) and ITLC. Each condition was carried out in doublet and the radiolabeling yield was reported as the average of the two vials. The radiolabeling yield was summaried in Table 1. It is clear that the macrocyclic complex [$^{99m}$Tc(HYNIC-Lys(OMe)-NIC)(tricine)] can be prepared in high yield using 1 µg of HYNIC-Lys(OMe)-NIC for 30 mCi of $^{99m}$TcO$_4^-$, corresponding to the molar ratio of 8:1 for HYNIC-Lys(OMe)-NIC:$^{99m}$Tc.

TABLE 1

Radiolabeling yield for the macrocyclic complex [$^{99m}$Tc(HYNIC-Lys(OMe)-NIC)(tricine)]

| HYNIC-Lys(OMe)-NIC Level | Amount of $^{99m}$TcO$_4^-$ | Average Yield |
|---|---|---|
| 1 µg | 30 mCi | 94.8% |
| 2 µg | 30 mCi | 95.6% |
| 4 µg | 30 mCi | 96.8% |
| 5 µg | 30 mCi | 98.8% |
| 10 µg | 30 mCi | 98.8% |

Utility

The radiopharmaceuticals provided herein are useful as imaging agents for the diagnosis of cardiovascular disorders, such as thromboembolic disease or atherosclerosis, infectious disease and cancer. The radiopharmaceuticals are comprised of $^{99m}$Tc labeled hydrazino or diazenido modified biomolecules that selectively localize at sites of disease and thus allow an image to be obtained of the loci using gamma scintigraphy. Radiopharmaceuticals are administered by intravenous injection, usually in saline solution, at a dose of 1 to 100 mCi per 70 kg body weight, or preferably at a dose of 5 to 50 mCi. Imaging is performed using known procedures.

Platelet GPIIb/IIIa Receptor Antagonists or Fibrin Binding Peptides

Complexes in which the biomolecules, Q, are platelet GPIIb/IIIa receptor antagonists or fibrin binding peptides can be evaluated for potential clinical utility as radiopharmaceuticals for the diagnosis of disorders associated with platelet deposition by performing imaging studies in a canine deep vain thrombosis model or a canine arterio-venous shunt Model.

Canine Deep Vein Thrombosis Model

This model incorporates the triad of events (hypercoagulatible state, period of stasis, low shear environment) essential for the formation of a venous fibrin-rich actively growing thrombus. The procedure was as follows: Adult mongrel dogs of either sex (9-13 kg) were anesthetized with pentobarbital sodium (35 mg/kg, i.v.) and ventilated with room air via an endotracheal tube (12 strokes/min, 25 ml/kg). For arterial pressure determination, the right femoral artery was cannulated with a saline-filled polyethylene catheter (PE-240) and connected to a Statham pressure transducer (P23ID; Oxnard, Calif.). Mean arterial blood pressure was determined via damping the pulsatile pressure signal. Heart rate was monitored using a cardiotachometer (Biotach, Grass Quincy, Mass.) triggered from a lead II electrocardiogram generated by limb leads. The right femoral vein was cannulated (PE-240) for drug administration. A 5 cm segment of both jugular veins was isolated, freed from fascia and circumscribed with silk suture. A microthermister probe was placed on the vessel that serves as an indirect measure of venous flow. A balloon embolectomy catheter was utilized to induce the 15 minute period of stasis during which time a hypercoagulatible state was then induced using 5 U thrombin (American Diagnosticia, Greenwich Conn.) administered into the occluded segment. Fifteen minutes later, flow was reestablished by deflating the balloon. The radiopharmaceutical was infused during the first 5 minutes of reflow and the rate of incorporation monitored using gamma scintigraphy.

Canine Arteriovenous Shunt Model

Adult mongrel dogs of either sex (9-13 kg) were anesthetized with pentobarbital sodium (35 mg/kg,i.v.) and ventilated with room air via an endotracheal tube (12 strokes/min, 25 ml/kg). For arterial pressure determination, the left carotid artery was cannulated with a saline-filled polyethylene catheter (PE-240) and connected to a Statham pressure transducer (P23ID; Oxnard, Calif.). Mean arterial blood pressure was determined via damping the pulsatile pressure signal. Heart rate was monitored using a cardiotachometer (Biotach, Grass Quincy, Mass.) triggered from a lead II electrocardiogram generated by limb leads. A jugular vein was cannulated (PE-240) for drug administration. The both femoral arteries and femoral veins were cannulated with silicon treated (Sigmacote, Sigma Chemical Co. St Louis, Mo.), saline filled polyethylene tubing (PE-200) and connected with a 5 cm section of silicon treated tubing (PE-240) to form an extracorporeal arterio-venous shunts (A-V). Shunt patency was monitored using a doppler flow system (model VF-1, Crystal Biotech Inc, Hopkinton, Mass.) and flow probe (2-2.3 mm, Titronics Med. Inst., Iowa City, Iowa) placed proximal to the locus of the shunt. All parameters were monitored continuously on a polygraph recorder (model 7D Grass) at a paper speed of 10 mm/min or 25 mm/sec.

On completion of a 15 minute post surgical stabilization period, an occlusive thrombus was formed by the introduction of a thrombogenic surface (4-0 braided silk thread, 5 cm in length, Ethicon Inc., Somerville, N.J.) into the shunt one shunt with the other serving as a control. Two consecutive 1 hour shunt periods were employed with the test agent administered as an infusion over 5 minutes beginning 5 minutes before insertion of the thrombogenic surface. At the end of each 1-hour shunt period the silk was carefully removed and weighed and the % incorporation determined via well counting. Thrombus weight was calculated by subtracting the weight of the silk prior to placement from the total weight of the silk on removal from the shunt. Arterial blood was withdrawn prior to the first shunt and every 30 minutes thereafter for determination of blood clearance, whole blood collagen-induced platelet aggregation, thrombin-induced platelet degranulation (platelet ATP release), prothrombin time and platelet count. Template bleeding time was also performed at 30 minute intervals.

Chemotactic Peptides or LTB$_4$ Receptor Antagonists

Complexes in which the biomolecules, Q, are chemotactic peptides or LTB$_4$ receptor antagonists can be evaluated for potential clinical utility as radiopharmaceuticals for the diagnosis of infection by performing imaging studies in a guinea pig model of focal infection.

Guinea Pig Focal Infection Model

Hartley guinea pigs; unspecified sex; weight between 200-250 grams are fasted overnight prior to the procedure. Each guinea pig is anesthetized with a mixture of ketamine 25-55 mg/kg//IM and xylazine 2-5 mg/kg/IM. A #10 trochar needle is used to introduce a 2 inch piece of umbilical string that has been immersed in a 6% sodium caseinate solution (this is the chemoattractant) into the right flank and is placed on the left side of the peritoneal cavity. The placement of the chemoattractant serves as a focal site for white blood cell recruitment. The puncture site is sealed with Nexabain, a skin glue (if required). The animals are allowed to recover for 18 hours.

Eighteen hours later the guinea pigs are anesthetized with ketamine 25-55 mg/kg//IM and xylazine 2-5 mg/kg/IM to achieve Stage III/Plane III of anesthesia and insure proper injection of the test agent into the lateral saphenous vein. Once the test agent is administered the guinea pigs are placed behind a lead shield and monitored for 1-4 hours. At the appropriate time postinjection, the animals are euthanized with pentobarbital sodium 65 mg/kg, I.V., and a biodistribution performed. Throughout the course of the study, blood samples are withdrawn via cardiac puncture.

MMP Inhibitors, $LTB_4$ Receptor Antagonists, or Vitronectin Receptor Antagonists Complexes in which the biomolecules, Q, are MMP inhibitors, $LTB_4$ receptor antagonists, or vitronectin receptor antagonists can be evaluated for potential clinical utility as radiopharmaceuticals for the diagnosis of atherosclerosis in a rabbit experimental atherosclerosis model.

Rabbits Model for Imaging Experimental Atherosclerosis

The study involves the use of male New Zealand white rabbits, 3-4 kg, fed with either normal rabbit diet as controls or a diet with 1.5% cholesterol added (Bio-Serv, Inc., Frechtown, N.J.) for 3 months. After 1 week of the hyperlipidemic diet, the abdominal aorta was denuded of endothelium by a modified Baumgartener technique (Baumgartener, H. R. *Z. Gesamte Exp. Med.* 1963, 137, 227-249; Narula et al., *Circulation* 1995, 92,474-484; Narula et al., *J. Nucl. Cardiol.* 1996, 3, 231-241; Elmaleh et al., *Proc. Natl. Sci. USA* 1998, 95, 691-695). Briefly, each animal was anesthetized with a mixture of ketamine and xylazine (100 mg/mL, 10:1 v:/v; 1.5-2.5 mL/sc), and the right femoral artery was isolated. A 4F Fogarty embolectomy catheter was introduced through an arteriotomy and advanced under fluoroscopic guidance to the level of the diaphragm. The catheter was inflated to a pressure of 3 psi above the balloon inflation pressure with radiographic contrast media (Conray, Mallinckrodt), and three passes were made down the abdominal aorta with the inflated catheter. The femoral artery was then ligated, and the wound was closed. The animals were allowed to recover from anesthesia and then returned to their cages. The animals continued to consume a hyperlipidemic diet for 11 additional weeks.

After 3 month on the hyperlipidemic diet, animals for imaging studies were injected into the marginal ear vein with approximately 0.5 mCi of the radiopharmaceutical. The animals are positioned on the camera head so as to image the anterior or posterior of the animals. Serial 5-minute dynamic images are acquired over 2 hours using a 256×256 matrix and a zoom of 2×. A known source is placed in the image field (20-90 µCi) to evaluate region of interest (ROI) uptake. Images were also acquired 24 hours post injection to determine retention of the compound in the aorta. Upon completion of the study, the images are evaluated by manually circumscribing the aorta region as the target region of interest (ROI) and a background site in the surrounding area. The uptake is determined by taking the fraction of the total counts in an inscribed area for ROI/source and multiplying the known µCi. After imaging, the animals were sacrificed for biodistribution or autoradiographic examinations of the appropriate organs.

MMP Inhibitors, Vitronectin Receptor Antagonists, Somatostatin Analogues, or Growth Factor Receptor Antagonists Complexes in which the biomolecules, Q, are MMP inhibitors, vitronectin receptor antagonists, somatostatin analogues, or growth factor receptor antagonists can be evaluated for potential clinical utility as radiopharmaceuticals for the diagnosis of tumors in a c-Neu Oncomouse® model, a matrigel model or a canine Spontaneous tumor model.

Oncomouse® Imaging

The study involves the use of the c-Neu Oncomouse® and FVB mice simultaneously as controls. The mice are anesthetized with sodium pentobarbital and injected with approximately 0.5 mCi of radiopharmaceutical. Prior to injection, the tumor locations on each Oncomouse® are recorded and tumor size measured using calipers. The animals are positioned on the camera head so as to image the anterior or posterior of the animals. 5 Minute dynamic images are acquired serially over 2 hours using a 256×256 matrix and a zoom of 2×. Upon completion of the study, the images are evaluated by circumscribing the tumor as the target region of interest (ROI) and a background site in the neck area below the carotid salivary glands.

Rabbit Matrigel Model

This model was adapted from a matrigel model intended for the study of angiogenesis in mice. Matrigel (Becton & Dickinson, USA) is a basement membrane rich in laminin, collagen IV, entactin, HSPG and other growth factors. When combined with growth factors such as bFGF [500 ng/ml] or VEGF [2 µg/ml] and injected subcutaneously into the midabdominal region of the mice, it solidifies into a gel and stimulates angiogenesis at the site of injection within 4-8 days. In the rabbit model, New Zealand White rabbits (2.5-3.0 kg) are injected with 2.0 ml of matrigel, plus 1 µg bFGF and 4 µg VEGF. The radiopharmaceutical is then injected 7 days later and the images obtained.

Canine Spontaneous Tumor Model

Adult dogs with spontaneous mammary tumors were sedated with xylazine (20 mg/kg)/atropine (1 ml/kg). Upon sedation the animals were intubated using ketamine (5 mg/kg)/diazepam (0.25 mg/kg) for full anesthesia. Chemical restraint was continued with ketamine (3 mg/kg)/xylazine (6 mg/kg) titrating as necessary. If required the animals were ventilated with room air via an endotrachael tube (12 strokes/min, 25 ml/kg) during the study. Peripheral veins were catheterized using 20G I.V. catheters, one to serve as an infusion port for compound while the other for exfusion of blood samples. Heart rate and EKG were monitored using a cardiotachometer (Biotech, Grass Quincy, Mass.) triggered from a lead II electrocardiogram generated by limb leads. Blood samples are generally taken at ~10 minutes (control), end of infusion, (1 minute), 15 min, 30 min, 60 min, 90 min, and 120 min for whole blood cell number and counting. Radiopharmaceutical dose was 300 µCi/kg administered as an i.v. bolus with saline flush. Parameters were monitored continuously on a polygraph recorder (Model 7E Grass) at a paper speed of 10 mm/min or 10 mm/sec.

Imaging of the laterals were for 2 hours with a 256×256 matrix, no zoom, 5 minute dynamic images. A known source is placed in the image field (20-90 μCi) to evaluate region of interest (ROI) uptake. Images were also acquired 24 hours post injection to determine retention of the compound in the tumor. The uptake is determined by taking the fraction of the total counts in an inscribed area for ROI/source and multiplying the known μCi. The result is μCi for the ROI.

The disclosures of each patent, patent application and publication cited or described in this document are hereby incorporated herein by reference, in their entirety.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula:

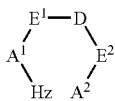

or a pharmaceutically acceptable salt thereof, wherein:
$E^1$ is C(O);
$E^2$ is a direct bond;
Hz is the free hydrazine moiety or a hydrazone of the formula —N($R^1$)N═C($R^2$)($R^3$);
$R^1$ is selected from: H, $C_1$-$C_{10}$ alkyl substituted with 0-5 $R^4$, $C_2$-$C_{10}$ alkenyl substituted with 0-5 $R^4$, $C_6$-$C_{10}$ aryl substituted with 0-3 $R^4$, and $C_4$-$C_{10}$ heteroaryl substituted with 0-3 $R^4$;
$R^2$ and $R^3$ are independently selected at each occurrence from: H, CN, $Co_2R^5$, $C(O)R5$, $C(O)N(R5)_2$, $C_1$-$C_{10}$ alkyl substituted with 0-5 $R^5$, $C_2$-$C_{10}$ alkenyl substituted with 0-5 $R^5$, $C_3$-$C_{10}$ cycloalkyl substituted with 0-5 $R^5$, $C_6$-$C_{10}$ aryl substituted with 0-3 $R^5$, and $C_4$-$C_{10}$ heteroaryl substituted with 0-3 $R^5$: or alternatively $R^2$ and $R^3$ may be taken together to form a $C_3$-$C_{10}$ cycloalkyl or $C_5$-$C_{10}$ cycloalkenyl;
$R^4$ is independently selected at each occurrence from: OH, COOH, C(O)NH$_2$, SO$_3$H, and SO$_2$NH$_2$;
$R^5$ is independently selected at each occurrence from: C(═O)OR$^6$, C(O)NHR$^6$, C(═O)R$^6$, NHR$^6$, NHC(═O)R$^6$, NHC(═O)NHR$^6$, NHC(═S)NHR$^6$, OR$^6$, OC(═O)R$^6$, OC(═O)OR$^6$, PO(OR$^6$), SR$^6$, SOR$^6$, SO$_2$R$^6$, SO$_3$R$^6$, and SO$_2$NHR$^6$;
$R^6$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;
$A^1$ is pyridinyl;
$A^2$ is an imine-N-containing $C_5$ heterocycle substituted with C-2 $R^7$;
$R^7$ is independently selected at each occurrence from: C(═O)CR$^8$, C(O)NHR$^8$, C(═O)R$^8$, NHR$^8$, NHC(═O)R$^8$, NHC(═O)NHR$^8$, NHC(═S)NHR$^8$, OR$^8$, OC(═O) R$^8$, OC(═O)OR$^8$, PO(OR$^8$)$_2$, SR$^8$, SO$_2$R$^8$, SO$_3$R$^8$, and SO$_2$NHR$^8$;
$R^8$ is independently selected at each occurrence from: H, $C_1$-$C_{10}$ alkyl, $C_2$-$C_{10}$ alkenyl, $C_3$-$C_{10}$ cycloalkyl, $C_6$-$C_{10}$ aryl, and $C_4$-$C_{10}$ heteroaryl;

D is selected from the group consisting of O, S and N; and
Z is a bond.

2. A compound according to claim 1, wherein
$R^1$ is selected from: H, $C_1$-$C_{10}$ alkyl substituted with 0-3 $R^4$, $C_2$-$C_{10}$ alkenyl substituted with 0-3 $R^4$, $C_6$-$C_{10}$ aryl substituted with 0-2 $R^4$, and $C_4$-$C_{10}$ heteroaryl substituted with 0-2 $R^4$;
$R^2$ and $R^3$ are independently selected at each occurrence from: H, $C_{6-C10}$ aryl substituted with 0-2 $R^5$, and $C_4$-$C_{10}$ heteroaryl substituted with 0-2 $R^5$;
$R^4$ is independently selected at each occurrence from: OH, COOH, and SO$_3$H;
$R^5$ is independently selected at each occurrence from: C(═O)OH, C(O)NHR$^6$, NHR$^6$, NHC(═O)R$^6$, NHC(═S)NHR$^6$, SO$_2$R$^6$, SO$_3$H, and SO$_2$NHR$^6$;
$R^6$ is independently selected at each occurrence from: H, $C_1$-$C_{10}$ alkyl, $C_6$-$C_{10}$ aryl, and $C_4$-$C_{10}$ heteroaryl;
$A^2$ is an imine-N containing $C_5$ heterocycle;
$R^7$ is independently selected at each occurrence from: C(═O)OH, C(O)NHR$^8$, NHR$^8$, NHC(═O)R$^8$, SO$_3$H, and SO$_2$NHR$^8$; and
$R^8$ is independently selected at each occurrence from: H, $C_1$-$C_{10}$ alkyl, $C_6$-$C_{10}$ aryl, and $C_4$-$C_{10}$ heteroaryl.

3. A compound according to claim 2, wherein
$R^1$ is selected from: H, $C_1$-$C_{10}$ alkyl, $C_6$-$C_{10}$ aryl, and $C_4$-$C_{10}$ heteroaryl;
$R^2$ and $R^3$ are independently selected at each occurrence from: H, phenyl substituted with $R^5$, $C_4$-$C_6$ heteroaryl substituted with $R^5$;
$R^5$ is independently selected at each occurrence from: C(═O)OH, C(O)NHR$^6$, NHR$^6$, NHC(═O)R$^6$, SO$_3$H, and SO$_2$NHR$^6$;
$R^6$ is independently selected at each occurrence from: H and $C_1$-$C_5$ alkyl; and
$A^2$ is pyridine.

4. A compound according to claim 3, wherein
$R^1$ is H;
$R^2$ and $R^3$ are independently selected at each occurrence from: H and phenyl substituted with $R^5$; and
$R^5$ is C(═O)OH or SO$_3$H.

5. A compound according to claim 4, wherein
$R^2$ is H; and
$R^3$ is 2-sulfonatophenyl.

6. A compound of the formula:

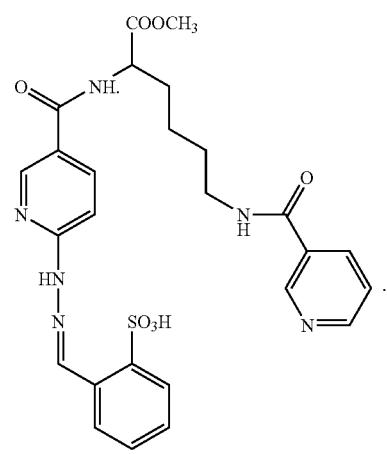

7. A compound of the formula:
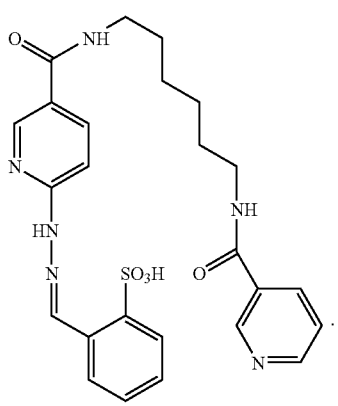
8. A compound of the formula:
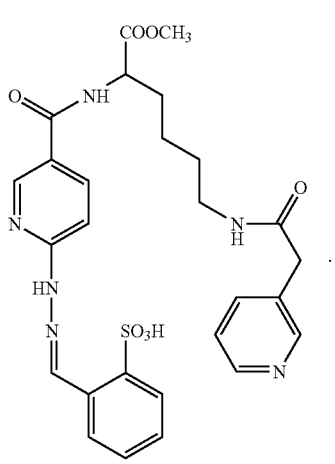
9. A compound of the formula:
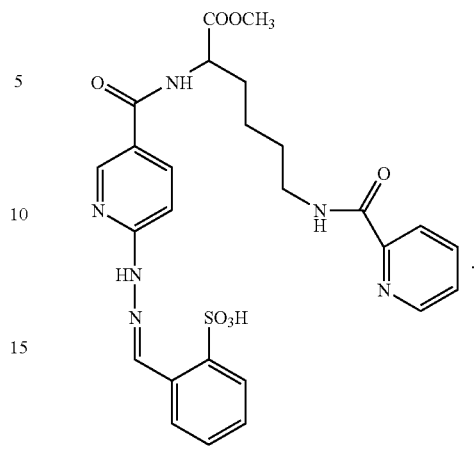
10. A compound of the formula:
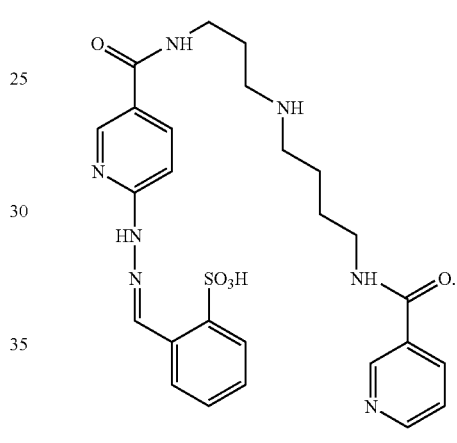
* * * * *